US010869879B2

(12) United States Patent
Bhattacharjee

(10) Patent No.: US 10,869,879 B2
(45) Date of Patent: *Dec. 22, 2020

(54) COMBINATIONS TO TREAT CANCER

(71) Applicant: EVOL SCIENCE LLC, Lower Gwynedd, PA (US)

(72) Inventor: Vikram Bhattacharjee, Lower Gwynedd, PA (US)

(73) Assignee: EVOL SCIENCE LLC, Lower Gwynedd, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/295,092

(22) Filed: Mar. 7, 2019

(65) Prior Publication Data

US 2019/0216837 A1  Jul. 18, 2019
US 2020/0046749 A9  Feb. 13, 2020

Related U.S. Application Data

(63) Continuation of application No. PCT/US2018/045571, filed on Aug. 7, 2018.

(60) Provisional application No. 62/608,265, filed on Dec. 20, 2017, provisional application No. 62/541,911, filed on Aug. 7, 2017.

(51) Int. Cl.
| *A61K 31/7068* | (2006.01) |
| *A61K 45/06* | (2006.01) |
| *A61P 35/00* | (2006.01) |
| *A61K 9/00* | (2006.01) |
| *A61K 31/4375* | (2006.01) |
| *A61K 31/44* | (2006.01) |
| *A61K 31/505* | (2006.01) |
| *A61K 31/506* | (2006.01) |
| *A61K 31/519* | (2006.01) |

(52) U.S. Cl.
CPC ........ *A61K 31/7068* (2013.01); *A61K 9/0019* (2013.01); *A61K 9/0053* (2013.01); *A61K 31/4375* (2013.01); *A61K 31/44* (2013.01); *A61K 31/505* (2013.01); *A61K 31/506* (2013.01); *A61K 31/519* (2013.01); *A61K 45/06* (2013.01); *A61P 35/00* (2018.01)

(58) Field of Classification Search
CPC ... A61K 31/7068; A61K 31/44; A61K 31/505
See application file for complete search history.

(56) References Cited

U.S. PATENT DOCUMENTS

| 9,545,382 B2 | 1/2017 | Koyakutty et al. | |
| 2012/0213867 A1* | 8/2012 | Stuart | A61K 31/4439 424/649 |
| 2015/0164934 A1* | 6/2015 | Bellacosa | A61K 31/122 514/49 |
| 2015/0342896 A1 | 12/2015 | Koyakutty et al. | |
| 2016/0310476 A1 | 10/2016 | Saha et al. | |
| 2016/0355510 A1* | 12/2016 | Springer | C07D 471/04 |

FOREIGN PATENT DOCUMENTS

| WO | 2015095819 A2 | 6/2015 |
| WO | 2017136741 A1 | 8/2017 |
| WO | 2019183216 A1 | 9/2019 |

OTHER PUBLICATIONS

Su (Clinical Cancer Research; 18(8), 2012, 2184-2198).*
Sacks (Clinical Thyroidology; 2013, 25:20-23).*
PDR (https://www.pdr.net/drug-summary/Cisplatin-cisplatin-1472. 4558; printed Nov. 20, 2019).*
Chou et al., "Quantitative analysis of dose-effect relationships: the combined effects of multiple drugs or enzyme inhibitors." Adv Enzym Regul (1984) vol. 22, pp. 27-55.
Hatzivassiliou et al., "RAF inhibitors prime wild-type RAF to activate the MAPK pathway and enhance growth" Nature (2010) 464, 431-435.
Laurent-Puig et al., "Analysis of PTEN, BRAF, and EGFR Status in Determining Benefit From Cetuximab Therapy in Wild-Type KRAS Metastatic Colon Cancer", Journal of 61",65-76,82-102 Clinical Oncology. 2009. vol. 27 (35), pp. 5924-5930.
Yokota "Are KRAS/BRAF Mutations Potent Prognostic and/or Predictive Biomarkers in Colorectal Cancers?" Anti-Cancer Agents in Medicinal Chemistry. 2012. vol. 12, 61,65-76,82-102 pp. 163-171.
Ross et al., "Identification of the serine biosynthesis pathway as a critical component of BRAF inhibitor resistance of melanoma, pancreatic, and non-small cell lung cancer cells" Mol Cancer Ther. May 12, 2017 vol. 16 No. 8 pp. 1596-1609.
Goncalves et al., "BAYPAN study: a double-blind phase III randomized trial comparing gemcitabine plus sorafenib and gemcitabine plus placebo in patients with advanced pancreatic cancer" Ann Oncol. Nov. 2012 vol. 23 No. 11. pp. 2799-2805.
Queirolo et al., "Combined vemurafenib and fotemustine in patients with BRAF V600 melanoma progressing on vemurafenib" Oncotarget. 2016 vol. 9. No. 15. pp. 12408-12417.
Planchard et al., "An open-label phase 2 trial of dabrafenib plus trametinib in patients with previously treated BRAFV600E—mutant metastatic non-small cell lung cancer", Lancet Oncol. 2016 vol. 17 No. 7. pp. 984-993.
Sullivan et al., "BRAF in Melanoma: Pathogenesis, Diagnosis, Inhibition, and Resistance", Journal of Skin Cancer (2011) pp. 1-8.
Tedeschi et al., "Contribution of serine, folate and glycine metabolism to the ATP, NADPH and purine requirements of cancer cells", Cell Death and Disease (2013) 1-12.
Tham et al., "A PharmacodynamicModel for the Time Course of Tumor Shrinkage by Gemcitabine + Carboplatin in Non-Small Cell Lung Cancer Patients", Clin Cancer Res (2008) 14: 4213-4218.

(Continued)

*Primary Examiner* — Pancham Bakshi
(74) *Attorney, Agent, or Firm* — Troutman Pepper Hamilton Sanders LLP

(57) ABSTRACT

This application describes compounds, compositions, and combinations thereof that can be used to treat cancer, such as cancers with and without BRAF and/or RAS mutations.

16 Claims, 51 Drawing Sheets

(56) References Cited

OTHER PUBLICATIONS

Tsai et al., "Discovery of a selective inhibitor of oncogenic B-Raf kinase with potent antimelanoma activity", PNAS (2018) vol. 105, No. 8: 3041-3046.
Villanueva et al., "Concurrent MEK2 Mutation and BRAF Amplification Confer Resistance to BRAF and MEK Inhibitors in Melanoma", Cell Reports (2013) 4, 1090-1099.
Wolfgang et al., "Recent Progress in Pancreatic Cancer", CA Cancer J Clin (2013) 63:318-348.
Corcoran et al., "BRAF Gene Amplification Can Promote Acquired Resistance to MEK Inhibitors in Cancer Cells Harboring the BRAF V600E Mutation", Sci Signal (2008) 3: 149; 1-20.
Bhattacharjee et al., "A synthetic lethal screen identifies the Vitamin D receptor as a novel gemcitabine sensitizer in pancreatic cancer cells", Cell Cycle (2014) 13:24, 3839-3856.
Beroukhim et al., "The landscape of somatic copy—number alteration across human cancers", Nature. (2010) 463 (7283): 899-905.
Baenke et al., "Resistance to BRAF inhibitors induces glutamine dependency in melanoma cells", Molecularoncology (2015 ) 10: 73-84.
Atefi et al., "Reversing Melanoma Cross-Resistance to BRAF and MEK Inhibitors by Co-Targeting the AKT/mTOR Pathway", PLoS ONE (2011) 6(12): e28973. doi:10.1371/journal.pone.0028973.
Acquaviva et al., "Overcoming Acquired BRAF Inhibitor Resistance in Melanoma via Targeted Inhibition of Hsp90 with Ganetespib" Mol Cancer Ther (2014) DOI: 10.1158/1535-7163.-13-0481 pp. 353-363.
Abdel-Wahab et al., "Efficacy of Intermittent Combined RAF and MEK Inhibition in a Patient with Concurrent BRAF- and NRAS-Mutant Malignancies", Cancer Discovery (2014) vol. 4, Issue 5; http://cancerdiscovery.aacrjournals.org/content/4/5/538.full-text.pdf.
Hatzivassiliou et al., "RAF inhibitors prime wild-type RAF to activate the MAPK pathway and enhance growth", Nature (2010) vol. 464 pp. 431-436.
Gowrishankar et al., "Acquired Resistance to BRAF Inhibition Can Confer Cross-Resistance to Combined BRAF/MEK Inhibition" Journal of Investigative Dermatology (2012) 132, 1850-1859.
Girotti et al., "Inhibiting EGF Receptor or SRC Family Kinase Signaling Overcomes BRAF Inhibitor Resistance in Melanoma", American Association for Cancer (2013) Downloaded from cancerdiscovery.aacrjournals.org.
Flaherty et al., "Combined BRAF and MEK Inhibition in Melanoma with BRAF V600 Mutations", N Engl J Med. (2012) 367(18): 1694-1703.
Feldmann et al., "In vitro models of pancreatic cancer for translational oncology research", Expert Opin Drug Discov. Apr. 1, 2009; 4(4): 429-443.
Fedorenko et al., "Fibronectin induction abrogates the BRAF inhibitor response of BRAF V600E/PTEN-null melanoma cells", Oncogene. Mar. 10, 2016; 35(10): 1225-1235.
Fedorenko et al., "Acquired and intrinsic BRAF inhibitor resistance in BRAF V600E mutant melanoma" Biochem Pharmacol. Aug. 1, 2011; 82(3): 201-209.
Erster et al., "In Vivo Mitochondrial p53 Translocation Triggers a Rapid First Wave of Cell Death in Response to DNA Damage That Can Precede p53 Target Gene Activation", Molecular and Cellular Biology, Aug. 2004, p. 6728-6741.
DeNicola et al., " NRF2 regulates serine biosynthesis in non-small cell lung cancer", Nat Genet. Dec. 2015; 47 (12): 1475-1481.
Meacham et al., "Tumor heterogeneity and cancer cell plasticity", Nature. Sep. 19, 2013; 501(7467): 328-337.
Markkanen et al., "Cells deficient in base-excision repair reveal cancer hallmarks originating from adjustments to genetic instability", Nucleic Acids Research, 2015, vol. 43, No. 7 3667-3679.
Locasale et al., "Phosphoglycerate dehydrogenase diverts glycolytic flux and contributes to oncogenesis", Nat Genet. (2013) 43(9): 869-874.
Li et al., "Phenotype switching in melanoma: implications for progression and therapy", Front Oncol (2015) vol. 5:31; 1-7.
Labuschagne et al., "Serine, but Not Glycine, Supports One-Carbon Metabolism and Proliferation of Cancer Cells", Cell Reports (2014) 7, 1248-1258.
Hayashi et al., "Gemcitabine: Efficacy in the Treatment of Advanced Stage Nonsquamous Non-Small Cell Lung Cancer", Clinical Medicine Insights: Oncology 2011:5 177-184.
Halaban et al., "PLX4032, a selective BRAFV600E kinase inhibitor, activates the ERK pathway and enhances cell migration and proliferation of BRAFWT melanoma cells", Pigment Cell Melanoma Res. (2010) 23; 190-200.
Greger et al., "Combinations of BRAF, MEK, and PI3K/mTOR Inhibitors Overcome Acquired Resistance to the BRAF Inhibitor GSK2118436 Dabrafenib, Mediated by NRAS or MEK Mutations", Molecular Cancer Therapeutics (2012) vol. 11 Issue 4.
Paulitschke et al., "Vemurafenib Resistance Signature by Proteome Analysis Offers New Strategies and Rational Therapeutic Concepts", Mol Cancer Ther (2015) 14(3) 757-768.
Old et al., "Functional Proteomics Identities Targets of Phosphorylation by BRaf Signaling in Melanoma", Mol Cell. Apr. 10, 2009; 34(1): 115-131.
Muller et al., "Mutant p53 in Cancer: New Functions and Therapeutic Opportunities", Cancer Cell (2014) 25: 304-317.
Ohhashi et al., "Down-regulation of Deoxycytidine Kinase Enhances Acquired Resistance to Gemcitabine in Pancreatic Cancer", Anticancer Research (2008) 28: 2205-2212.
Morris et al., "Discovery of a Novel ERK Inhibitor with Activity in Models of Acquired Resistance to BRAF and MEK Inhibitors", Cancer Discovery (2013) pp. 742-750 Downloaded from cancerdiscovery.aacrjournals.org on Jan. 17, 2019.
Moriceau et al., "Tunable-Combinatorial Mechanisms of Acquired Resistance Limit the Efficacy of BRAF/MEK Cotargeting but Result in Melanoma Drug Addiction", Cancer Cell (2015) 27, 240-256.
Morgan et al., "Radiosensitization by Gemcitabine Fixed-Dose-Rate Infusion Versus Bolus Injection in a Pancreatic Cancer Model", Translational Oncology (2008) 1, 44-49.
Menzies et al., "Dabrafenib and its potential for the treatment of metastatic melanoma", Drug Design, Development and Therapy (2012) 6 391-405.
Senturk et al., "p53 and Cell Cycle Effects After DNA Damage", Methods Mol Biol. (2013) 962: 49-61.
Sala et al., "BRAF Silencing by Short Hairpin RNA or Chemical Blockade by PLX4032 Leads to Different Responses in Melanoma and Thyroid Carcinoma Cells", Mol Cancer Res (2008) 6(5) 751-759.
Rubin et al., "Targeting the Hedgehog pathway in cancer", Nature Reviews | Drug Discovery (2006) vol. 5; 1026-1033.
Qian et al., "Groups of p53 target genes involved in specific p53 downstream effects cluster into different classes of DNA binding sites", Oncogene (2002) 21, 7901-7911.
Poulikakos et al., "RAF inhibitors transactivate RAF dimers and ERK signaling in cells with wild-type BRAF", Nature. (2010) 464(7287): 427-430.
Possemato et al., "Functional genomics reveals serine synthesis is essential in PHGDG-amplified breast cancer", Nature. (2012) 476(7360): 346-350.
Pietenpol et al., "Sequence-specific transcriptional activation is essential for growth suppression by p53", Proc. Natl. Acad. Sci. USA (1994) vol. 91, pp. 1998-2002.
Paulson et al., "Therapeutic Advances in Pancreatic Cancer", Gastroenterology 2013;144:1316-1326.
Shi et al., "Acquired Resistance and Clonal Evolution in Melanoma during BRAF Inhibitor Therapy" American Association for Cancer Discov (2013) 4(1); 80-93.
Spagnolo et al., "BRAF-mutant melanoma: treatment approaches, resistance mechanisms, and diagnostic strategies", OncoTargets and Therapy (2015) 8 157-168.
Snell et al, "The modulation of serine metabolism in hepatoma 3924A during different phases of cellular proliferation in culture", Biochem J. (1987) 245, 609-612.
Snell et al., "Enzymic imbalance in serine metabolism in human colon carcinoma and rat sarcoma", Br. J. Cancer (1988), 57, 87-90.

(56) References Cited

OTHER PUBLICATIONS

Sneader W., " Drug Discovery A History", School of Pharmacy University of Strathclyde, Glasgow, UK, (2005) pp. 1-447.

Smalley, et al., "Multiple signaling pathways must be targeted to overcome drug resistance in cell lines derived from melanoma metastases" Mol Cancer Ther (2006) 5(5):1136-44.

Fryer et al., "Mechanisms Underlying Gemcitabine Resistance in Pancreatic Cancer and Sensitisation by the iMiD™ Lenalidomide", Anticancer Research (2011) 31:3747-3756.

Long et al., "Dabrafenib and trametinib versus dabrafenib and placebo for Val600 BRAF-mutant melanoma: a multicentre, double-blind, phase 3 randomised controlled trial" Published Online (May 31, 2015) http://dx.doi.org/10.1016/S0140-6736(15) 60898-4.

Non-Final Office Action issued in U.S. Appl. No. 16/074,881 dated Feb. 28, 2020.

Roos et al., "B-RAF inhibitor vemurafenib in combination with temozolomide and fotemustine in the killing response of malignant melanoma cells", Oncotarget (2014) vol. 5, No. 24, 12607-12620.

Staehler et al., "Sorafenib After Combination Therapy With Gemcitabine Plus Doxurubicine in Patients with Sarcomatoid Renal cell Carcinoma: A prospective Evaluation", Eur J med Res (2010) 14:287-291.

Richly et al., "Combination of sorfenib and doxorubicin in patients with advanced hepatocellulare carcinoma: Results 'from a phase I extension trial", Eur. J. Cancer (2009) 45: 579-597.

Kim et al., "Phase I dose-finding study of sorafenib in combination with capecitabine and cisplatin as a first-line treatment in patients with advanced gastric cancer", Invest New Drugs (2012) 30:306-315.

Schultheis et al., "Phase IB study of sorafenib in combination with gemcitabine and cisplatin in patients with refractory solid tumors", Cancer Chemother Pharmacol (2012) 69:333-339.

Petrini et al., "Phase II trial of sorafenib in combination with 5-fluorouracil infustion in advanced hepatocellular carcinoma", Cancer Chemother Pharmacol (2012) 69:773-780.

Miyata et al., "Safety and efficacy of combination therapy with low-dose gemcitabine, paclitaxel, and sorafenib in patients with cisplatin-resistant urothelial cancer", Med Oncol (2015) 32:325.

Kupsch et al., "Results of a Phase I Trial of Sorafenib (BAY 43/9006) in Combination with Oxaliplatin in Patients with Refractory Solid Tumors, including Colorectal Cancer", Clinical Colorectal Cancer, (2005)vol. 5, No. 3, 188-196.

Sun et al., "Phase II Study of Sorafenib in Combination With Docetaxel and Cisplatin in the Treatment of Metastatic or Advanced Gastric and Gastroesophageal Junction Adenocarcinoma: ECOG 5203", J Clin Oncol (2010) 28:2947-2951.

Ramasubbaiah et al., "Sorafenib in combination with weekly topotecan in recurrent ovarian cancer, a phase I/II study of the Hoosier Oncology Group", Gynecologic Oncology 123 (2011) 499-504.

Murai et al., "Stereocpecific PARP Trapping by BMN 673 and Comparison with Olaparib and Rucaparib", Mol Cancer Ther (2014) 13(2):433-443.

Williams et al., "Discovery of RAF265: A Potent mut-B-RAF Inhibitor for the Treatment of Metastatic Melanoma", ACS Med. Chem. Lett. (2015) 6:961-965.

Sun et al., "Rational combination therapy with PARP and MEK inhibitors capitalizes on therapeutic liablities in RAS mutant cancers", Sci.Transl. Med. (2017) 9, eaal5148: 1-18.

* cited by examiner

EC50: Pancreatic cancer; BRAF-WT, KRAS G12C, mesenchymal = 0.1895 uM
Melanoma; BRAF V600E, KRAS-WT, polygonal = 0.4136 uM
Pancreatic cancer; BRAF-WT, KRAS G12C, epithelial = > 15uM Chou Talalay constant ratio synergy tests (Pancreatic cancer): Gemcitabine, Paclitaxel (Abraxane), BRAF-WT activator (BRAF V600E inhibitor)

BxPC3M1
Gemcitabine + Paclitaxel + Encorafenib

Mesenchymal PC cell line
BRAF-WT
KRAS *G12C*

KPC FC 1242
Gemcitabine + Paclitaxel +
Dabrafenib

Standard PC mouse model cell line
BRAF-WT
KRAS *G12D*

SK-MEL-28VR1
Gemcitabine + GDC0879

Metastatic melanoma line
BRAF *V600E*
KRAS WT

SK-MEL-28VR1
Gemcitabine + AD80

Metastatic melanoma line
BRAF WT
KRAS *G12V*

501mel
Gemcitabine + GDC0879

Metastatic melanoma line
BRAF *V600E*
NRAS *G12D*

501mel
Gemcitabine + AD80

Metastatic melanoma line
BRAF *V600E*
NRAS *G12D*

**Panc1
Gemcitabine + GDC0879**

Pancreatic cancer line
BRAF WT
KRAS *G12D*

**Panc1
Gemcitabine + AD80**

Pancreatic cancer line
BRAF WT
KRAS *G12D*

**BxPC3M1
Gemcitabine + GDC0879**

Pancreatic cancer line
BRAF WT
KRAS *G12C*

**BxPC3M1
Gemcitabine + AD80**

Pancreatic cancer line
BRAF WT
KRAS *G12C*

SK-MEL-28VR1
Gemcitabine + ZM336372

Metastatic melanoma line
BRAF WT
KRAS *G12V*

SK-MEL-28VR1
Gemcitabine + NVPBHG712

Metastatic melanoma line
BRAF WT
KRAS *G12V*

**501mel
Gemcitabine + ZM336372**

**Metastatic melanoma line
BRAF *V600E*
NRAS *G12D***

**501mel
Gemcitabine + NVPBHG712**

**Metastatic melanoma line
BRAF *V600E*
NRAS *G12D***

Panc1
Gemcitabine + ZM336372

Pancreatic cancer line
BRAF WT
KRAS *G12D*

Panc1
Gemcitabine + NVPBHG712

Pancreatic cancer line
BRAF WT
KRAS *G12D*

**BxPC3M1
Gemcitabine + ZM336372**

Pancreatic cancer line
BRAF WT
KRAS *G12C*

**BxPC3M1
Gemcitabine + NVPBHG712**

Pancreatic cancer line
BRAF WT
KRAS *G12C*

SK-MEL-28VR1
Gemcitabine + RAF265

**Metastatic melanoma line
BRAF WT
KRAS *G12V***

SK-MEL-28VR1
Gemcitabine + TAK632

**Metastatic melanoma line
BRAF WT
KRAS *G12V***

501mel
Gemcitabine + RAF265

Metastatic melanoma line
BRAF V600E
**NRAS *G12D***

501mel
Gemcitabine + TAK632

Metastatic melanoma line
BRAF V600E
**NRAS *G12D***

Panc1
Gemcitabine + RAF265

Pancreatic cancer line
BRAF WT
KRAS *G12D*

Panc1
Gemcitabine + TAK632

Pancreatic cancer line
BRAF WT
KRAS *G12D*

**BxPC3M1
Gemcitabine + RAF265**

Pancreatic cancer line
BRAF WT
KRAS *G12C*

**BxPC3M1
Gemcitabine + TAK632**

Pancreatic cancer line
BRAF WT
KRAS *G12C*

SK-MEL-28VR1: (*KRAS G12V*, BRAF WT)

SK-MEL-28VR1: (*KRAS G12V*, BRAF WT)

PANC1: (KRAS G12D, BRAF WT)

Panc1
Methotrexate + XP102

Pancreatic cancer line
BRAF WT
KRAS *G12D*

BxPC3M1: (*KRAS G12C*, BRAF WT)

**BxPC3M1
Methotrexate + XP102**

**Pancreatic cancer line
BRAF WT
KRAS *G12C***

**SW620
Methotrexate + XP102**

Colon cancer line
BRAF WT
KRAS *G12V*

**A549
Methotrexate + XP102**

**Lung cancer line
BRAF WT
KRAS *G12V***

**SK-MEL-28VR1
Gemcitabine + E6201**

**Metastatic melanoma line
BRAF WT
KRAS *G12V***

COMBINATIONS TO TREAT CANCER

CROSS-REFERENCE TO RELATED APPLICATIONS

This application is a continuation of PCT Application No. PCT/US2018/045571, filed on Aug. 7, 2018, which claims priority to U.S. Provisional Application No. 62/541,911, filed Aug. 7, 2017, and U.S. Provisional Application No. 62/608,265, filed Dec. 20, 2017, each of which is hereby incorporated by reference in its entirety. This application is related to U.S. Provisional Application No. 62/291,931, filed Feb. 5, 2016, U.S. Provisional Application No. 62/344,612, filed Jun. 2, 2016, and U.S. Provisional Application No. 62/424,792, filed Nov. 21, 2016, and International Application No. PCT/US2017/01653, filed Feb. 3, 2017, each of which is hereby incorporated by reference in its entirety.

FIELD

The disclosure generally refers to a combination of compounds to treat cancer, such as cancers with wild-type or mutated Raf or Ras.

BACKGROUND

BRAF inhibitors have been approved to treat late-stage melanoma, such as metastatic melanoma or unresectable melanoma. However, they have only been approved in melanomas that have a BRAF mutation, such as V600E or V600K. Additionally, it is well accepted that these compounds can actually worsen tumors in patients with wild-type BRAF. Furthermore, the effectiveness of these compounds is not permanent and tumors with mutant BRAF often become resistant to such treatments. It has also been found that tumors with mutant RAS (KRAS, NRAS, and/or HRAS) progress even faster when treated with these compounds. Thus, there is a need to increase the effectiveness of these compounds in tumors with wild-type and mutant BRAF and also beyond melanoma. The embodiments described herein fill these needs as well as others.

SUMMARY

Embodiments provided herein, provide methods of treating a tumor in a subject comprising administering to the subject an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein provide methods of maintaining the state of a tumor in a subject comprising administering to the subject an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein, provide methods of treating a subject with a tumor without a BRAF V600E or V600K mutation, the method comprising administering to the subject that does not have the BRAF V600E or V600K mutation an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein provide methods of treating a metastatic tumor in a subject, the method comprising administering a an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein provide methods of treating a drug resistant tumor, the method comprising administering an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein provide pharmaceutical compositions comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein provide fixed unit dosage forms comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, or a pharmaceutically acceptable salt thereof, and a DNA damaging agent.

Embodiments provided herein provide injectable pharmaceutical compositions comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein provide methods of preparing an injectable pharmaceutical composition comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent, the method comprising mixing the inhibitor, or a pharmaceutically acceptable salt thereof, and a DNA damaging agent to form an injectable pharmaceutical composition.

Embodiments provided herein provide kits comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

Embodiments provided herein provide containers comprising a pharmaceutical preparation comprising a an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof and prescribing information, wherein the prescribing information comprises instructions for administering the inhibitor with a DNA damaging agent to a subject with a tumor characterized as wild-type RAF.

BRIEF DESCRIPTION OF FIGURES

FIG. 4A: Growth rate comparisons of SK-MEL-28 and SKMEL-28VR1 cells (n=3). 100000 cells plated at time-point 0. FIG. 4B: Colony formation assays of SK-MEL-28 and SKMEL-28VR1 cells following treatments with differential doses of vemurafenib (n=5) (p<0.0001).

FIG. 5A: Unbiased Mass spectrometry: FAM129B protein abundance following differential treatments of SK-MEL-28 and SK-MEL-28VR1 cells (n=3). FIG. 5B: illustrates a characterization of SK-MEL-28VR1 cells. Western blot of PHGDH protein expression in differentially treated SK-MEL-28 and SK-MEL-28VR1 cells. Alpha tubulin used as loading control. 50 μg of protein loaded in each lane.

FIG. 6A: Colony formation assays of SKMEL-28 cells following control or PHGDH siRNAs treatments with differential doses of vemurafenib (n=3) (p=0.3052). FIG. 6B: Colony formation assays of SK-MEL-28VR1 cells following control or PHGDH siRNAs treatments with differential doses of vemurafenib (n=3) (p<0.0001). FIG. 6C: Colony formation assays of SK-MEL-28 cells following treatments with differential doses of vemurafenib+/−methotrexate (75 nM) (n=3) (p=0.9203). FIG. 6D: Colony formation assays of SK-MEL-28VR1 cells following treatments with differential doses of vemurafenib+/−methotrexate (75 nM) (n=3) (p<0.0001). FIG. 6E: illustrates the importance of serine biosynthesis pathway to vemurafenib resistance in SK-MEL-28VR1 cells. Colony formation assays of SK-MEL-28VR1 cells following treatments with differential doses of vemurafenib+/−serine in media (n=3) (p<0.0001).

FIG. 7A: Colony formation assays of SKMEL-28 cells following treatments with differential doses of vemurafenib+/−gemcitabine (50 nM) (n=3) (p<0.0001). FIG. 7B: Colony formation assays of SK-MEL-28VR1 cells following treatments with differential doses of vemurafenib+/−gemcitabine (50 nM) (n=3) (p<0.0001). FIG. 7C: Colony formation assays of SK-MEL-28 cells following control or PHGDH siRNAs treatments with differential doses of vemurafenib+/−gemcitabine (50 nM) (n=3) (p=0.9816). FIG. 7D: Colony formation assays of SK-MEL-28VR1 cells following control or PHGDH siRNAs treatments with differential doses of vemurafenib+/−gemcitabine (50 nM) (n=3) (p=0.0189). FIG. 7E: Colony formation assays of SK-MEL-28 cells following treatments with differential doses of vemurafenib+gemcitabine (50 nM)+/−methotrexate (75 nM) (n=3) (p=0.6585). FIG. 7F: Colony formation assays of SK-MEL-28VR1 cells following treatments with differential doses of vemurafenib+gemcitabine (50 nM)+/−methotrexate (75 nM) (n=3) (p<0.0001). FIG. 7G: Fa-CI plot representing synergy between gemcitabine and vemurafenib. Data points falling below the line indicate synergy between drugs. Data points represent CI calculations at specific doses. Table 3, herein, contains CI values.

FIG. 8A: Colony formation assays of BxPC3M1 cells following treatments with differential doses of gemcitabine+/−vemurafenib (1 μM) (n=3) (p<0.0001). FIG. 8B: Fa-CI plot representing synergy between gemcitabine and vemurafenib. Data points falling below the line indicate synergy between drugs. Data points represent CI calculations at specific doses. Please refer to Table 3 for CI values. FIG. 8C: Colony formation assays of NCI-H2122 cells following treatments with differential doses of gemcitabine+/−vemurafenib (1 μM) (n=3) (p<0.0001).

FIG. 9A: Cell proliferation assay of BxPC3 cells treated with vemurafenib (10 μM). 100000 cells plated on day 0. FIG. 9B: Cell proliferation assay of BxPC3M1 cells treated with vemurafenib (10 μM). 100000 cells plated on day 0. FIG. 9C: Cell proliferation assay of Panc1 cells treated with vemurafenib (10 μM). 100000 cells plated on day 0. FIG. 9D: Cell proliferation assay of MiaPaca2 cells treated with vemurafenib (10 μM). 100000 cells plated on day 0. FIG. 9E: Mass spectrometry: PHGDH protein expression in pancreatic cancer cells treated with DMSO or vemurafenib (10 μM) (n=3). FIG. 9F: Mass spectrometry: PSAT1 protein expression in pancreatic cancer cells treated with DMSO or vemurafenib (10 μM) (n=3). FIG. 9G: Mass spectrometry: PSPH protein expression in pancreatic cancer cells treated with DMSO or vemurafenib (10 μM) (n=3). FIG. 9H: Mass spectrometry: SARS protein expression in pancreatic cancer cells treated with DMSO or vemurafenib (10 μM) (n=3).

FIG. 10A: Colony formation assays of BxPC3M1 cells following treatments with differential doses of gemcitabine+/−vemurafenib (1 μM)+/−methotrexate (75 nM) (n=3) (p=0.0258). FIG. 10B: Colony formation assays of NCI-H2122 cells following treatments with differential doses of gemcitabine+/−vemurafenib (1 μM)+/−methotrexate (75 nM) (n=3) (p=0020). FIG. 10C: Colony formation assays of BxPC3M1 cells following treatments with differential doses of vemurafenib+/−serine (n=3) (p<0.0001).

FIG. 11A: Colony formation assays of BxPC3M1 cells following treatments with differential doses of gemcitabine+/−dabrafenib (1 μM) (n=3) (p<0.0001). FIG. 11B: Colony formation assays of NCI-H2122 cells following treatments with differential doses of gemcitabine+/−dabrafenib (1 μM) (n=3) (p<0.0001). FIG. 11C: Colony formation assays of BxPC3M1 cells following treatments with differential doses of dabrafenib+/−gemcitabine (50 nM) (n=3) (p<0.0001).

FIG. 14A: Normalized isobologram showing the synergistic effect of gemcitabine and vemurafenib in SK-MEL28VR1 cells. Data points that fall to the left of the line indicate synergy. Data points represent CI calculations at specific doses. (see, Table 3 for CI values). FIG. 14B: Normalized isobologram showing the synergistic effect of gemcitabine and vemurafenib in BxPC3M1 cells. Data points that fall to the left of the line indicate synergy. Data points represent CI calculations at specific doses. (see, Table 4 for CI values).

DETAILED DESCRIPTION

Figure 1A:
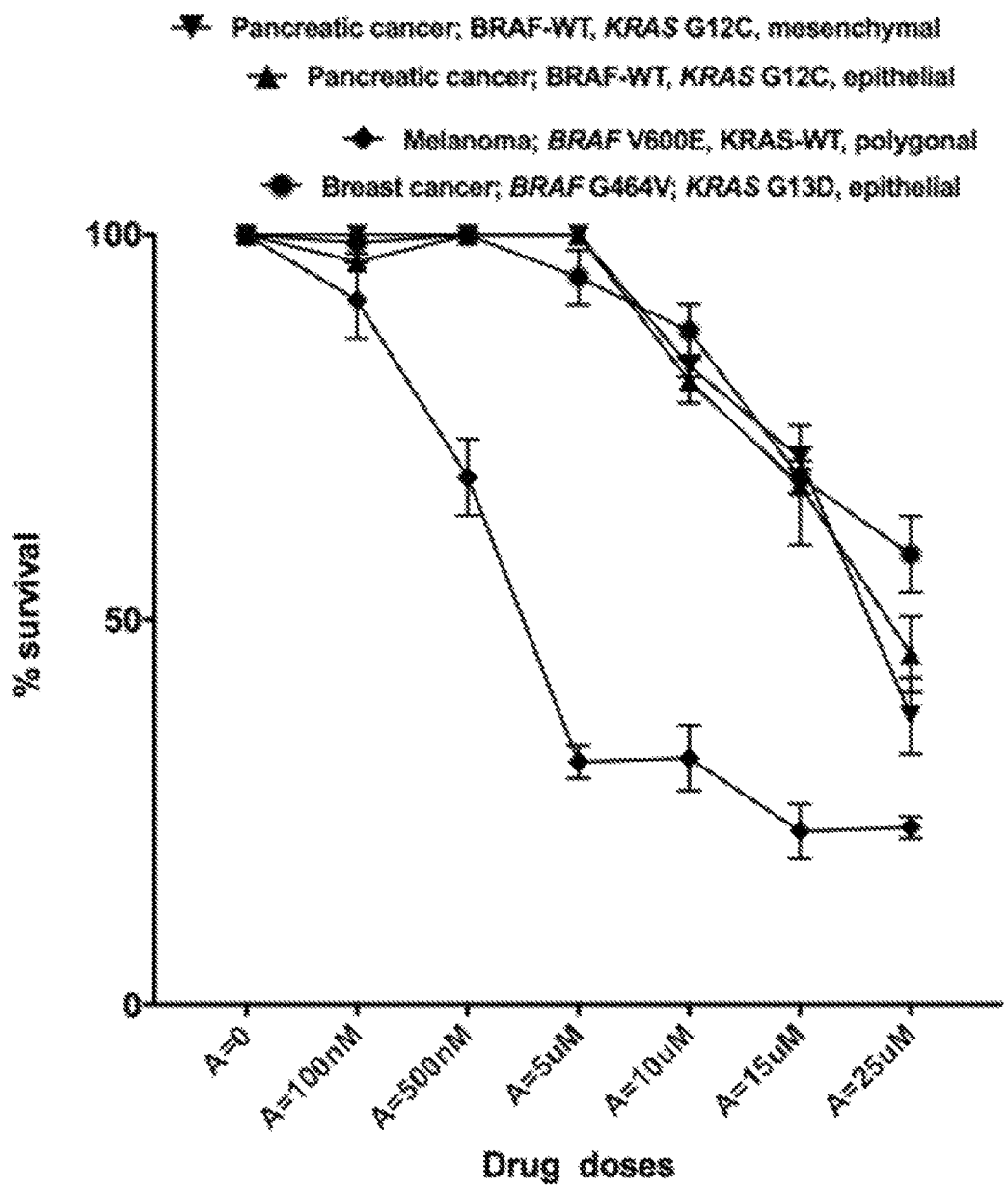
FIG. 1A and FIG. 1B illustrate 48-hour kill curves in various cancer cell lines as indicated. Drug A is vemurafenib and Drug B is gemcitabine. The mutation status of RAS and BRAF are indicated in the figures.

This application describes combinations of compounds and methods of using the same. The compounds and combinations can also be prepared as pharmaceutical compositions that can be administered in a unit dosage form or in different dosage forms.

Vemurafenib refers to a compound of Formula I, or a pharmaceutically acceptable salt thereof:

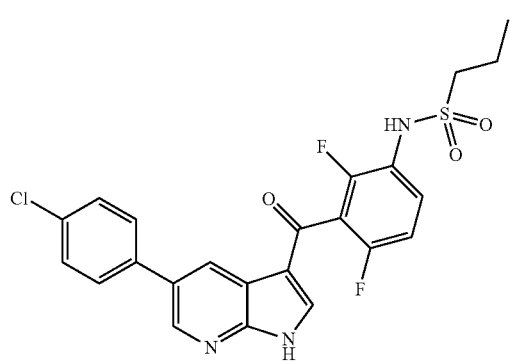

I

Dabrafenib refers to a compound of Formula II, or a pharmaceutically acceptable salt thereof:

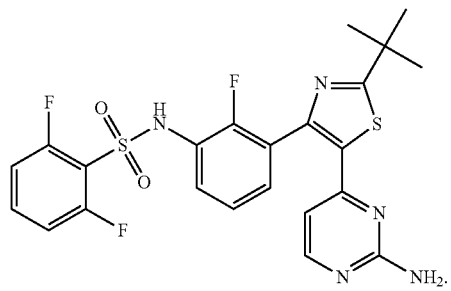

II

Encorafenib refers to a compound of Formula III, or a pharmaceutically acceptable salt thereof:

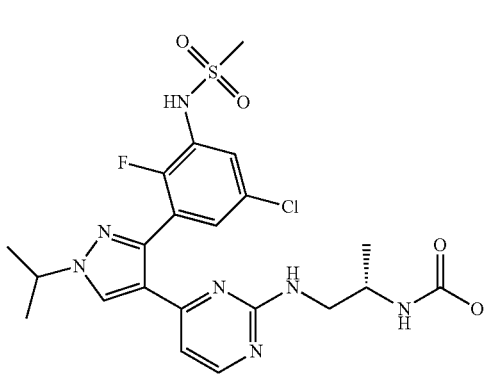

III

Sorafenib refers to a compound of Formula IV, or a pharmaceutically acceptable salt thereof:

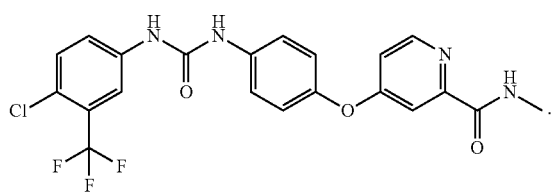

IV

Reference is made throughout the present specification BRAF inhibitors. Examples include, but are not limited to, vemurafenib, dabrafenib, or encorafenib, and pharmaceutically acceptable salts thereof. Other BRAF, CRAF, or pan-RAF inhibitors can also be substituted, such as sorafenib, RAF265, AD80, GDC0879, AZ628, ZM336372, NVPBHG712, LY3009120, TAK632, MLN2480, or XP102. Thus, for the avoidance of doubt, where vemurafenib, dabrafenib, sorafenib, encorafenib, RAF265, AD80, GDC0879, AZ628, ZM336372, NVPBHG712, LY3009120, TAK632, MLN2480, or XP102 is referenced, it is disclosed that BRAF inhibitors can be used generally or other specific types of BRAF inhibitors can also be used. This reference also shall be construed to include pharmaceutically acceptable salts of the compounds described herein. Vemurafenib, dabrafenib, encorafenib, sorafenib, RAF265, AD80, GDC0879, AZ628, ZM336372, NVPBHG712, LY3009120, TAK632, MLN2480, or XP102 or pharmaceutically acceptable salts thereof, can be combined (simultaneously or sequentially) with various cancer treating therapeutics, such as but not limited to DNA damaging agents. Examples of such DNA damaging agents include, but are not limited to, agents that cause double strand breaks (DSBs), single strand breaks, antimetabolites, DNA crosslinkers, topoisomerase inhibitors, polymerase inhibitors, or alkylating agents. In some embodiments, the DNA damaging agent is a nucleoside analog. In some embodiments, the nucleoside analog is cytosine arabinoside, fludarabine, cladribine, or gemcitabine. In some embodiments, the DNA damaging agent is gemcitabine, cytosine arabinoside, fludarabine, cladribine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, and the like. These agents can be combined with BRAF inhibitors, or a pharmaceutically acceptable salt thereof, either singularly or in combinations. In some embodiments, a BRAF inhibitor is administered in conjunction with a nucleoside analog. In some embodiments, a BRAF inhibitor is administered in conjunction with a quinoline alkaloid, such as, but not limited to, camptothecin. The administration can be performed according to the method described herein, wherein the agent may be administered before the BRAF inhibitor or as otherwise described herein. They can also be combined with MEK inhibitors, such as but not limited to trametinib and the like. In some embodiments, the MEK inhibitors can also be combined or administered with the BRAF inhibitors (e.g., vemurafenib, dabrafenib, sorafenib, encorafenib, RAF265, AD80, GDC0879, AZ628, ZM336372, NVPBHG712, LY3009120, TAK632, MLN2480, or XP102) and the DNA damaging agents as described herein. In some embodiments, the BRAF inhibitor is not administered in combination (simultaneously or sequentially) with a MEK inhibitor.

In some embodiments, the compositions or methods are combined with an additional therapeutic. In some embodiments, the additional therapeutic is a microtubule stabilizer. A non-limiting example of a microtubule stabilizer is a taxane. In some embodiments, the taxane is, but not limited to, paclitaxel, docetaxel, cabazitaxel and the like. In some embodiments, taxane is a protein-bound taxane. For example, paclitaxel can be protein-bound paclitaxel, which can also be referred to as a nanoparticle albumin-bound paclitaxel or nab-paclitaxel. One non-limiting example of a protein bound paclitaxel is Abraxane®. In some embodiment, other taxanes are bound to a protein.

The compounds, compositions, and combinations thereof can be used in any of the methods described herein, including, but not limited to, treating cancer or a tumor in a subject, such as melanoma, pancreatic cancer, lung cancer (e.g. NSCLC or SCLC), colon cancer, ovarian cancer, prostate cancer, or breast cancer.

In some embodiments, compositions, such as pharmaceutical compositions or fixed dosage forms of BRAF inhibitors (e.g. vemurafenib, dabrafenib, sorafenib, encorafenib, RAF265, AD80, GDC0879, AZ628, ZM336372, NVPBHG712, LY3009120, TAK632, MLN2480, or XP102), or a pharmaceutically acceptable salt thereof, with the DNA damaging agents are provided. The compositions can also comprise a MEK inhibitor, EGFR inhibitor or an additional therapeutic (e.g. taxanes) as described herein. In some embodiments, the compositions can be free of a MEK inhibitor, EGFR inhibitor, or an additional therapeutic. The combination of BRAF inhibitors, or pharmaceutically acceptable salts thereof, and the DNA damaging agents and uses of the combination provided herein demonstrate surprising and unexpected ability to treat cancers and other unexpected results as described herein. In some embodiments, the combinations retard tumor progression. In some embodiments, the combinations reduce tumor size. In some embodiments, the combinations re-sensitize tumors that have become resistant to BRAF, CRAF, or pan-RAF inhibitors. In some embodiments, the combinations sensitize tumors that are resistant to BRAF, CRAF, or pan-RAF inhibitors. A tumor that is re-sensitized refers to a tumor that has become resistant or is expected to become resistant to a primary treatment, such as BRAF, CRAF, or pan-RAF inhibitors (e.g. vemurafenib, dabrafenib, sorafenib, encorafenib, RAF265, AD80, GDC0879, AZ628, ZM336372, NVPBHG712, LY3009120, TAK632, MLN2480, or XP102). A tumor that is sensitized refers to a tumor that was resistant to a treatment and is now able to be treated with the treatment. For example, tumors that do not respond to BRAF inhibitors are sensitized to BRAF inhibitors when the tumor is treated with a combination of a BRAF inhibitor with a DNA damaging agent. In some embodiments, the sensitization is provided by pre-treating tumors with the DNA damaging agent with a BRAF, CRAF, or pan-RAF inhibitor. Without being bound to any particular theory, the combination of BRAF, CRAF, or pan-RAF inhibitors and the DNA damaging agent (pre-treatment or not) works synergistically as compared to either component alone. In some embodiments, BRAF, CRAF, or pan-RAF inhibitors can also be used at a lower dose than what has been used previously because of the combination with the DNA damaging agent. Non-limiting examples of such doses are described herein. The DNA damaging agent can also be used at a lower dose than is typical because it is combined with a BRAF, CRAF, or pan-RAF inhibitor. Non-limiting examples of such doses are described herein. These combinations can also be used with or without the MEK inhibitors. Examples of MEK inhibitors are described herein, but others can also be used. The combinations can also be administered in conjunction with an EGFR inhibitor. The combinations can also be administered without an EGFR inhibitor. Examples of EGFR inhibitors include, but are not limited to, cetuximab, panitumumab, zalutumumab, nimotuzumab, matuzumab, gefitinib and erlotinib. The combinations can also be administered in conjunction with or without a taxane. Non-limiting examples of taxanes are described herein. The combinations described herein can be combined into the same formulation or unit dosage form or administered separately but can still be considered being combined because they are being administered to a patient with the intent to treat the cancer with each of the therapeutics.

In some embodiments, the combination of a BRAF, CRAF, or pan-RAF inhibitor with the DNA damaging agent is used in maintenance therapy and/or secondary therapy. Maintenance therapy, or secondary therapy, refers to treating a patient with a secondary therapy who had cancer and has already been treated with a primary treatment and the tumor responded to the primary treatment. Maintenance therapy can be used to either slow the tumor's ability to grow, if not completely eliminated, or inhibit the tumor from recurring if the tumor is completely eliminated. Often maintenance therapy is used where the tumor is stable, or the patient has had a complete response (e.g. is considered in remission). However, maintenance therapy can also be used when the subject has had a partial response or simply a response to the primary therapy. The combination can also include a MEK inhibitor, EGFR inhibitor, or a taxane as described herein.

In some embodiments, methods are provided for treating cancer metastasis, the method comprising administering to the subject a BRAF, CRAF, or pan-RAF inhibitor (e.g. vemurafenib, dabrafenib, encorafenib, sorafenib, RAF265, AD80, GDC0879, AZ628, ZM336372, NVPBHG712, LY3009120, TAK632, MLN2480, and/or XP102) and a DNA damaging agent. In some embodiments, the method comprises administering a MEK inhibitor, an EGFR inhibitor, or a taxane, non-limiting examples of which are provided herein. In some embodiments, the metastatic cancer is metastatic melanoma, pancreatic cancer, lung cancer, colon cancer, ovarian cancer, prostate cancer, or breast cancer. In some embodiments, the methods comprise administering the DNA damaging agent before the BRAF inhibitor similar or the same as other embodiments described herein.

Cancers (tumors) often become resistant to treatments due to selection pressures from the treatments themselves. Thus, a treatment such as a BRAF, CRAF, or pan-RAF inhibitor can initially work, but then stop working after a period of time due to developing resistance. This resistance can be overcome or lessened by administering a BRAF, CRAF, or pan-RAF inhibitor with a DNA damaging agent described herein. Accordingly, in some embodiments, methods of treating a resistant cancer are provided. In some embodiments, the method comprising administering to a subject with a treatment resistant cancer a BRAF, CRAF, or pan-RAF inhibitor and a DNA damaging agent. Examples of which are described herein. In some embodiments, the cancer is resistant to vemurafenib, dabrafenib, sorafenib, encorafenib, RAF265, AD80, GDC0879, AZ628, ZM336372, NVPBHG712, LY3009120, TAK632, MLN2480, and/or XP102. In some embodiments, the method comprises administering the therapeutics with a MEK inhibitor, an EGFR inhibitor, and/or a taxane, or any combination thereof, non-limiting examples of which are provided herein. In some embodiments, the methods comprise administering the DNA damaging agent before the BRAF, CRAF, or pan-RAF inhibitor similar or the same as other embodiments described herein.

Pharmaceutical Compositions/Formulations

Pharmaceutical compositions can be formulated by standard techniques using one or more physiologically acceptable carriers or excipients. The formulations may contain a buffer and/or a preservative. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the compound, chosen route of administration and standard biological practice.

Pharmaceutical compositions can include effective amounts of one or more compound(s) described herein together with, for example, pharmaceutically acceptable diluents, preservatives, solubilizers, emulsifiers, adjuvants and/or other carriers. Such compositions may include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes. Hyaluronic acid may also be used. Such compositions can be employed to influence the physical state, stability, rate of in vivo release, and rate of in vivo clearance of a compound described herein. See, e.g., Remington's Pharmaceutical Sciences, 18th Ed. (1990, Mack Publishing Co., Easton, Pa. 18042) pages 1435-1712 which are herein incorporated by reference. The compositions can, for example, be prepared in liquid form, or can be in dried powder, such as lyophilized form. Particular methods of administering such compositions are described infra.

Where a buffer is to be included in the formulations described herein, the buffer can be selected from sodium acetate, sodium carbonate, citrate, glycylglycine, histidine, glycine, lysine, arginine, sodium dihydrogen phosphate, disodium hydrogen phosphate, sodium phosphate, and tris (hydroxymethyl)-aminomethane, or mixtures thereof. The buffer can also be glycylglycine, sodium dihydrogen phosphate, disodium hydrogen phosphate, and sodium phosphate or mixtures thereof.

Where a pharmaceutically acceptable preservative is to be included in a formulation of one of the compounds described herein, the preservative can be selected from phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof.

The preservative is present in a concentration from about 0.1 mg/ml to about 50 mg/ml, in a concentration from about 0.1 mg/ml to about 25 mg/ml, or in a concentration from about 0.1 mg/ml to about 10 mg/ml.

The use of a preservative in pharmaceutical compositions is well-known to the skilled person. For convenience reference is made to Remington: The Science and Practice of Pharmacy, 19th edition, 1995.

The formulation may further comprise a chelating agent where the chelating agent may be selected from salts of ethlenediaminetetraacetic acid (EDTA), citric acid, and aspartic acid, and mixtures thereof.

The chelating agent can be present in a concentration from 0.1 mg/ml to 5 mg/ml, from 0.1 mg/ml to 2 mg/ml or from 2 mg/ml to 5 mg/ml.

The use of a chelating agent in pharmaceutical compositions is well-known to the skilled person. For convenience reference is made to Remington: The Science and Practice of Pharmacy, 19th edition, 1995.

The formulation of the compounds described herein may further comprise a stabilizer selected from high molecular weight polymers and low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, and threonine or any mixture thereof. The stabilizer can also be L-histidine, imidazole or arginine.

The high molecular weight polymer can be present in a concentration from 0.1 mg/ml to 50 mg/ml, from 0.1 mg/ml to 5 mg/ml, from 5 mg/ml to 10 mg/ml, from 10 mg/ml to 20 mg/ml, from 20 mg/ml to 30 mg/ml or from 30 mg/ml to 50 mg/ml.

The low molecular weight compound can be present in a concentration from 0.1 mg/ml to 50 mg/ml, from 0.1 mg/ml to 5 mg/ml, from 5 mg/ml to 10 mg/ml, from 10 mg/ml to 20 mg/ml, from 20 mg/ml to 30 mg/ml or from 30 mg/ml to 50 mg/ml.

The use of a stabilizer in pharmaceutical compositions is well-known to the skilled person. For convenience reference is made to Remington: The Science and Practice of Pharmacy, 19th edition, 1995.

The formulation of the compounds described herein may further include a surfactant. In some embodiments, the surfactant may be selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (e.g. oleic acid and caprylic acid), acylcarnitines and derivatives, $N_\alpha$-acylated derivatives of lysine, arginine or histidine, or side-chain acylated derivatives of lysine or arginine, $N_\alpha$-acylated derivatives of dipeptides comprising any combination of lysine, arginine or histidine and a neutral or acidic amino acid, $N_\alpha$-acylated derivative of a tripeptide comprising any combination of a neutral amino acid and two charged amino acids, or the surfactant may be selected from the group of imidazoline derivatives, or mixtures thereof.

The use of a surfactant in pharmaceutical compositions is well-known to the skilled person. For convenience reference is made to Remington: The Science and Practice of Pharmacy, 19th edition, 1995.

Pharmaceutically acceptable sweeteners can be part of the formulation of the compounds described herein. Pharmaceutically acceptable sweeteners include at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), saccharin, sodium or calcium saccharin, and optionally a bulk sweetener such as sorbitol, mannitol, fructose, sucrose, maltose, isomalt, glucose, hydrogenated glucose syrup, xylitol, caramel, and honey.

Intense sweeteners are conveniently employed in low concentrations. For example, in the case of sodium saccharin, the concentration may range from 0.04% to 0.1% (w/v) based on the total volume of the final formulation or is about 0.06% in the low-dosage formulations and about 0.08% in the high-dosage ones. The bulk sweetener can effectively be used in larger quantities ranging from about 10% to about 35%, or from about 10% to 15% (w/v).

The formulations of the compounds described herein may be prepared by conventional techniques, e.g. as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

The phrase "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. As used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

Administration of the compounds described herein may be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration. A pharmaceutical composition of the compounds described herein can be for administration for injection, or for oral, pulmonary, nasal, transdermal, ocular administration.

For oral administration, the pharmaceutical composition of the compounds described herein can be formulated in unit dosage forms such as capsules or tablets. The tablets or capsules may be prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound. In some embodiments, the unit dosage form can be formulated as a combination product that comprises both a BRAF inhibitor and one or more of the DNA damaging agents. In some embodiments, the unit dosage form refers to one composition that comprises a BRAF inhibitor and a second composition that comprises one or more of the DNA damaging agents. If multiple DNA damage agents are used then the same number of unit dosage forms can be prepared and used.

For parenteral administration, the compounds described herein are administered by either intravenous, subcutaneous, or intramuscular injection, in compositions with pharmaceutically acceptable vehicles or carriers. The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

For administration by injection, the compound(s) can be used in solution in a sterile aqueous vehicle which may also contain other solutes such as buffers or preservatives as well as sufficient quantities of pharmaceutically acceptable salts or of glucose to make the solution isotonic. The pharmaceutical compositions of the compounds described herein may be formulated with a pharmaceutically acceptable carrier to provide sterile solutions or suspensions for injectable administration. Injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin. The injection formulation can comprise a combination of a BRAF inhibitor and one or more DNA damaging agents. The injection formulation can also be prepared by combining separate formulations into one. The formulations can also be administered sequentially or simultaneously or nearly simultaneously.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more-unit dosage forms containing the active ingredient. The pack can, for example, comprise metal or plastic foil, for example, a blister pack. The pack or dispenser device can be accompanied by instructions for administration.

The compounds described herein also include derivatives referred to as prodrugs, which can be prepared by modifying functional groups present in the compounds in such a way that the modifications are cleaved, either in routine manipulation or in vivo, to the parent compounds.

Dosages

The compounds described herein may be administered to a patient at therapeutically effective doses to prevent, treat, or control one or more diseases described herein, such as but not limited to, the cancers described herein. Pharmaceutical compositions comprising one or more of compounds described herein may be administered to a patient in an amount sufficient to elicit an effective therapeutic response in the patient. An amount adequate to accomplish this is defined as "therapeutically effective dose." The dose can be determined by the efficacy of the particular compound employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the LD50 (the dose lethal to 50% of the population) and the ED50 (the dose therapeutically effective in 50% of the population). The LD50 and the ED50 can be determined for the components alone or the combination. The dose ratio between toxic and therapeutic effects is the therapeutic index and can be expressed as the ratio, LD50/ED50. In some embodiments, combinations that exhibit large therapeutic indices are used. While compounds that exhibit toxic side effects can be used, care should be taken to design a delivery system that targets such compounds to the site of affected tissue to minimize potential damage to normal cells and, thereby, reduce side effects. The side effects can be avoided, in some embodiments, by using a combination of a BRAF inhibitor and one or more DNA damaging agents described herein. The side effects can be avoided or reduced by using lower doses of one or more of the therapeutics.

The data obtained from cell culture assays and animal studies can be used to formulate a dosage range for use in humans. In some embodiments, the dosage of such compounds lies within a range of circulating concentrations that include the ED50 with little or no toxicity. The dosage can vary within this range depending upon the dosage form employed and the route of administration. For any compound described herein, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

The amount and frequency of administration of the compounds described herein and/or the pharmaceutically acceptable salts thereof will be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general, it is contemplated that an effective amount would be from 0.001 mg/kg to 10 mg/kg body weight, and in particular from 0.01 mg/kg to 1 mg/kg body weight. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

In some embodiments, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, from about 0.01 mg to about 750 mg, from about 0.01 mg to about 500 mg, or from about 0.01 mg to about 250 mg, according to the particular application. In some embodiments, the amount of a BRAF, CRAF, or pan-RAF inhibitor, or a pharmaceutically acceptable salt thereof, administered to the subject is less than, about, or is, 960 mg, 720 mg, 480 mg, 240 mg, 150 mg, 100 mg, 50 mg, or 25 mg twice daily. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

In some embodiments, one or more compounds described herein are administered with another compound. The administration may be sequentially or concurrently. The combination may be in the same dosage form or administered as separate doses. In some embodiments, the first compound is a BRAF, CRAF, or pan-RAF inhibitor and the other compound is one or more DNA damaging agents. In some embodiments, the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, and the like. In some embodiments, the DNA damaging agent is administered before the BRAF, CRAF, or pan-RAF inhibitor. In some embodiments, the DNA damaging agent is administered at least, or about 10, 20, 30, 40, 50, 60, 120, 180, 240, 300, or 360 minutes before the BRAF, CRAF, or pan-RAF inhibitor. In some embodiments, the DNA damaging agent is administered at least, or about, 1, 2, 3, 4, or 5 days before the BRAF, CRAF, or pan-RAF inhibitor. In some embodiments, the DNA damaging agent is administered to the subject prior to a MEK inhibitor or a taxane is administered to the subject. In some embodiments, the DNA damaging agent is administered at least, or about 10, 20, 30, 40, 50, 60, 120, 180, 240, 300, or 360 minutes before the MEK inhibitor or the taxane. In some embodiments, the DNA damaging agent is administered at least, or about, 1, 2, 3, 4, or 5 days before the MEK inhibitor or the taxane.

In some embodiments, the amount of the BRAF, CRAF, or pan-RAF inhibitor can be from about 1 mg to about 100 mg, from about 5 mg to about 100 mg, from about 10 mg to about 100 mg, from about 25 mg to about 100 mg, from about 50 mg to about 100 mg, or from about 75 mg to about 100 mg. In some embodiments, the amount of a BRAF inhibitor can be from about 1 mg to about 80 mg, from about 1 mg to about 60 mg, from about 1 mg to about 40 mg, from about 1 mg to about 20 mg, or from about 1 mg to about 10 mg. In some embodiments, the amount of a BRAF, CRAF, or pan-RAF inhibitor can be from about 5 mg to about 80 mg. In some embodiments, the amount of a BRAF inhibitor is from about 5 mg to about 240 mg. In some embodiments, the DNA damaging agent is administered in dose of, about, or less than 1250 mg/m$^2$, 1000 mg/m$^2$, 800 mg/m$^2$, 600 mg/m$^2$, 400 mg/m$^2$, 200 mg/m$^2$, 100 mg/m$^2$, or 50 mg/m$^2$, 25 mg/m$^2$, 10 mg/m$^2$, or 5 mg/m$^2$ or any range in between. In some embodiments, the dose of the DNA damaging agent is considered a sublethal dose for the patient or subject.

The compounds described herein can also be administered with anti-nausea agents, which can also be referred to as anti-emetics. Examples of such agents include, but are not limited to, dolasetron, granisetron, ondansetron, tropisetron, palonosetron, mirtazapine, aprepitant, casopitant, and the like.

Medical Use

The compositions described herein may be useful for treating cancer. Examples of such cancers include, but are not limited to, as melanoma, pancreatic cancer, lung cancer, colon cancer, ovarian cancer, prostate cancer, and breast cancer. In some embodiments, the tumor is negative for a BRAF mutation. In some embodiments, the tumor is wild-type BRAF. In some embodiments, the tumor has a mutation in BRAF. In some embodiments, the tumor has a BRAF V600E mutation. In some embodiments, the tumor is free of a BRAF V600E mutation. In some embodiments, the tumor has a BRAF V600K mutation. In some embodiments, the tumor is free of a BRAF V600K mutation. In some embodiments, the tumor has a RAS (e.g. KRAS, NRAS, and/or HRAS) mutation. In some embodiments, the RAS mutation is G12C, G12D, G12V, or G13D. In some embodiments, the tumor is free of a RAS mutation. In some embodiments, the tumor is wild-type RAS. For the avoidance of doubt, the term "RAS" can refer to KRAS, NRAS, and/or HRAS. In some embodiments, the RAS is KRAS. In some embodiments, the RAS is NRAS. In some embodiments, the RAS is HRAS.

In some embodiments, the tumor is analyzed for mutations prior to administering a combination of a BRAF inhibitor and one or more DNA damaging agents. In some embodiments, the tumor is analyzed for a BRAF V600E mutation. In some embodiments, the tumor is analyzed for a BRAF V600K mutation. In some embodiments, the tumor is analyzed for a RAS G12C mutation. In some embodiments, the tumor is analyzed for a RAS G12D mutation. In some embodiments, the tumor is analyzed for a RAS G12V mutation. In some embodiments, the tumor is analyzed for a RAS G13D mutation. In some embodiments, the patient is only treated with a combination of a BRAF, CRAF, or pan-RAF inhibitor and the DNA damaging agent if no mutation in BRAF is found. In some embodiments, the patient is only treated with a combination of a BRAF, CRAF, or pan-RAF inhibitor and the DNA damaging agent if a mutation in BRAF is found. In some embodiments, the patient is only treated with a combination of a BRAF inhibitor and the DNA damaging agent if no mutation in RAS is found. In some embodiments, the patient is only treated with a combination of a BRAF inhibitor and the DNA damaging agent if a mutation in RAS is found.

In some embodiments, methods of treating cancer are provided. In some embodiments, the cancer is melanoma, pancreatic cancer, lung cancer (e.g. NSCLC or SCLC), colon cancer, ovarian cancer, prostate cancer, or breast cancer. In some embodiments, the cancer is metastatic cancer that originated as one of the cancers described herein. Accordingly, as described herein, methods of treating metastatic cancer are provided.

In some embodiments, the methods described herein comprise administering a combination of a BRAF, CRAF, or pan-RAF inhibitor and one or more DNA damaging agents as described herein. In some embodiments, the BRAF, CRAF, or pan-RAF inhibitor is administered to the subject simultaneously with the one or more DNA damaging agents or sequentially (before or after) the one or more DNA damaging agents. In some embodiments, the method comprises initially administering the BRAF, CRAF, or pan-RAF inhibitor and then before the inhibitor is completely administered administering one or more DNA damaging agents or vice versa. Such administration can be referred to as overlapping the therapeutics. In some embodiments, the combination is also administered with a MEK inhibitor or an EGFR inhibitor as described herein. The compounds can be administered in any order, these are simply examples only and are not intended to be limiting. In some embodiments, the subject is administered a DNA damaging agent as described herein prior to being treated with the BRAF, MEK inhibitors, and/or taxanes. In some embodiments, the subject is administered, gemcitabine, methotrexate, or pyrimethamine (or other DNA damaging agent described herein) in first step and then subsequently the subject is administered the BRAF, CRAF, or pan-RAF inhibitor, the MEK inhibitor, and/or the taxane. This can also be referred to as pre-treatment. Accordingly, in some embodiments, the subject is pre-treated with a DNA damaging agent before a BRAF, CRAF, or pan-RAF inhibitor is administered to the subject. In some embodiments, the time between the administration of the DNA damaging agent and the BRAF inhibitor and/or MEK inhibitor and/or the taxane is about, or at least, 1, 2, 3, 4, 5, 6, 7, 8, 9, 10, 11, 12, 16, 18, 20, or 24 hours. In some embodiments, the time between the administration of the DNA damaging agent and the BRAF, CRAF, or pan-RAF and/or MEK inhibitor and/or the taxane is about, or at least, 1-24, 1-18, 1-12, 1-8, 1-6, 1-4, 4-12, 4-16, 4-20, 4-24, 8-12, 8-16, 8-20, 8-24, 12-16, 12-18, 12-24, 16-20, 16-24, or 20-24 hours. In some embodiments, the BRAF, CRAF, or pan-RAF and/or MEK inhibitor and/or taxane is administered 1-10 days after the DNA damaging agent is administered. In some embodiments, the BRAF, CRAF, or pan-RAF and/or MEK inhibitor and/or taxane is administered about, or at least, 1-10 days after the DNA damaging agent is administered. In some embodiments, the BRAF, CRAF, or pan-RAF and/or MEK and/or taxane inhibitor is administered about, or at least, 1, 2, 3, 4, 5, 6, 7, 8, 9, or after the DNA damaging agent is administered. This protocol can be repeated as necessary, such as, and only for example, 1, 2, 3, 4, 5, 6, 7, or 8 times. In some embodiments, the subject is not administered a MEK inhibitor. In some embodiments, the BRAF inhibitor is administered without a MEK inhibitor and/or a taxane. In some embodiments, the BRAF inhibitor is administered free of a MEK inhibitor and/or a taxane. In some embodiments, the BRAF inhibitor is administered in the absence of a MEK inhibitor and/or a taxane. In some embodiments, a pharmaceutical composition comprising the BRAF inhibitor is free of a MEK inhibitor and/or a taxane.

In some embodiments, the methods described herein comprise detecting a BRAF and/or RAS mutation in the subject's tumor and treating the subject with a combination of a BRAF inhibitor and one or more DNA damaging agents in the subject that does not have a BRAF and/or RAS mutation. The methods of treatment and order of administration of the different active ingredients can be performed according to any method described herein. This can be done, for example, to ensure that the patient will benefit from the treatment. However, there is no requirement that they specifically be tested for such mutation. In some embodiments, the mutation that is not detected is BRAF V600E or V600K. In some embodiments, a subject with a BRAF and/or RAS mutation is treated with combinations described herein. In some embodiments, the subject that is treated has a tumor that is wild-type BRAF and mutated RAS. In some embodiments, the mutant RAS comprises a mutation described herein. In some embodiments, the subject that is treated has a tumor with a mutated BRAF and a mutated RAS. In some embodiments, the mutations of each are those that are described herein. In some embodiments, the subject that is treated has a tumor with a mutated BRAF and a wild-type RAS. The mutations can be any mutation, such as those described herein. The mutations present in the tumor can be detected by any method, such as PCR, RT-PCR, genomic sequencing, RNA sequencing, northern blot, southern blot, western blot, or any other molecular technique that can be used to detect mutations in BRAF and/or RAS. The specific method of detecting mutations in BRAF and/or RAS is not critical. The mutation can be detected in any tumor sample. The tumor sample can be obtained through, for example, a biopsy. A blood sample may also be used to identify the mutation status of the tumor. The sample and the technique for detecting the presence or absence of a mutation is not critical to the methods described herein.

In some embodiments, methods of treating a drug resistant tumor are provided. In some embodiments, the methods comprise administering a BRAF, CRAF, or pan-RAF inhibitor, or a pharmaceutically acceptable salt thereof, and a DNA damaging agent. In some embodiments, the drug resistant tumor is resistant to treatment consisting of a BRAF, CRAF, or pan-RAF inhibitor. In some embodiments, the drug resistant tumor is a metastatic tumor. In some embodiments, the metastatic tumor is a metastatic melanoma, metastatic pancreatic tumor, metastatic lung tumor, metastatic colon tumor, metastatic ovarian tumor, metastatic prostate tumor, metastatic lung tumor, or metastatic breast tumor. In some embodiments, the drug resistant tumor is a melanoma, pancreatic tumor, lung tumor, colon tumor, ovarian tumor, prostate tumor, lung tumor, or breast tumor.

In some embodiments, the drug resistant tumor is characterized as wild-type BRAF. In some embodiments, the drug resistant tumor is characterized as mutant BRAF. In some embodiments, the mutant BRAF is BRAF V600E or V600K.

In some embodiments, the drug resistant tumor is characterized as wild-type RAS. In some embodiments, the drug resistant tumor is characterized as mutant RAS. In some embodiments, the method of treating a drug resistant tumor further comprises detecting the presence or absence of a BRAF V600E or V600K mutation in a tumor sample derived from the subject prior to the administering step. In some embodiments, the methods comprise detecting the presence or absence of a RAS mutation in a tumor sample derived from the subject prior to the administering step. The BRAF, CRAF, or pan-RAF inhibitor can be any such inhibitor described herein.

In some embodiments, the DNA damaging agent is any one described herein. In some embodiments, it is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof. In some embodiments, the DNA damaging agent is gemcitabine, methotrexate and/or pyrimethamine.

As described herein, in some embodiments, the combinations described herein can be administered by any suitable route, including, but not limited to, via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the compound, chosen route of administration and standard practice.

Embodiments provided herein also provided for kits. In some embodiments, the kits comprise a pharmaceutical composition comprising a BRAF, CRAF, or pan-RAF inhibitor, or a pharmaceutically acceptable salt thereof, and a pharmaceutical composition comprising a DNA damaging agent. In some embodiments, one pharmaceutical composition comprises both. In some embodiments, they are separate pharmaceutical compositions. In some embodiments, the kits comprise a first pharmaceutically acceptable container comprising the BRAF, CRAF, or pan-RAF inhibitor and a second pharmaceutically acceptable container comprising the DNA damaging agent. In some embodiments, the containers are sterile and pyrogen free. In some embodiments, the kits comprise prescribing information. In some embodiments, the prescribing information comprises instructions for administering the BRAF, CRAF, or pan-RAF inhibitor and the DNA damaging agent to a subject with a tumor characterized as wild-type BRAF and/or mutant BRAF. In some embodiments, the prescribing information comprises instructions for administering the BRAF inhibitor and the DNA damaging agent to a subject with a tumor characterized as wild-type RAS or mutant RAS.

Embodiments provided herein also provide for containers comprising a pharmaceutical composition comprising a BRAF, CRAF, or pan-RAF inhibitor and prescribing information, wherein the prescribing information comprises instructions for administering the BRAF, CRAF, or pan-RAF inhibitor with a DNA damaging agent to a subject with a tumor characterized as wild-type RAF. In some embodiments, the tumor is a melanoma tumor. In some embodiments, the container comprises a capsule, tablet, or other oral dosage form comprising the BRAF inhibitor. In some embodiments, the BRAF inhibitor is vemurafenib, dabrafenib, encorafenib, or sorafenib, or a pharmaceutically acceptable salt thereof. In some embodiments, the DNA damaging is an agent that cause double strand breaks (DSBs), single strand breaks, an antimetabolite, a DNA crosslinker, a topoisomerases inhibitor, a polymerase inhibitor, or an alkylating agent. In some embodiments, the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof. In some embodiments, the instructions further provide for administering to the subject an EGFR inhibitor or a MEK inhibitor or a taxane such as, but not limited to, those described herein.

Definitions

Unless otherwise defined, all technical and scientific terms used herein have the same meaning as commonly understood by one of ordinary skill in the art. Although methods and materials similar or equivalent to those described herein can be used in the practice or testing of the compositions and compounds described herein, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the compositions and compounds described herein will be apparent from the following detailed description and claims.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

By "pharmaceutical formulation" it is further meant that the carrier, solvent, excipients and salt must be compatible with the active ingredient of the formulation (e.g. a compound described herein). It is understood by those of ordinary skill in this art that the terms "pharmaceutical formulation" and "pharmaceutical composition" are generally interchangeable, and they are so used for the purposes of this application.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic. The present disclosure includes pharmaceutically acceptable salts of any compound (s) described herein.

Pharmaceutically acceptable salts can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile, and the like. Lists of suitable salts are found in *Remington's Pharmaceutical Sciences,* 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.) the compounds described herein can be delivered in prodrug form and can be administered in this form for the treatment of disease. "Prodrugs" are intended to include any covalently bonded carriers that release an active parent drug of described herein in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds described herein wherein a hydroxy, amino, or sulfhydryl group is bonded to any group that, when the prodrug is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds described herein.

As used herein, "treating" or "treatment" includes any effect e.g., lessening, reducing, modulating, or eliminating, that results in the improvement of the condition, disease, disorder, etc. "Treating" or "treatment" of a disease state means the treatment of a disease-state in a mammal, particularly in a human, and include: (a) inhibiting an existing disease-state, i.e., arresting its development or its clinical symptoms; and/or (c) relieving the disease-state, i.e., causing regression of the disease state.

As used herein, "mammal" or "subject" refers to human and non-human patients. In some embodiments, the subject is a subject in need thereof. The term "subject" and "patient" can be used interchangeably. As used herein, a patient that is "in need thereof" is a subject that has been identified as needing the treatment or suspected of needing the treatment. For example, a subject that has been diagnosed with cancer can be considered a subject in need thereof. Traditionally, a subject with no BRAF mutation would not be considered a subject in need thereof for a BRAF, CRAF, or pan-RAF inhibitor because it is contraindicated against such treatment. However, the combinations described herein of the BRAF inhibitors and one or more DNA damaging agents can change that same subject to a subject in need thereof because of the ability for the combination to sensitize such BRAF wild-type tumors to a BRAF, CRAF, or pan-RAF inhibitor treatment.

As used herein, the term "therapeutically effective amount" refers to a compound, or a combination of compounds, described herein present in or on a recipient in an amount sufficient to elicit biological activity, e.g. pain relief. In some embodiments, the combination of compounds is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased decrease in pain, or some other beneficial effect of the combination compared with the individual components.

All percentages and ratios used herein, unless otherwise indicated, are by weight.

Throughout the description, where compositions are described as having, including, or comprising specific components, or where processes are described as having, including, or comprising specific process steps, it is contemplated that compositions described herein also consist essentially of, or consist of, the recited components, and that the processes described herein also consist essentially of, or consist of, the recited processing steps. Further, it should be understood that the order of steps or order for performing certain actions are immaterial so long as the process remains operable. Moreover, two or more steps or actions can be conducted simultaneously.

As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. Thus, for example, a reference to "a host cell" includes a plurality of such host cells, and a reference to "an antibody" is a reference to one or more antibodies and equivalents thereof known to those skilled in the art, and so forth.

The compounds described herein can be prepared according to known methods.

In some embodiments, embodiments provided herein also include, but are not limited to:

1. A method of treating a tumor in a subject comprising administering to the subject a DNA damaging agent and an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof.

2. The method of embodiment 1, wherein the inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

3. The method of embodiments 1 or 2, wherein the DNA damaging agent is an agent that cause double strand breaks (DSBs), single strand breaks, an antimetabolite, a DNA crosslinker, a topoisomerases inhibitor, a polymerase inhibitor, nucleoside analog, or an alkylating agent.

4. The method of embodiment 3, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

5. The method of embodiment 3, wherein the DNA damaging agent is gemcitabine, methotrexate, camptothecin, and/or pyrimethamine, or a pharmaceutically acceptable salt thereof.

6. The method of embodiment 1, wherein the inhibitor, or a pharmaceutically acceptable salt thereof, and the DNA damaging agent is administered sequentially, simultaneously, or in an overlapping manner.

7. The method of embodiment 1, wherein the DNA damaging agent is administered to the subject prior to the inhibitor being administered to the subject.

8. The method of embodiment 1, wherein the inhibitor is administered to the subject at least 1-24 hours after the DNA damaging agent is administered to the subject.

9. The method of embodiment 1, wherein the subject is pre-treated with the DNA damaging agent before the inhibitor is administered to the subject.

10. The method of embodiment 1, wherein the inhibitor, or a pharmaceutically acceptable salt thereof, and the DNA damaging agent is administered orally.

11. The method of embodiment 1, wherein the inhibitor, or a pharmaceutically acceptable salt thereof, and the DNA damaging agent is administered intravenously.

12. The method of embodiment 1, wherein the inhibitor, or a pharmaceutically acceptable salt thereof, is administered orally and the DNA damaging agent is administered intravenously.

13. The method of embodiment 1, wherein the inhibitor, or a pharmaceutically acceptable salt thereof, is administered intravenously and the DNA damaging agent is administered orally.

14. The method of any one of embodiments 3-13, wherein the inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

15. The method of embodiment 1, wherein the tumor is a pancreatic tumor, melanoma tumor, lung tumor, colon cancer tumor, ovarian tumor, prostate tumor, or breast tumor.

16. The method of embodiment 1, wherein the tumor is a pancreatic tumor.

17. The method of embodiment 1, wherein the tumor is a melanoma tumor.

18. The method of embodiment 1, wherein the tumor is a metastatic tumor.

19. The method of embodiment 1, wherein the tumor is characterized as wild-type BRAF.

20. The method of embodiment 1, wherein the tumor is characterized as wild-type RAS.

21. The method of embodiment 1, wherein the tumor is characterized as mutant BRAF.

22. The method of embodiment 1, wherein the tumor is characterized as mutant BRAF V600E or V600K.

23. The method of embodiment 1, wherein the tumor is characterized as mutant RAS.

24. The method of embodiment 1, wherein the tumor is characterized as wild-type BRAF and mutant RAS.

25. The method of embodiment 1, wherein the tumor is characterized as mutant BRAF and wild-type RAS.

26. The method of embodiment 1, wherein the subject is administered a dose of the inhibitor, or a pharmaceutically acceptable salt thereof, that is about or less than 960 mg, 720 mg, 480 mg, 240 mg, 150 mg, 100 mg, 50 mg, or 25 mg twice daily.

27. The method of embodiment 1, wherein the DNA damaging agent is administered at a dose of about or less than 1250 mg/m$^2$, 1000 mg/m$^2$, 800 mg/m$^2$, 600 mg/m$^2$, 400 mg/m$^2$, 200 mg/m$^2$, 100 mg/m$^2$, or 50 mg/m$^2$, 25 mg/m$^2$, 10 mg/m$^2$, or 5 mg/m$^2$.

28. The method of embodiment 1, wherein the DNA damaging agent is administered daily, twice a week, three times a week, four times a week, five times a week, weekly, every two weeks, every three weeks, or monthly.

29. The method of embodiments 27 or 28, wherein the DNA damaging agent is a double strand break DNA damaging agent, or a pharmaceutically acceptable salt thereof.

30. The method of embodiment 29, wherein the DNA damaging agent is gemcitabine, methotrexate, camptothecin, or pyrimethamine, or a pharmaceutically acceptable salt thereof.

31. The method of embodiment 1, further comprising administering a MEK inhibitor or a taxane.

32. The method of embodiment 31, wherein the MEK inhibitor or the taxane is administered to the subject after the DNA damaging agent is administered to the subject.

33. The method of any one of embodiments 2-30, further comprising administering a MEK inhibitor or a taxane.

34. The method of embodiment 31, wherein the MEK inhibitor is trametinib or the taxane is paclitaxel or protein bound paclitaxel or other taxane described herein.

35. The method of any one of embodiments 1-27, further comprising administering an EGFR inhibitor.

36. The method of embodiment 28, wherein the EGFR inhibitor is cetuximab, panitumumab, zalutumumab, nimotuzumab, matuzumab, gefitinib or erlotinib.

37. The method of embodiment 1, wherein the tumor size is reduced in the subject.

38. The method of embodiment 37, wherein the tumor size is reduced about 10, 20, 30, 40, 50, 60, 70, 80, 90, or 100%.

39. The method of embodiment 1, wherein the tumor does not increase in size after treatment.

40. A method of maintaining the state of a tumor in a subject comprising administering to the subject an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

41. The method of embodiment 40, wherein the DNA damaging agent is administered to the subject prior to the inhibitor being administered to the subject.

42. The method of embodiment 40, wherein the inhibitor is administered to the subject at least 1-24 hours after the DNA damaging agent is administered to the subject.

43. The method of embodiment 40, wherein the subject is pre-treated with the DNA damaging agent before the inhibitor is administered to the subject.

44. The method of embodiment 40, wherein the tumor does not recur in the subject.

45. The method of embodiment 40, wherein the tumor does not increase in size in the subject.

46. The method of embodiment 40, wherein the subject has been treated for a melanoma tumor, pancreatic tumor, lung tumor, colon tumor, ovarian tumor, or prostate tumor prior to being administered the inhibitor, or a pharmaceutically acceptable salt thereof, and the DNA damaging agent.

47. The method of embodiment 40, wherein the subject with the tumor has been previously treated with the inhibitor, or a pharmaceutically acceptable salt thereof, with or without a DNA damaging agent.

48. The method of embodiment 40, wherein the tumor is characterized as wild-type BRAF.

49. The method of embodiment 40, wherein the tumor is characterized as mutant BRAF.

50. The method of embodiment 40, wherein the tumor is characterized as mutant BRAF is V600E or V600K.

51. The method of embodiment 40, wherein the tumor is characterized as wild-type RAS.

52. The method of embodiment 40, wherein the tumor is characterized as mutant RAS.

53. The method of any one of embodiments 40-52, wherein the inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

54. The method of any one of embodiments 40-53, wherein the DNA damaging agent is an agent that cause double strand breaks (DSBs), single strand breaks, an antimetabolite, a DNA crosslinker, a topoisomerases inhibitor, a polymerase inhibitor, or an alkylating agent.

55. The method of embodiment 54, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

56. The method of any one of embodiments 40-55, further comprising administering a MEK inhibitor, an EGFR inhibitor, a taxane, or any combination thereof.

57. A method of treating a subject with a tumor without a BRAF V600E or V600K mutation, the method comprising administering to the subject that does not have the BRAF V600E or V600K mutation an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

58. The method of embodiment 57, wherein the inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

59. The method of embodiments 57, wherein the DNA damaging agent is an agent that causes double strand breaks (DSBs), single strand breaks, an antimetabolite, a DNA crosslinker, a topoisomerases inhibitor, a polymerase inhibitor, a nucleoside analog, or an alkylating agent.

60. The method of embodiment 59, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

61. The method of any one of embodiments 57-60, further comprising administering a MEK inhibitor, an EGFR inhibitor, or a taxane, or any combination thereof.

62. The method of any one of embodiments 57-61, further comprising detecting the presence or absence of a BRAF V600E or V600K mutation in a tumor sample derived from the subject prior to the administering step.

63. The method of any one of embodiments 57-62, wherein the tumor without the BRAF V600E or V600K mutation does not have a RAS mutation or wherein the tumor without the BRAF V600E or V600K mutation comprises a RAS mutation.

64. The method of any one of embodiments 57-63, further comprising detecting the presence or absence of the RAS mutation or the BRAF mutation.

65. The method of embodiment 57, wherein the DNA damaging agent is administered to the subject prior to the inhibitor being administered to the subject.

66. The method of embodiment 57, wherein the inhibitor is administered to the subject at least 1-24 hours after the DNA damaging agent is administered to the subject.

67. The method of embodiment 57, wherein the subject is pre-treated with the DNA damaging agent before the inhibitor is administered to the subject.

68. The method of embodiment 57, wherein the tumor is a pancreatic tumor or a melanoma tumor.

69. A method of treating a metastatic tumor in a subject, the method comprising administering an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

70. The method of embodiment 69, wherein the metastatic tumor is a metastatic melanoma, metastatic pancreatic tumor, metastatic lung tumor, metastatic colon tumor, metastatic ovarian tumor, metastatic prostate tumor, or metastatic breast tumor.

71. The method of embodiments 69, wherein the tumor is characterized as wild-type BRAF.

72. The method of embodiments 69, wherein the tumor is characterized as mutant BRAF.

73. The method of embodiment 72, wherein the mutant BRAF is BRAF V600E or V600K.

74. The method of any one of embodiments 69, wherein the tumor is characterized as wild-type RAS.

75. The method of any one of embodiments 69, wherein the tumor is characterized as mutant RAS.

76. The method of any one of embodiments 69-75, further comprising detecting the presence or absence of a BRAF V600E or V600K mutation in a tumor sample derived from the subject prior to the administering step.

77. The method of any one of embodiments 69-76, further comprising detecting the presence or absence of a RAS mutation in a tumor sample derived from the subject prior to the administering step.

78. The method of any one of embodiments 69-77, wherein the inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

79. The method of any one of embodiments 69-78, wherein the DNA damaging agent is an agent that causes double strand breaks (DSBs), single strand breaks, an antimetabolite, a DNA crosslinker, a topoisomerases inhibitor, a polymerase inhibitor, or an alkylating agent.

80. The method of embodiment 79, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

81. The method of any one of embodiments 69-80, further comprising administering to the subject an EGFR inhibitor, a MEK inhibitor, or a taxane, or any combination thereof.

82. The method of embodiment 69, wherein the DNA damaging agent is administered to the subject prior to the inhibitor being administered to the subject.

83. The method of embodiment 69, wherein the inhibitor is administered to the subject at least 1-24 hours after the DNA damaging agent is administered to the subject.

84. The method of embodiment 69, wherein the subject is pre-treated with the DNA damaging agent before the BRAF inhibitor is administered to the subject.

85. A method of treating a drug resistant tumor, the method comprising the method comprising administering an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

86 The method of embodiment 85, wherein the drug resistant tumor is resistant to treatment consisting of the inhibitor.

87. The method of embodiment 86, wherein the drug resistant tumor is a metastatic tumor.

88. The method of embodiment 87, wherein the metastatic tumor is a metastatic melanoma, metastatic pancreatic tumor, metastatic lung tumor, metastatic colon tumor, metastatic ovarian tumor, metastatic prostate tumor, metastatic lung tumor, or metastatic breast tumor.

89. The method of embodiment 85, wherein the drug resistant tumor is a melanoma, pancreatic tumor, lung tumor, colon tumor, ovarian tumor, prostate tumor, lung tumor or breast tumor.

90. The method of embodiment 85, wherein the tumor is characterized as wild-type BRAF.

91. The method of embodiment 85, wherein the tumor is characterized as mutant BRAF.

92. The method of embodiment 91, wherein the mutant BRAF is BRAF V600E or V600K.

93. The method of embodiment 85, wherein the tumor is characterized as wild-type RAS.

94. The method of embodiment 85, wherein the tumor is characterized as mutant RAS.

95. The method of embodiment 85, further comprising detecting the presence or absence of a BRAF V600E or V600K mutation in a tumor sample derived from the subject prior to the administering step.

96. The method of clam 85, further comprising detecting the presence or absence of a RAS mutation in a tumor sample derived from the subject prior to the administering step.

97. The method of embodiment 85, wherein the inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

98. The method of embodiment 85, wherein the DNA damaging agent is an agent that causes double strand breaks (DSBs), single strand breaks, an antimetabolite, a DNA crosslinker, a topoisomerases inhibitor, a polymerase inhibitor, a nucleoside analog, or an alkylating agent.

99. The method of embodiment 98, wherein the DNA damaging agent is gemcitabine, 5-FU, cytarabine, methotrexate, pyrimethamine, bleomycin, oxaliplatin, cisplatin, etoposide, doxorubicin, vinorelbin, mitoxantrone, podophyllotoxin, aphidicolin, fotemustine, carmustine, 5-23906, S39, SN-38, topotecan, camptothecin, rebeccamycin, or any pharmaceutically acceptable salt thereof.

100. The method of embodiment 85, wherein the DNA damaging agent is administered to the subject prior to inhibitor being administered to the subject.

101. The method of embodiment 85, wherein the inhibitor is administered to the subject at least 1-24 hours after the DNA damaging agent is administered to the subject.

102. The method of embodiment 85, wherein the subject is pre-treated with the DNA damaging agent before the inhibitor is administered to the subject.

103. A pharmaceutical composition comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

104. The pharmaceutical composition of embodiment 103, wherein the DNA damaging agent is a double strand break agent.

105. The pharmaceutical composition of embodiment 103, wherein the DNA damaging agent is gemcitabine, methotrexate, or pyrimethamine, or a pharmaceutically acceptable salt thereof.

106. The pharmaceutical composition of embodiment 103, wherein the pharmaceutical composition is suitable for oral delivery.

107. The pharmaceutical composition of embodiment 103, wherein the pharmaceutical composition is suitable for injection.

108. The pharmaceutical composition of embodiment 103, further comprising a MEK inhibitor and/or an EGFR inhibitor and/or a taxane, or any combination thereof.

109. A fixed unit dosage form comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

110. The fixed unit dosage form of embodiment 109, wherein the form comprises 150 mg, 240 mg, or less than or about 150 mg or about 240 mg of the inhibitor.

111. The fixed unit dosage form of embodiment 109, wherein the form comprises about 5 to about 200 mg of the inhibitor.

112. The fixed unit dosage form of embodiment 109, wherein inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

113. The fixed unit dosage form of embodiment 109, wherein the DNA damaging agent is an agent that causes double strand breaks (DSBs), single strand breaks, an antimetabolite, a DNA crosslinker, a topoisomerases inhibitor, a polymerase inhibitor, a nucleoside analog, or an alkylating agent.

114. The fixed unit dosage form of embodiment 113, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

115. The fixed unit dosage form of embodiment 113, wherein the DNA damaging agent is present in an amount of about or less than 1250 mg/m$^2$, 1000 mg/m$^2$, 800 mg/m$^2$, 600 mg/m$^2$, 400 mg/m$^2$, 200 mg/m$^2$, 100 mg/m$^2$, or 50 mg/m$^2$, 25 mg/m$^2$, 10 mg/m$^2$, or 5 mg/m$^2$.

116. The fixed unit dosage form of embodiment 109 wherein the fixed unit dosage form comprises a EGFR inhibitor or a MEK inhibitor or a taxane or is free of a EGFR inhibitor or a MEK inhibitor or a taxane.

117. An injectable pharmaceutical composition comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

118. The injectable pharmaceutical composition of embodiment 117, wherein the composition comprises 150 mg, 240 mg, or less than or about 150 mg or about 240 mg of the inhibitor.

119. The injectable pharmaceutical composition of embodiment 117, wherein the composition comprises about 5 to about 200 mg of the inhibitor.

120. The injectable pharmaceutical composition of embodiment 117, wherein the inhibitor is vemurafenib, dabrafenib, encorafenib, sorafenib, RAF265, AD80, GDC0879, AZ628, ZM336372, NVPBHG712, LY3009120, TAK632, MLN2480, and/or XP102 or a pharmaceutically acceptable salt thereof.

121. The injectable pharmaceutical composition of embodiment 117, wherein the DNA damaging agent is an agent that causes double strand breaks (DSBs), single strand breaks, an antimetabolite, a DNA crosslinker, a topoisomerases inhibitor, a polymerase inhibitor, or an alkylating agent.

122. The injectable pharmaceutical composition of embodiment 117, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

123. The injectable pharmaceutical composition of embodiment 117, wherein the DNA damaging agent is present in an amount of about or less than 1250 mg/m$^2$, 1000 mg/m$^2$, 800 mg/m$^2$, 600 mg/m$^2$, 400 mg/m$^2$, 200 mg/m$^2$, 100 mg/m$^2$, or 50 mg/m$^2$, 25 mg/m$^2$, 10 mg/m$^2$, or 5 mg/m$^2$.

124. The injectable pharmaceutical composition of embodiment 117, wherein the composition form comprises an EGFR inhibitor or a MEK inhibitor or a taxane or is free of an EGFR inhibitor or a MEK inhibitor or a taxane.

125. The injectable pharmaceutical composition of embodiment 117, wherein the DNA damaging agent is gemcitabine, methotrexate, or pyrimethamine.

126. A method of preparing an injectable pharmaceutical composition comprising a an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent, the method comprising mixing the inhibitor, or a pharmaceutically acceptable salt thereof, and a DNA damaging agent to form an injectable pharmaceutical composition.

127. The method of embodiment 126, wherein the wherein the BRAF inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

128. The method of embodiment 126, wherein the DNA damaging agent is an agent that causes double strand breaks (DSBs), single strand breaks, an antimetabolite, a DNA crosslinker, a topoisomerases inhibitor, a polymerase inhibitor, a nucleoside analog, or an alkylating agent.

129. The method of embodiment 126, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

130. A kit comprising a an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and a DNA damaging agent.

131. The kit of embodiment 130, comprising a first pharmaceutically acceptable container comprising the inhibitor and a second pharmaceutically acceptable container comprising the DNA damaging agent.

132. The kit of embodiment 130, wherein the containers are sterile and pyrogen free.

133. The kit of embodiment 130, further comprising prescribing information.

134. The kit of embodiment 133, wherein the prescribing information comprises instructions for administering the inhibitor and the DNA damaging agent to a subject.

135. The kit of embodiment 133 wherein the prescribing information comprises instructions for administering the inhibitor and the DNA damaging agent to a subject with a tumor characterized as wild-type RAF.

136. The kit of embodiment 133, wherein the prescribing information comprises instructions for administering the DNA damaging agent to the subject before administering the inhibitor.

137. A container comprising a pharmaceutical preparation comprising an inhibitor selected from the group consisting of: BRAF inhibitor, a BRAF inhibitor that is specific for a DFG-out (inactive) conformation of a BRAF inhibitor, a CRAF inhibitor, and a pan-RAF inhibitor, or a pharmaceutically acceptable salt thereof, and prescribing information, wherein the prescribing information comprises instructions for administering the inhibitor with a DNA damaging agent to a subject with a tumor characterized as wild-type RAF.

138. The container of embodiment 137, wherein tumor is a melanoma tumor.

139. The container of embodiment 137, comprising a capsule, tablet, or other oral dosage form comprising the inhibitor.

140. The container of any one of embodiments 137-139, wherein the inhibitor is vemurafenib, dabrafenib, encorafenib, sorafenib, RAF265, AD80, GDC0879, AZ628, ZM336372, NVPBHG712, LY3009120, TAK632, MLN2480, or XP102, or a pharmaceutically acceptable salt thereof.

141. The container of any one of embodiments 137-139, wherein the DNA damaging is an agent that causes double strand breaks (DSBs), single strand breaks, an antimetabolite, a DNA crosslinker, a topoisomerases inhibitor, a polymerase inhibitor, a nucleoside analog, or an alkylating agent.

142. The container of embodiment 141, wherein the DNA damaging agent is gemcitabine, 5-FU, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, S-23906, S39, SN-38, topotecan, camptothecin, rebeccamycin, or any pharmaceutically acceptable salt thereof.

143. The container of embodiment 137, further comprising an EGFR inhibitor or a MEK inhibitor or a taxane or wherein the container is free of a EGFR inhibitor or a MEK inhibitor or taxane.

EXAMPLES

The following examples are illustrative, but not limiting, of the methods and compositions described herein. Other suitable modifications and adaptations of the variety of conditions and parameters normally encountered in therapy and that are obvious to those skilled in the art are within the spirit and scope of the compounds and methods described herein.

Example 1: Gemcitabine Enhances the Therapeutic Effect of Vemurafenib

Figure 1B:
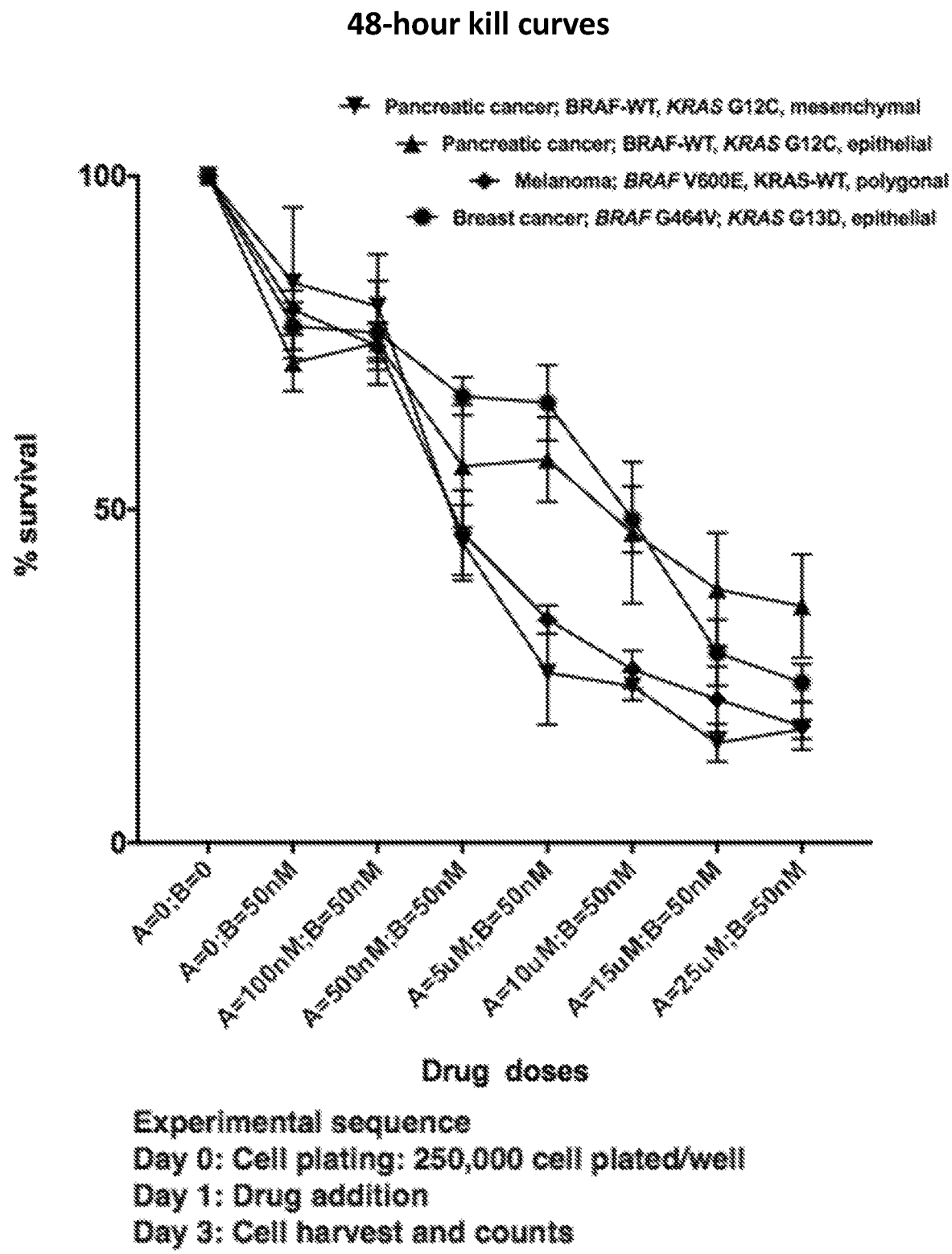

Cells were plated at approximately 250,000 cell per well. Approximately 24 hours later, the compounds were administered alone or in combination as shown in FIGS. 1A and 1B. Approximately 48 hours later, the cells were harvested either treated with both agents simultaneously or sequentially, i.e. either gemcitabine first followed by vemurafenib or vemurafenib first followed by gemcitabine. After the agents were washed from the cells, the cells were allowed to form colonies. The cells were fixed (concentrated methanol) and stained with 0.4% crystal violet in 20% ethanol and the colonies were quantified by reading absorbance at 595 nm. The results as illustrated in the following table show that the sequential addition of gemcitabine followed by vemurafenib led to reduced colony formation as compared to simultaneous treatment or where vemurafenib (Drug A) was added prior to the gemcitabine (Drug B).

TABLE 1

Simultaneous and sequential addition of Drug B and Drug A (n = 3)

| Drug doses A (uM) | BxPC3 A + B (50 nm) sim (24 hrs) avg % colony inhibition | standard deviation | BxPC3 A + B (50 nm) seq avg % colony inhibition | standard deviation | BxPC3 B (50 nm) + A seq avg % colony inhibition | standard deviation |
|---|---|---|---|---|---|---|
| 0 | 0 | 0.0 | 0 | 0.0 | 0 | 0.0 |
| 0.1 | 22.65 | 6.6 | 5.30 | 1.7 | 5.50 | 1.4 |
| 0.5 | 1 | 1.4 | 5.35 | 5.6 | 3.50 | 1.4 |
| 2 | 0 | 0.0 | 2.15 | 0.2 | 1.75 | 2.5 |
| 5 | 0 | 0.0 | 10.25 | 3.2 | 5.95 | 2.1 |
| 10 | 0 | 0.0 | 14.45 | 1.5 | 71.10 | 2.0 |

| Drug doses A (uM) | HD A + B (50 nm) sim (24 hrs) avg % colony inhibition | standard deviation | HD A + B (50 nm) seq avg % colony inhibition | standard deviation | HD B (50 nm) + A seq avg % colony inhibition | standard deviation |
|---|---|---|---|---|---|---|
| 0 | 0 | 0.0 | 0 | 0.0 | 33.25 | 4.6 |
| 0.1 | 0 | 0.0 | 15.25 | 3.9 | 37.75 | 5.3 |
| 0.5 | 0 | 0.0 | 7.75 | 4.6 | 28.25 | 5.3 |
| 2 | 0 | 0.0 | 32.00 | 7.8 | 41.25 | 1.8 |
| 5 | 5.50 | 7.8 | 52.50 | 2.8 | 84.75 | 3.9 |
| 10 | 9.50 | 5.7 | 81.25 | 6.0 | 93.75 | 2.5 | and counted. FIGS. 1A and 1B illustrates the synergistic effect of vemurafenib (Drug A) and gemcitabine (Drug B). The surprising results were the combination of the compounds were effective even in cell types that are wild-type BRAF.

Figure 2A:
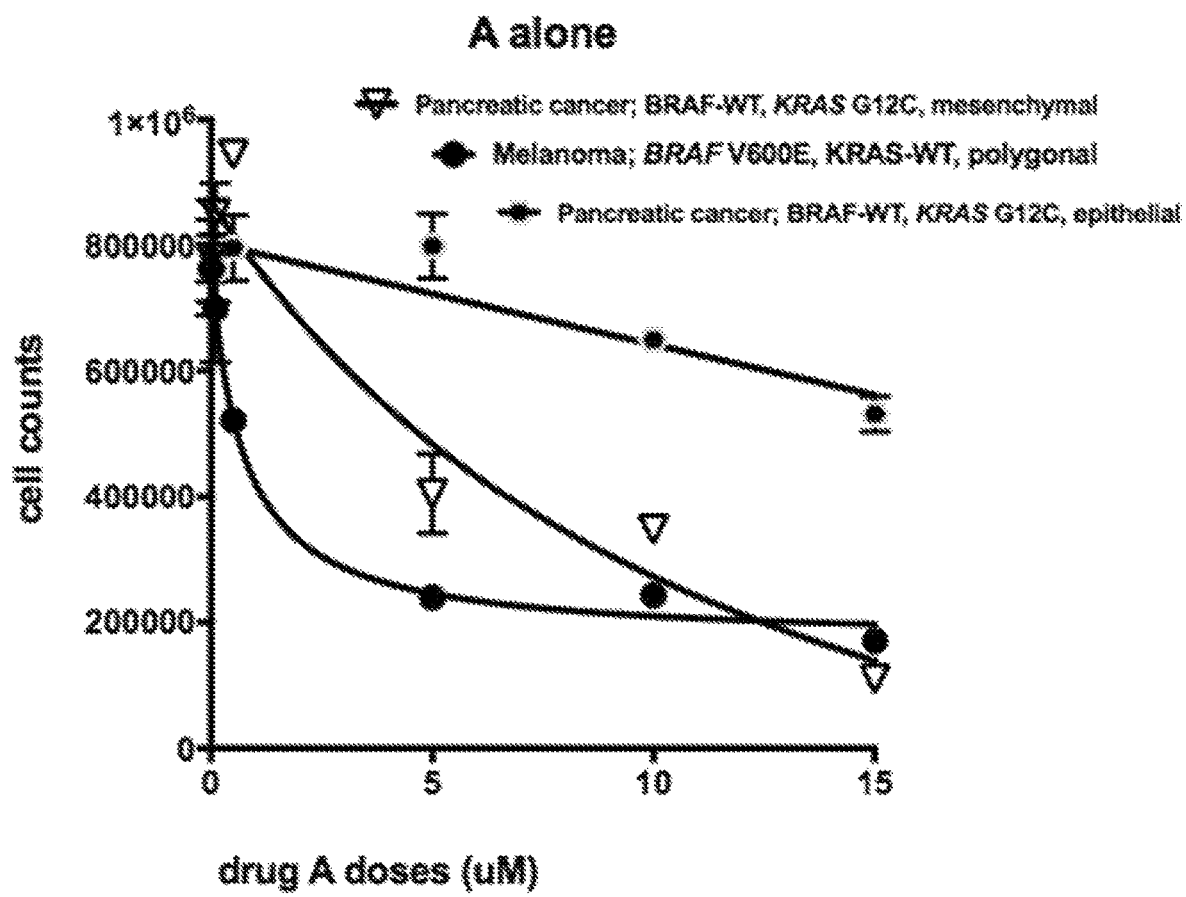
FIG. 2A and FIG. 2B illustrate 48 hr kill curves (Non-linear regression), which shows a 100 fold increase in sensitivity with the combination treatment of vemurafenib and gemcitabine in the mesenchymal pancreatic cancer cell line with WT-BRAF and KRAS-G12C mutation. Drug A is vemurafenib and Drug B is gemcitabine. The mutation status of RAS and BRAF are indicated in the figures.
Figure 2B:
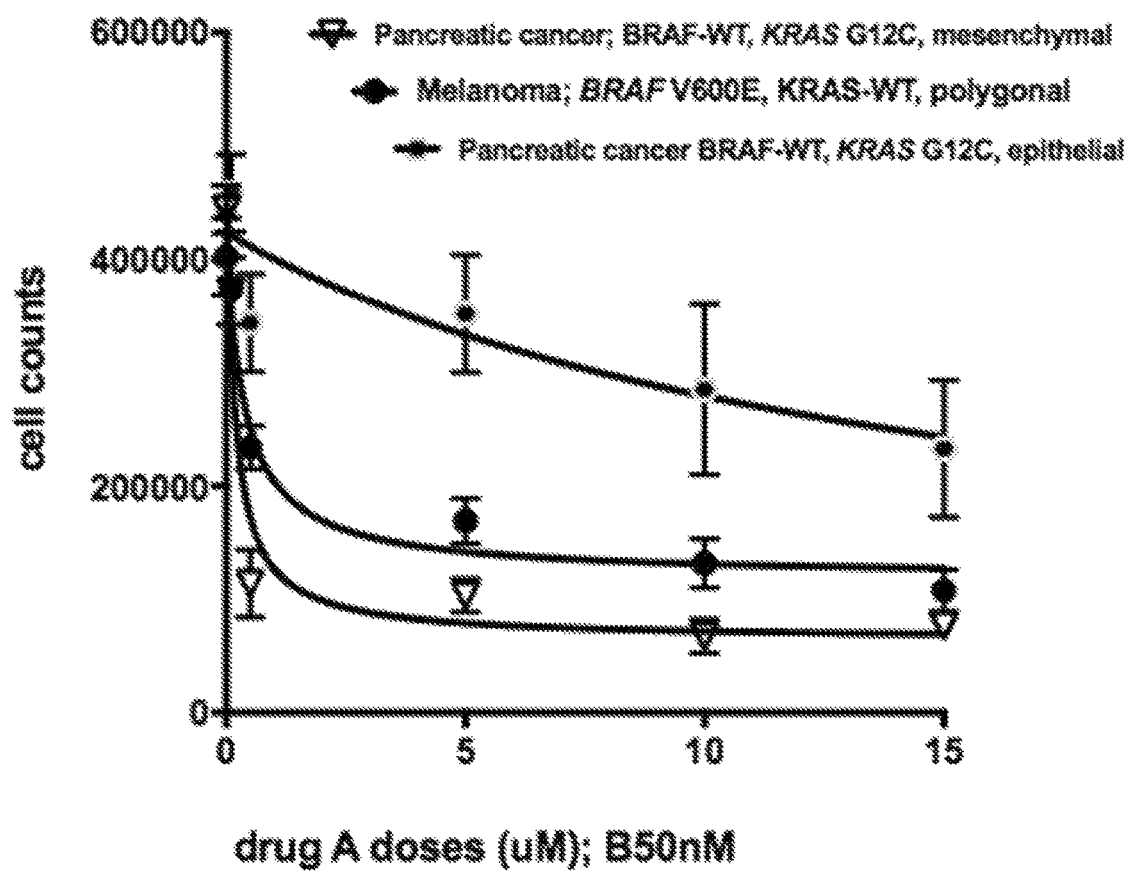

FIGS. 2A and 2B illustrate the combination of vemurafenib and gemcitabine increasing the sensitivity of cells to vemurafenib by approximately 100 times. The cells are derived from an adenocarcinoma that have wild-type BRAF. Therefore, it would not have been expected that vemurafenib would be effective in killing the cells. However, it was found that when vemurafenib (Drug A) when combined with gemcitabine (Drug B) the cells became sensitized and responded to the vemurafenib therapy. As can be seen in FIGS. 1A, 1B, 2A and 2B, the result was not observed when each agent was used alone, but only when used in combination. The combination was also able to use a lower amount of one or more of each compound to achieve significant cell killing. The combination also inhibited colony formation better than either compound alone and in a synergistic amount. (data not shown).

Figure 3A:
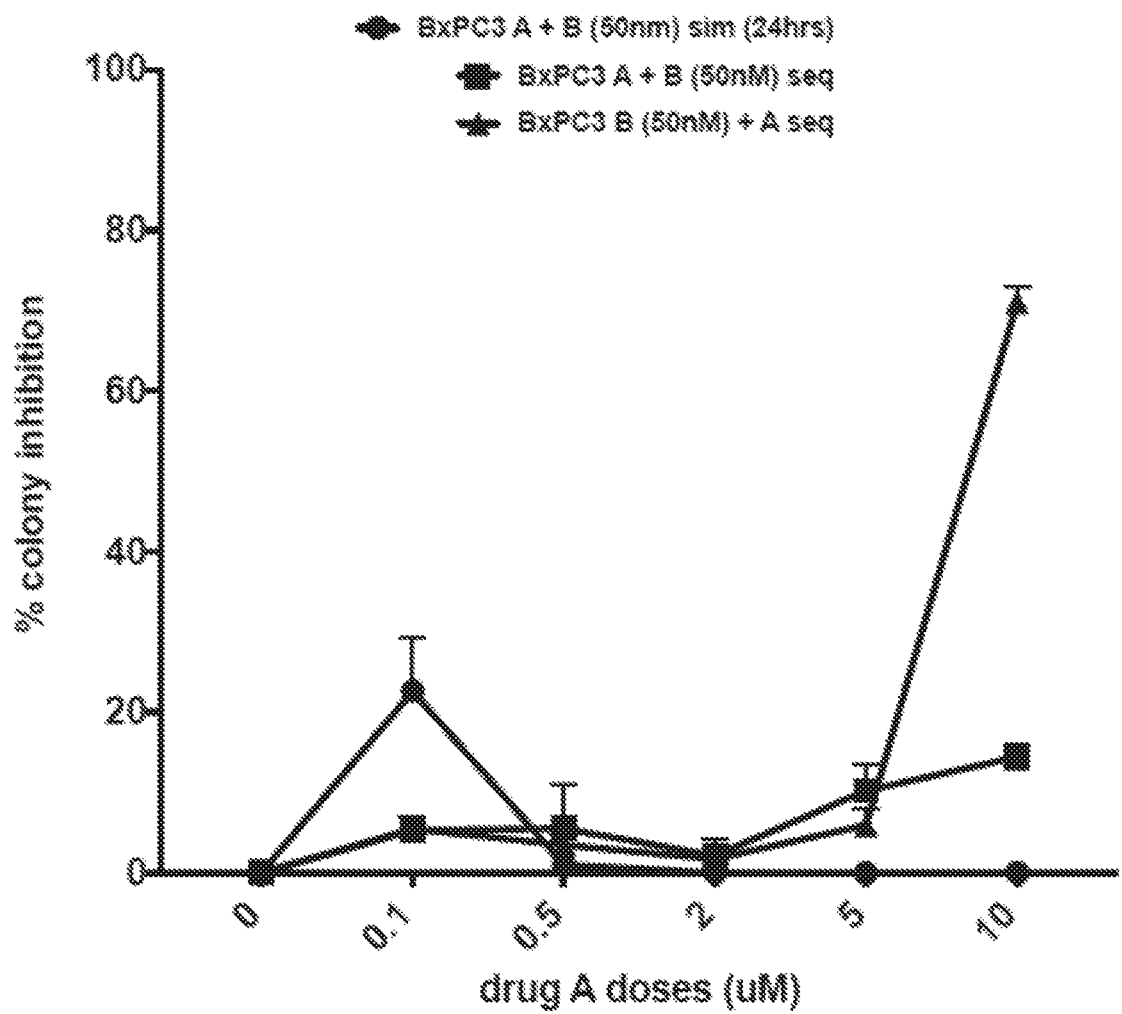
FIG. 3A and FIG. 3B illustrate % colony inhibition of vemurafenib and gemcitabine treatment as described herein.
Figure 3B:
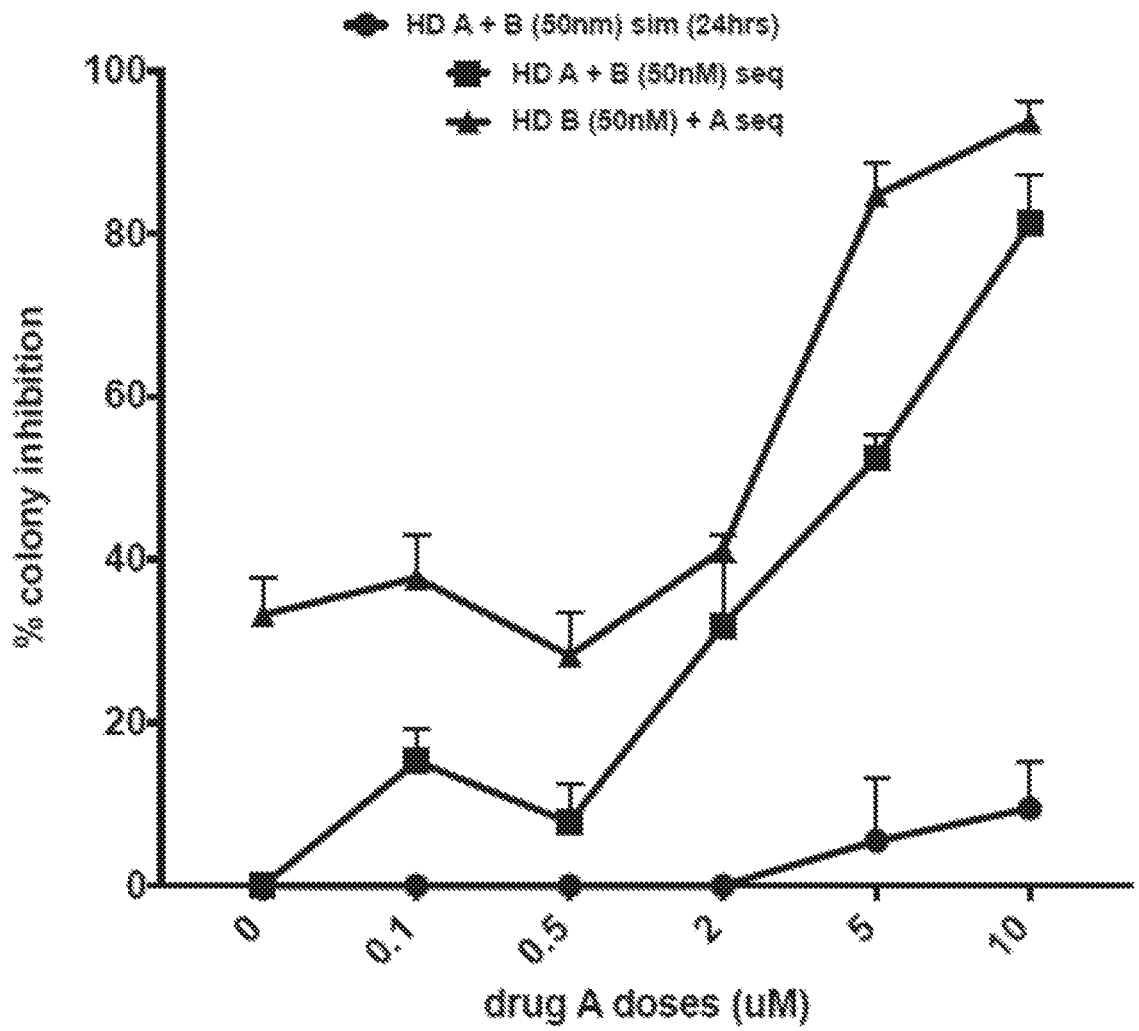

A metastatic cancer cell line (HD, also known as BxPC3M1) with wild-type BRAF and mutant KRAS (G12C) and a cancer cell line (BxPC3) with wild-type BRAF and wild-type RAS were treated with gemcitabine and vemurafenib under various conditions. The cells were These results are also illustrated in FIGS. 3A and 3B.

Without being bound to any particular theory it is believed that this result is due to priming WT BRAF/mutant KRAS cells with sublethal doses of DNA damaging agents that cause the cells to arrest in S-phase (Gemcitabine), or if other DNA damaging agents were used in G2 phase (doxorubicin, etoposide), or in G1 phase (methotrexate) and then the addition of vemurafenib, or other BRAF inhibitors such as those disclosed herein, following cell cycle arrest activates the MAPK pathway and the arrested cells attempt to proliferate with damaged unreplicated DNA. The cells then cannot survive and die. Without the priming of the cells using the DNA damaging agents, the BRAF inhibitors normally activate the MAPK pathway and leads to enhanced proliferation of the tumor cells with wild-type BRAF, which is contradindicated on the labels of the BRAF inhibitors.

These results are surprising in view of the label for vemurafenib, and other BRAF inhibitors, which instructs clinicians to confirm evidence of BRAF V600E mutation in tumor specimens prior to treatment of vemurafenib because of the deleterious effect that using such inhibitors in wild-type BRAF tumors can have. Therefore, it would not have been expected that vemurafenib would have been effective in the cell types treated and that the effect of vemurafenib would not have been synergistically been enhanced by combining it with a DNA damaging agents, such as gemcitabine, a nucleoside analog that causes double strand breaks. The ability to kill the cells was regardless of KRAS mutation, which was also surprising and unexpected because of previous evidence indicating that vemurafenib was not effective in KRAS mutated tumors.

Figure 4A:
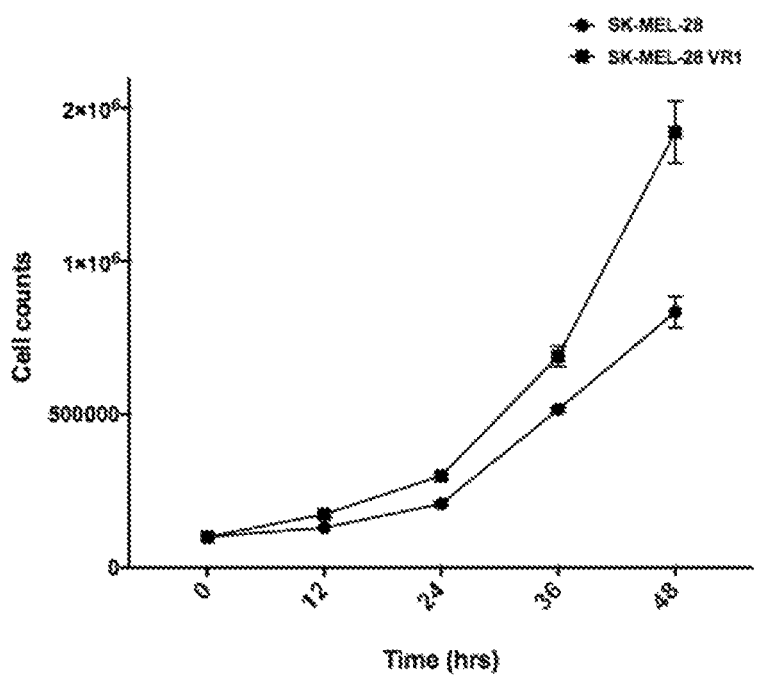
FIG. 4A and FIG. 4B illustrate a characterization of SK-MEL-28VR1 cells.
Figure 4B:
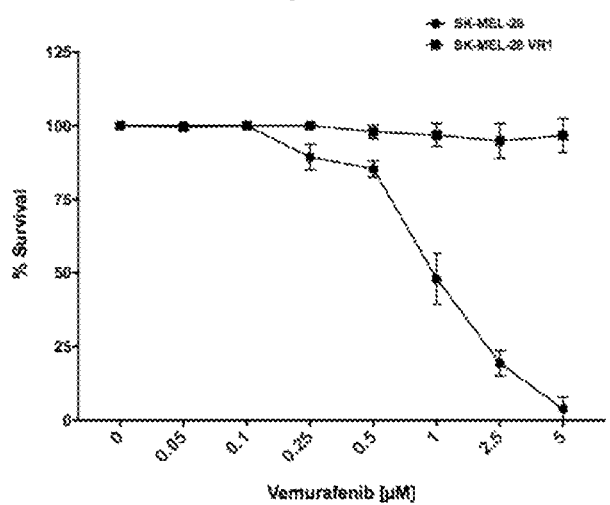

Example 2: Identification and Characterization of Vemurafenib Resistant SK-MEL-28VR1 Cells SK-MEL-28 vemurafenib resistant cell line was isolated from SK-MEL-28 parental cells via drug selection. The proliferation rate of SK-MEL-28VR1 was also higher than the parental cell line (FIG. 4A). The SK-MEL-28VR1 cells had a doubling time of 16 hours while parental cells had a doubling time of 23.1 hours. Colony formation assays revealed that SK-MEL-28VR1 cells are resistant to vemurafenib compared to its parental cell line (FIG. 4B). The SK-MEL-28VR1 cells had an IC50 at ~30 µM of vemurafenib (data not shown) while the parental cell line had an IC50 at ~1 µM (FIG. 4B). Mass Spectrometry (MS) analysis revealed that SK-MEL-28VR1 had a different proteomic profile compared to the parental cell line in response to vemurafenib treatment. FAM129B was identified as having the third highest differential expression between SK-MEL-28VR1 cells treated with vemurafenib versus SK-MEL-28VR1 cells treated with vehicle (Table 2).

| Protein | Fold differential | Pathway(s) and protein clusters |
|---|---|---|
| SPATA20 | 12 | Unassigned |
| SBDS | 10 | Unassigned |
| FAM129B | 9 | marker for MAPK activation |
| MPHOSPH6 | 9 | rRNA processing, gene expression |
| PDLIM7 | 9 | RET signalling, axon guidance, development |
| S100A11 | 8 | neutrophil degranulation, immune system |
| ASNS | 8 | ATF4 activated genes, PERK regulated gene expression, unfolded protein response, metabolism |
| PSAT1 | 8 | metabolism, serine biosynthesis |
| CYP51A1 | 8 | regulation of cholesterol biosynthesis by SREBP, metabolism, cytochrome P450, biological oxidations |
| PPP1R7 | 8 | Unassigned |
| DUS2 | 7 | tRNA processing, gene expression |
| SARS | 6 | cytosolic tRNA aminoacylation, selenocysteine synthesis, metabolism, gene expression |
| LARS2 | 6 | mitochondrial tRNA aminoacylation, gene expression |
| PSPH | 5 | metabolism, serine biosynthesis |
| KRT19 | 5 | formation of the cornified envelope, keratinization, development |
| SARS2 | 4 | mitochondrial tRNA aminoacylation, gene expression |
| RUVBL1 | 3 | telomere extension, DNA damage recognition, DNA repair, nucleosome assembly, WNT signaling, cell cycle, metabolism, post-translational modifications, signal transduction |
| PHGDH | 2 | metabolism, serine biosynthesis |
| MRPL13 | 2 | mitochondrial translation, Organelle biogenesis and maintenance |
| TXNDC17 | 2 | Unassigned |

Table 2 describes unbiased mass spectrometry. Proteins with the largest differential expression following vemurafenib treatments between SK-MEL-28VR1 vs SK-MEL-28 cells. Identified proteins are increasing in abundance with drug treatments in SK-MEL-28VR1 cells and decreasing in abundance with drug treatments in SK-MEL-28 cells. Fold differential is a quantitative measure of increased abundance of a specific protein with vemurafenib treatments of SK-MEL-28VR1 cells compared to parental SK-MEL-28 cells.

Figure 5A:
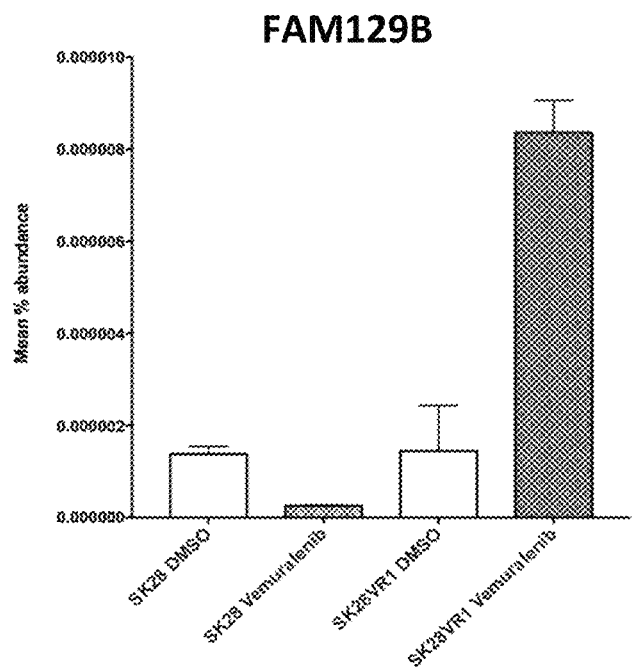
FIG. 5A and FIG. 5B illustrate a characterization of SK-MEL-28VR1 cells.

Cytoplasmic FAM129B abundance increased by ~6 fold with vemurafenib treatment compared to vehicle treatment (FIG. 5A). Interestingly, FAM129B abundance decreased in response to vemurafenib treatments in parental SK-MEL-28 cells. These trends indicated an active MAPK pathway in the SK-MEL-28VR1 cells but not in SK-MEL-28 cells. Furthermore, FAM129B protein trends supported the observed induction of cell proliferation and suggested an increase in the invasive potential of SK-MEL-28VR1 cells compared to SK-MEL-28 cells.

Figure 5B:
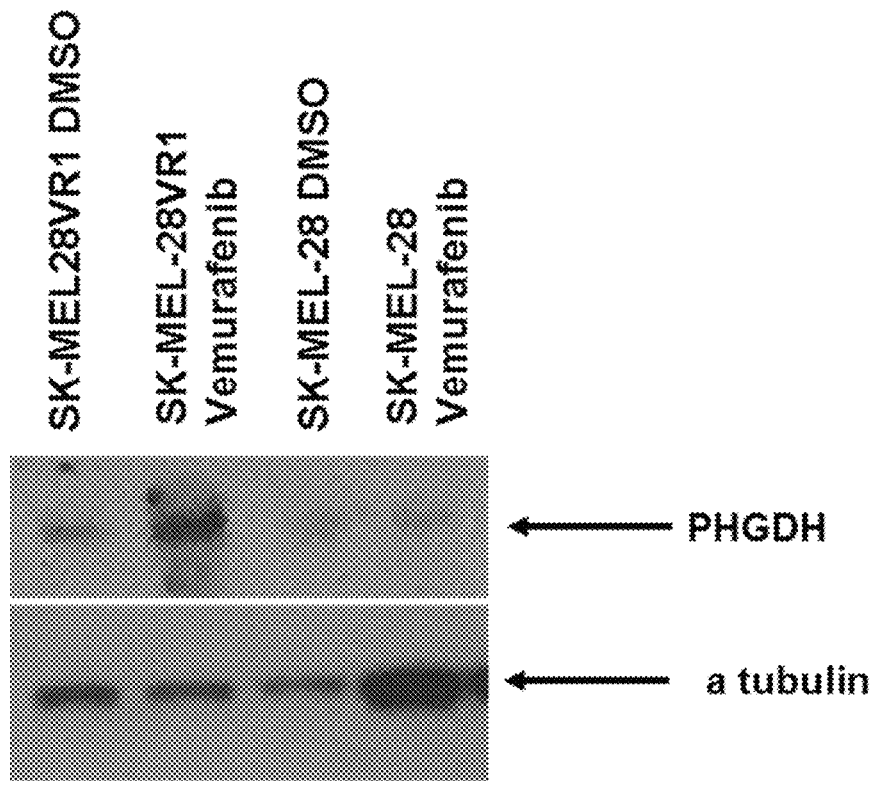

Importantly, serine biosynthesis pathway proteins were the highest differentially expressed proteins within a defined pathway between resistant and sensitive cells in response to vemurafenib. All 3 enzymes of the pathway (PHGDH, PSAT1, PSPH) and serine-tRNA ligases SARS (cytoplasmic) and SARS2 (mitochondrial) were expressed in equal or higher abundances in SK-MEL-28VR1 cells exposed to vemurafenib than to vehicle, while the opposite trend was observed in the parental cells (data not shown). Western blotting using PHGDH antibody confirmed the trends observed through MS analysis (FIG. 5B). Consistent with MS data, western blots revealed that the SK-MEL-28VR1 cells had increased baseline PHGDH expression compared to the parental cells (FIG. 5B). Additionally, the western revealed that PHGDH levels increased following vemurafenib treatment in SK-MEL-28VR1 cells (FIG. 5B), consistent with MS data (not shown).

Figure 6A:
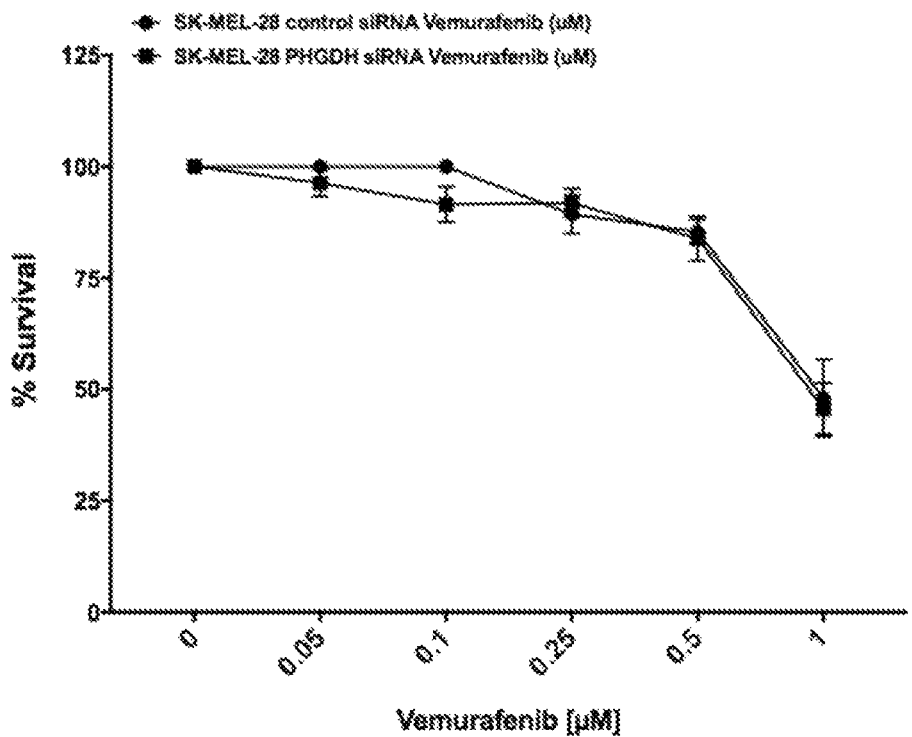
FIG. 6A, FIG. 6B, FIG. 6C, FIG. 6D, and FIG. 6E illustrate the importance of serine biosynthesis pathway to vemurafenib resistance in SK-MEL-28VR1 cells.
Figure 6B:
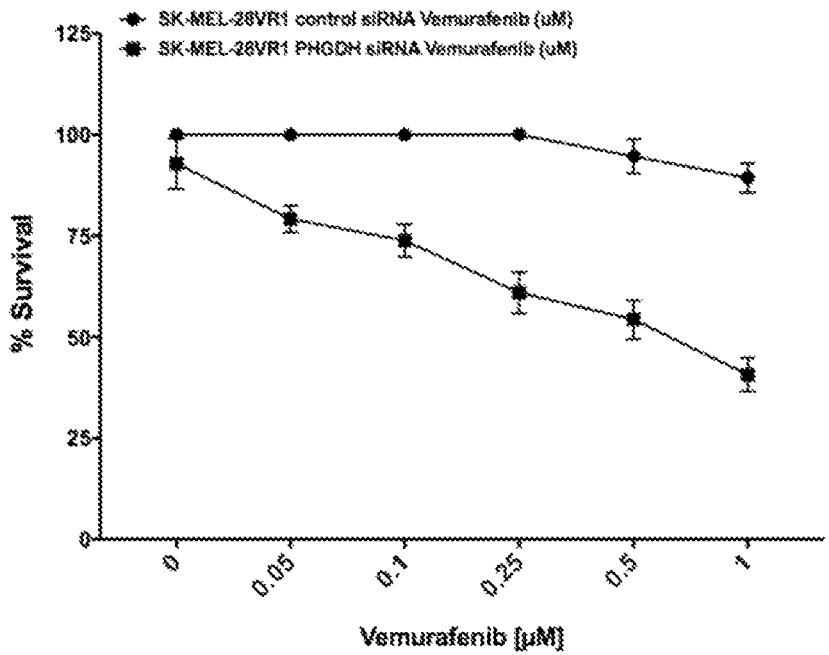
Figure 13:
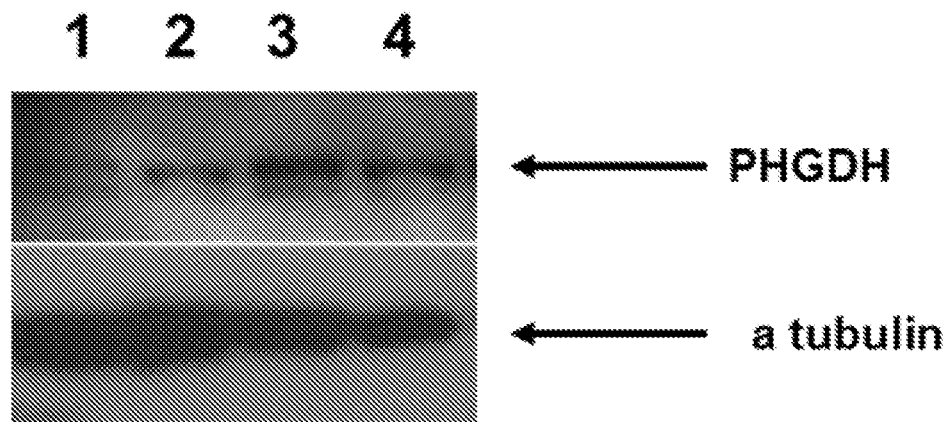
FIG. 13 illustrates PHGDH gene ablation of SK-MEL-28VR1 cells: Lane 1: PHGDH siRNA+vemurafenib. Lane 2: PHGDH siRNA+DMSO. Lane 3: Control siRNA+vemurafenib. Lane 4: Control siRNA+DMSO. Alpha tubulin used as loading control. 50 µg of protein loaded in each lane.

PHGDH is Essential for Vemurafenib Resistance of SK-MEL-28VR1 Cells:

PHGDH is the enzyme that catalyzes the conversion of 3-phosphoglycerate to 3-phosphohydroxypyruvate comprising the first step of the serine synthesis pathway. To directly test whether serine synthesis was critical for vemurafenib resistance, we used siRNA to deplete PHGDH in SK-MEL-28VR1 and SK-MEL-28 cell lines (FIG. 13). PHGDH siRNA significantly enhanced SK-MEL-28VR1 cell death following vemurafenib treatment while not having any additive effect on parental SK-MEL-28 cell death by vemurafenib (FIGS. 6A and 6B). Control siRNA treatments established the baseline of cell viability following vemurafenib treatment for each cell line. PHGDH siRNA+vemurafenib treatments exhibited decreased cell viability below the baseline in SK-MEL-28VR1 cells (FIG. 6B) while parental cells did not (FIG. 6A).

Figure 6C:
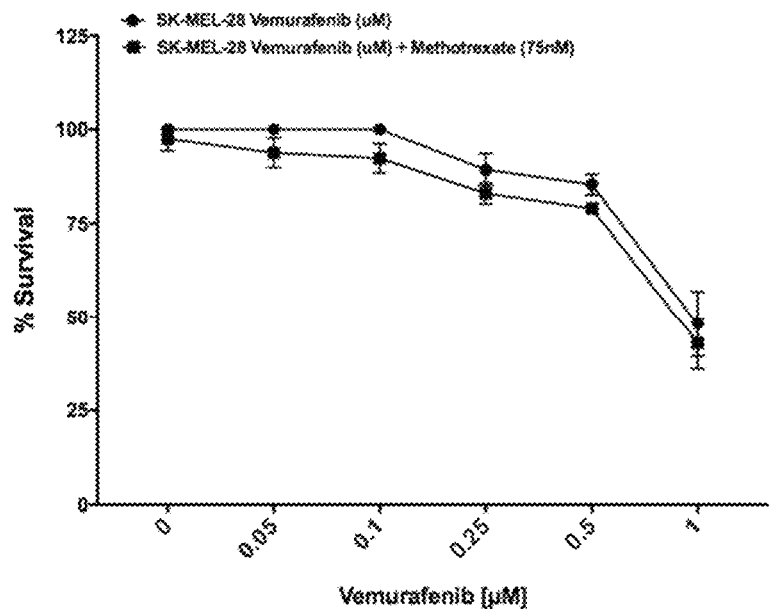
Figure 6D:
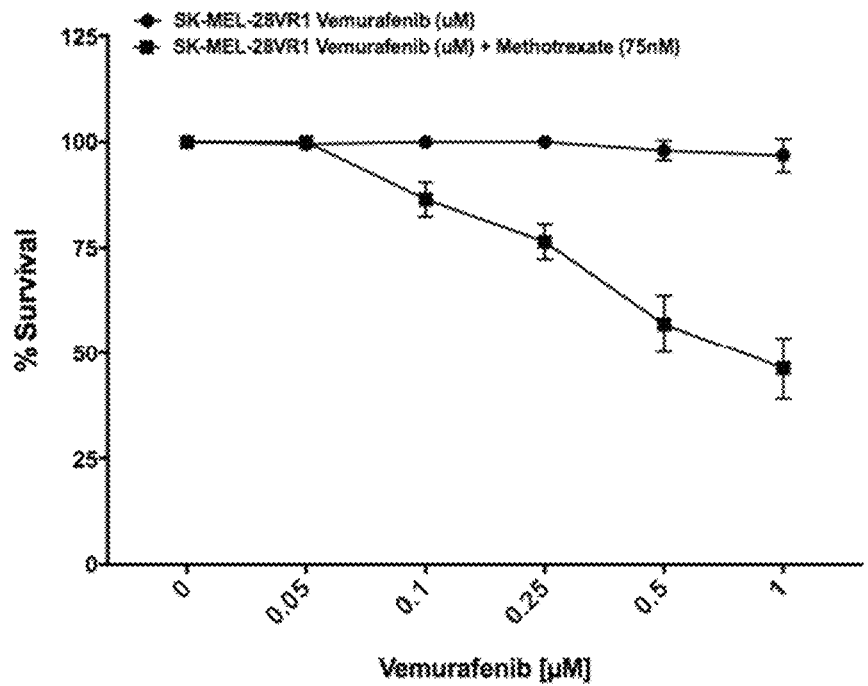

Methotrexate Selectively Sensitizes SK-MEL-28VR1 Cells to Vemurafenib:

As serine biosynthesis proteins are selectively induced in SK-MEL-28VR1 cells and not in parental SK-MEL-28 cells, we investigated whether serine synthesis was contributing to the folate cycle since serine is a direct input of the folate cycle. The folate cycle is necessary for the production of tetrahydrofolate (THF) leading to the production of thymidylate which is critical for DNA synthesis and repair in cancer cells. Additionally, the same study demonstrated that the conversion of serine to glycine and the folate cycle both contribute precursors to the one-carbon metabolic cycle of ATP production in the cytosol of tumor-derived cell lines. Methotrexate, an antifolate, inhibits dihydrofolate reductase and thymidylate synthase thus inhibiting nucleotide synthesis. Methotrexate has also been shown to reduce ATP levels in tumor-derived cell lines. Consistent with the importance of serine to the folate cycle, methotrexate (75 nM) significantly enhanced SK-MEL-28VR1 killing of cells following vemurafenib treatment (FIG. 6D). By contrast, no significant killing by methotrexate/vemurafenib treatments were observed in parental SK-MEL-28 cells (FIG. 6C).

Figure 6E:
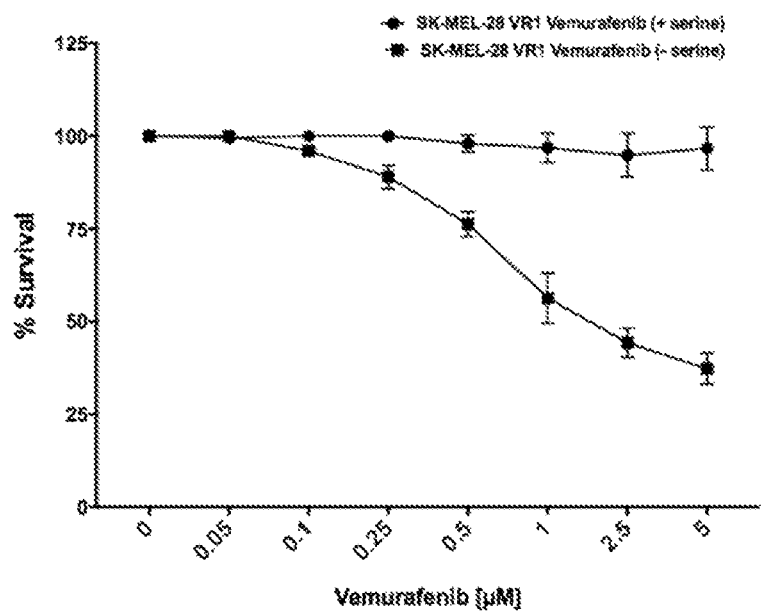

Serine Depletion Sensitizes SK-MEL-28VR1 Cells to Vemurafenib:

Since interrupting the folate cycle downstream of serine synthesis with methotrexate sensitized SK-MEL-28VR1 cells to vemurafenib, we examined the effect of extracellular serine depletion on SK-MEL-28VR1 vemurafenib resistance. We used serine, glucose, and glycine depleted media during cell plating and drug treatments of SK-MEL-28VR1 cells in colony formation assays. Cells were re-fed with complete media following drug treatments and allowed to grow into colonies. Quantitation of colony formation assays revealed an increase in SK-MEL-28VR1 cell death following vemurafenib treatments under serine depleted conditions (FIG. 6E). At vemurafenib doses of 2.5 µM and 5 µM, SK-MEL-28VR1 cells showed >50% cell death with serine depletion but not with complete media. We also examined the effect of high extracellular serine levels on vemurafenib resistance of SK-MEL-28VR1 cells. High amounts of extracellular serine did not affect vemurafenib resistance of SK-MEL-28VR1 cells (data not shown). Taken together, this data show that baseline extracellular serine levels are critical for SK-MEL-28VR1 cell survival under vemurafenib stress conditions.

Figure 7A:
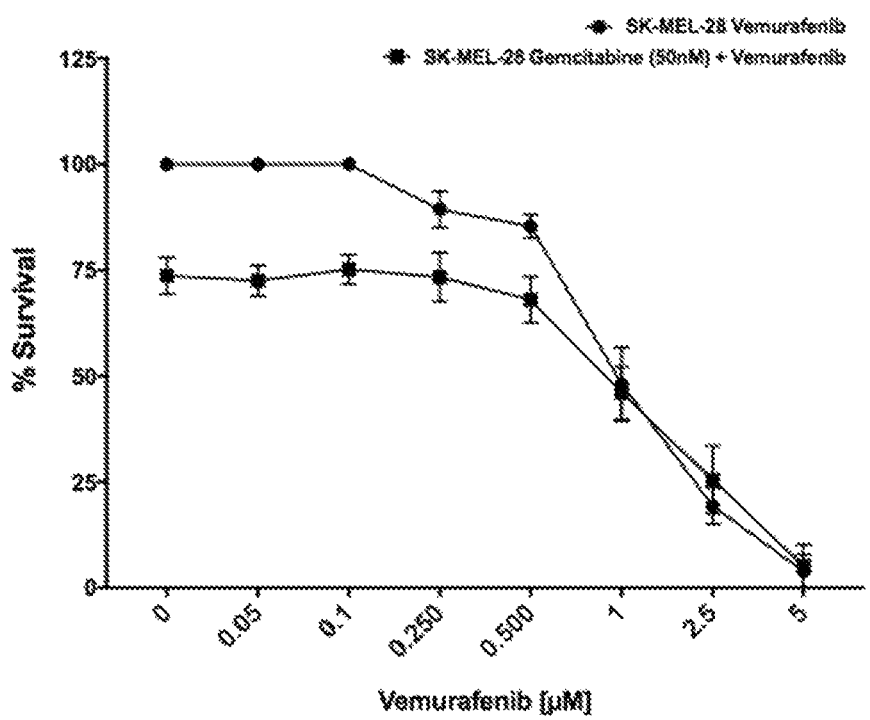
FIG. 7A, FIG. 7B, FIG. 7C, FIG. 7D, FIG. 7E, FIG. 7F, and FIG. 7G illustrate that gemcitabine sensitizes SKMEL-28VR1 cells to vemurafenib.
Figure 7B:
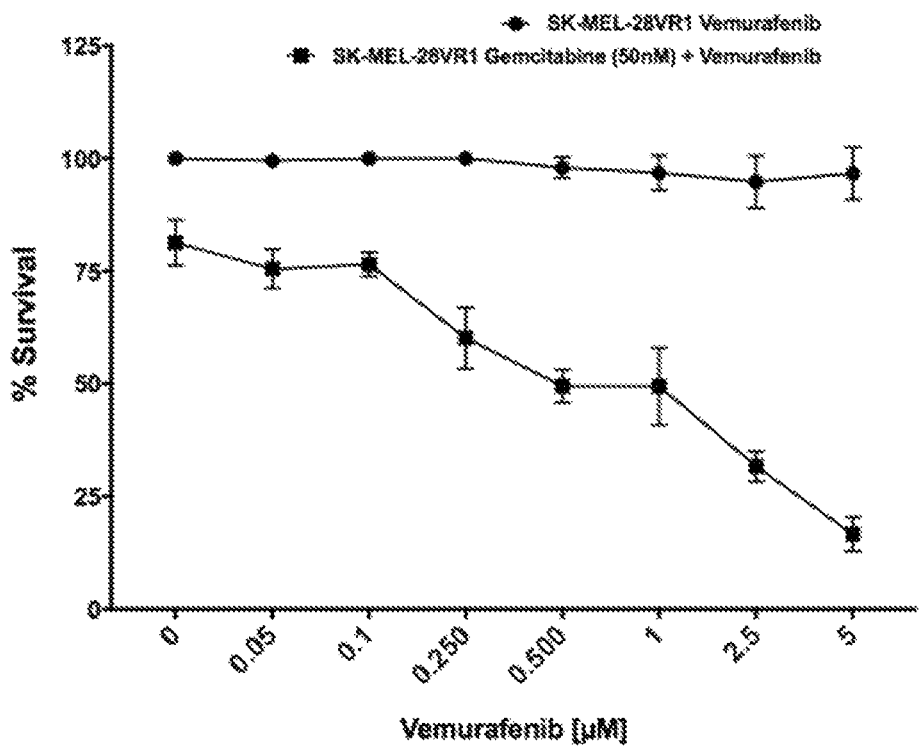
Figure 7C:
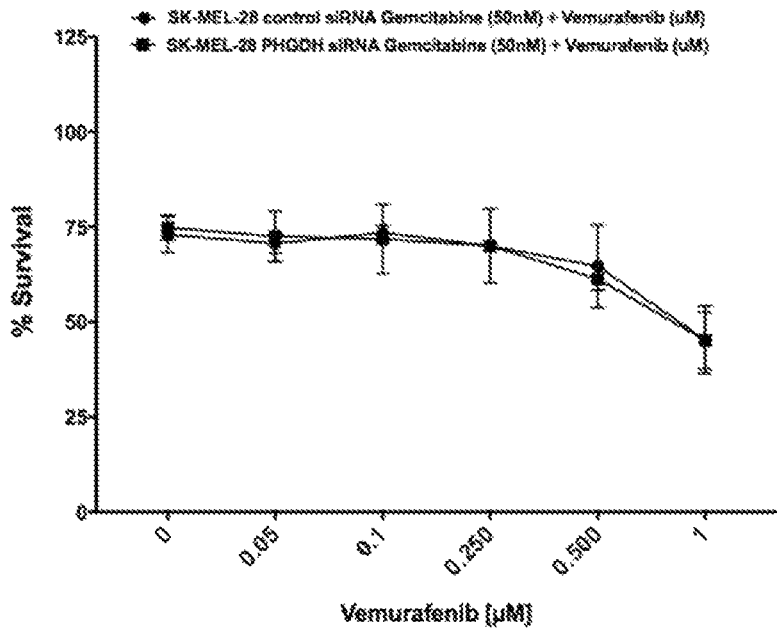
Figure 7D:
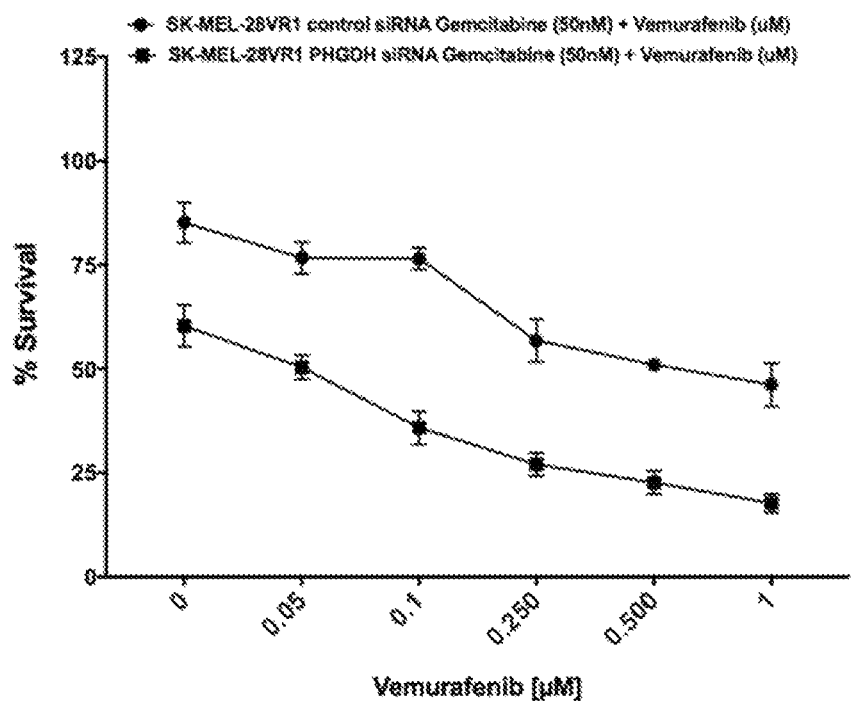
Figure 7E:
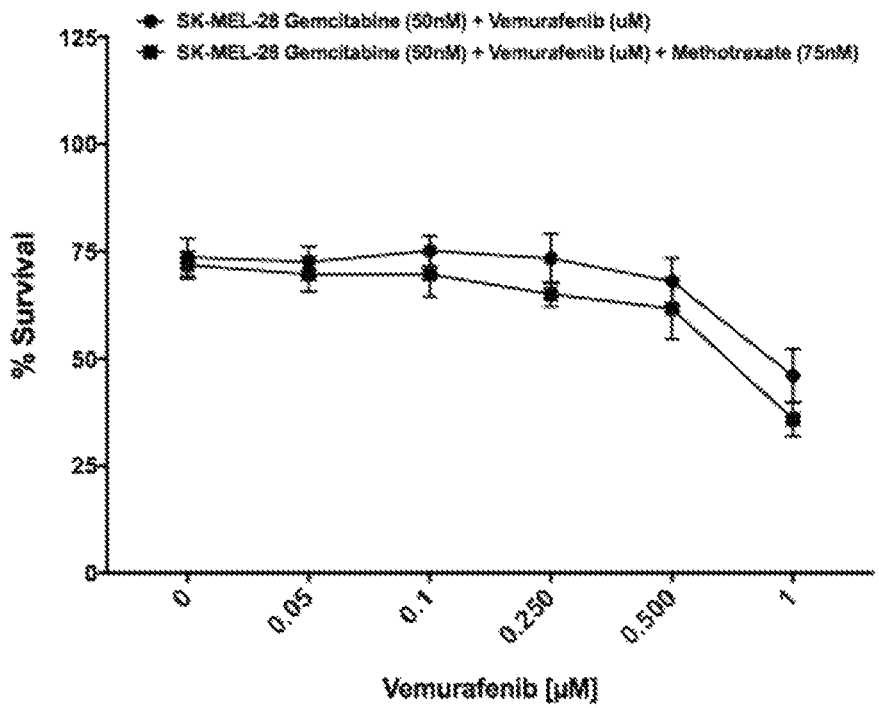
Figure 7F:
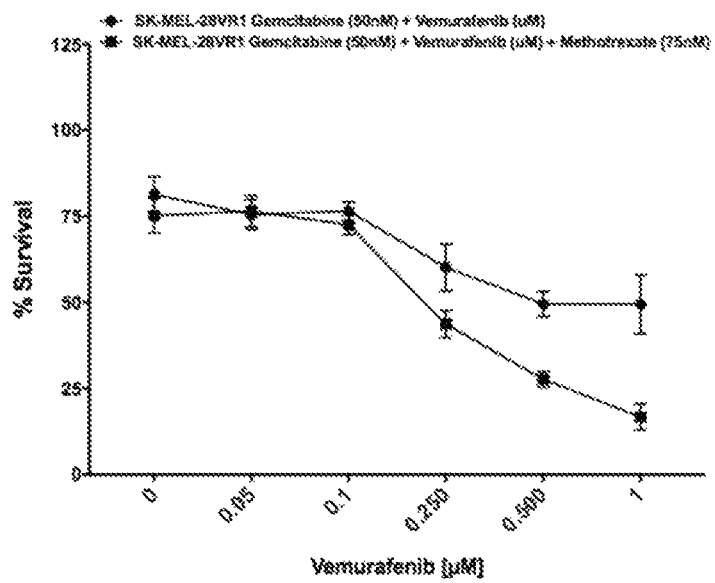
Figure 7G:
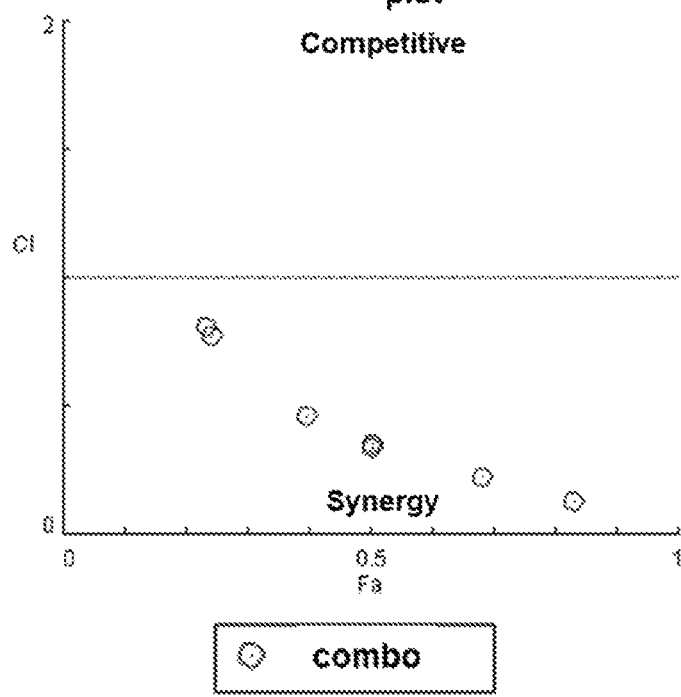
Figure 14A:
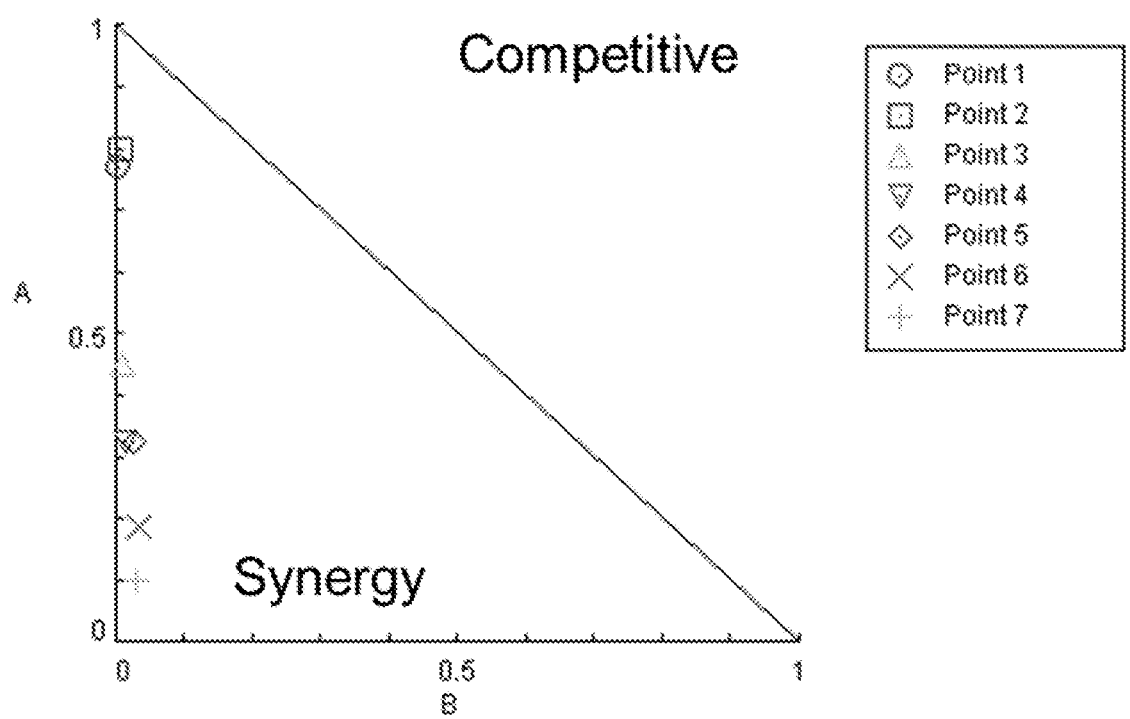
FIG. 14A and FIG. 14B illustrate gemcitabine sensitized SK-MEL-28VR1 and BxPC3M1 cells to vemurafenib.

Identification of Gemcitabine as a Sensitizer of SK-MEL-28VR1 Cells to Vemurafenib:

The folate cycle is critical for nucleotide production during DNA repair, and PHGDH, PSAT1, and PSPH protein levels have been shown to increase under conditions of genomic instability. Therefore, we tested several classes of DNA damaging agents as potential sensitizers of SK-MEL-28VR1 cells to vemurafenib including DNA cross-linking agents, topo isomerase inhibitors, and nucleoside analogs. The nucleoside analog gemcitabine significantly sensitized SK-MEL-28VR1 cells to vemurafenib when used in combination while the combination treatment did not sensitize SK-MEL-28 cells over single vemurafenib treatments (FIGS. 7A and 7B). 50 nM dose of gemcitabine was added to variable doses of vemurafenib in colony formation assays. Importantly, the PHGDH siRNA treatment enhanced SK-MEL-28VR1 cell death beyond cell death observed with gemcitabine/vemurafenib combination treatments while not enhancing cell death of SK-MEL-28 parental cells treated with the gemcitabine/vemurafenib combination (FIGS. 7C and 7D). Additionally, methotrexate significantly enhanced cell death of SK-MEL-28VR1 cells but not SK-MEL-28 cells when treated alongside the gemcitabine/vemurafenib combination (FIGS. 7E and 7F). Importantly, combination index (CI) calculations showed synergy between gemcitabine and vemurafenib in SK-MEL-28VR1 cells at all doses tested (FIG. 7G, Table 3 (below), FIG. 14A).

TABLE 3

CI values for gemcitabine/vemurafenib combination in SK-MEL-28VR1 cells (CI < 1 = synergy, CI = 1 = additive, CI > 1 = Antagonism/competitive).

| CI Data for Non-Constant Combo: gemcitabine + vemurafenib Gemcitabine Dose (nM) | Vemurafenib Dose (uM) | Fraction affected (Fa) Effect | Combination Index CI |
|---|---|---|---|
| point 1 | 50.0 | 0.05 | 0.245 | 0.77220 |
| point 2 | 50.0 | 0.1 | 0.235 | 0.80879 |
| point 3 | 50.0 | 0.25 | 0.3983 | 0.46053 |
| point 4 | 50.0 | 0.5 | 0.505 | 0.33932 |
| point 5 | 50.0 | 1.0 | 0.505 | 0.35296 |

TABLE 3-continued

CI values for gemcitabine/vemurafenib combination in SK-MEL-28VR1 cells (CI < 1 = synergy, CI = 1 = additive, CI > 1 = Antagonism/competitive).

| CI Data for Non-Constant Combo: gemcitabine + vemurafenib Gemcitabine Dose (nM) | Vemurafenib Dose (uM) | Fraction affected (Fa) Effect | Combination Index CI |
|---|---|---|---|
| point 6 | 50.0 | 2.5 | 0.6833 | 0.21981 |
| point 7 | 50.0 | 5.0 | 0.8333 | 0.13013 |

Figure 8A:
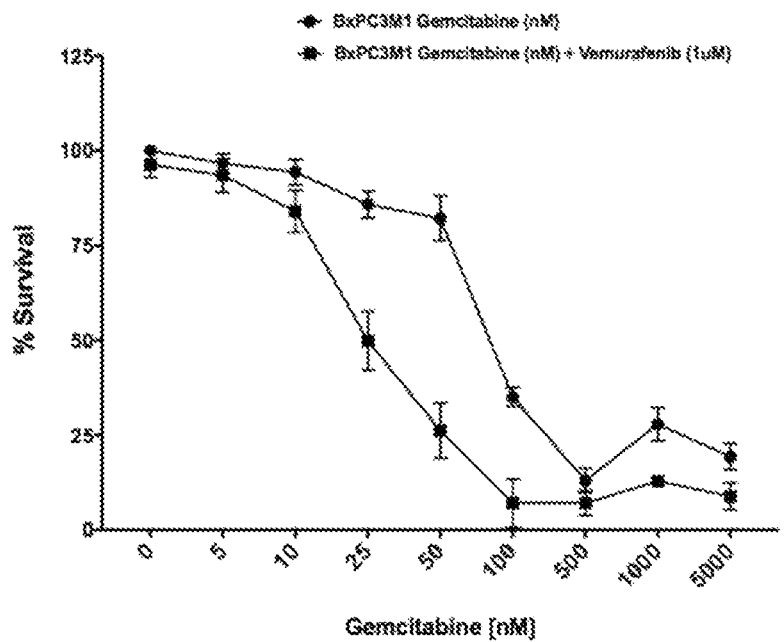
FIG. 8A, FIG. 8B, and FIG. 8C illustrate Gemcitabine sensitizes pancreatic cancer and NSCLC cell lines to vemurafenib.
Figure 8B:
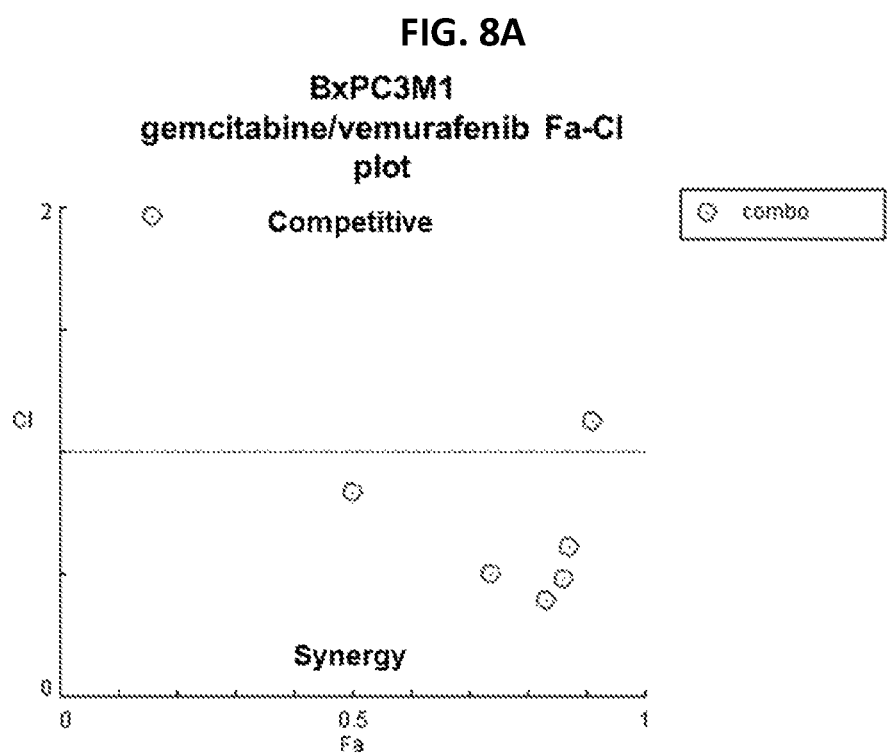
Figure 8C:
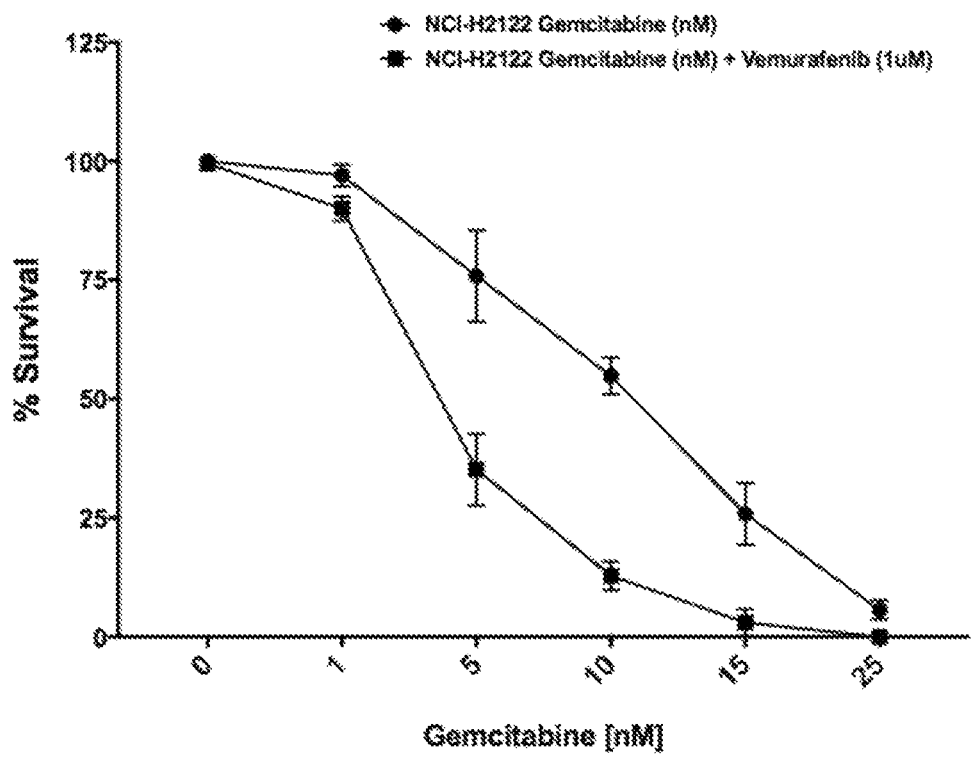
Figure 9A:
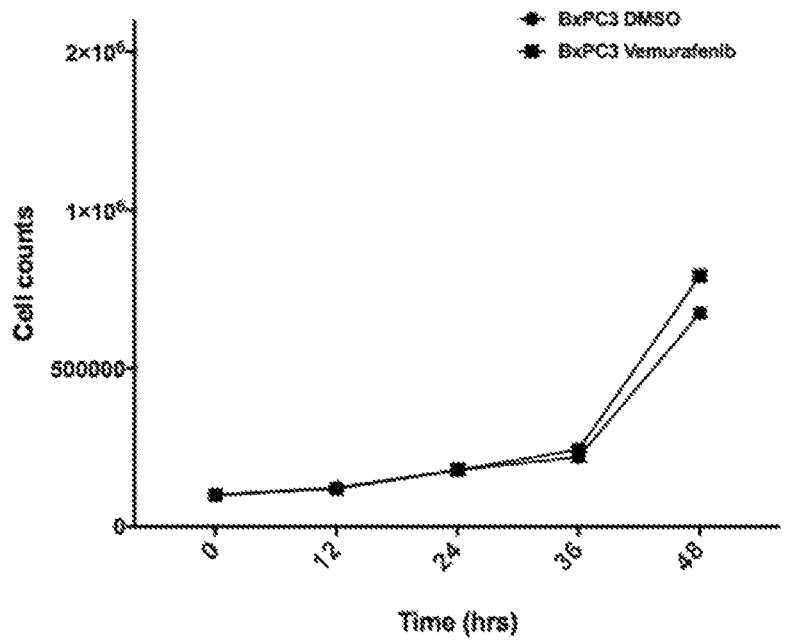
FIG. 9A, FIG. 9B, FIG. 9C, FIG. 9D, FIG. 9E, FIG. 9F, FIG. 9G and FIG. 9H illustrate vemurafenib induced cell proliferation and serine synthesis in pancreatic cancer cell lines.
Figure 9B:
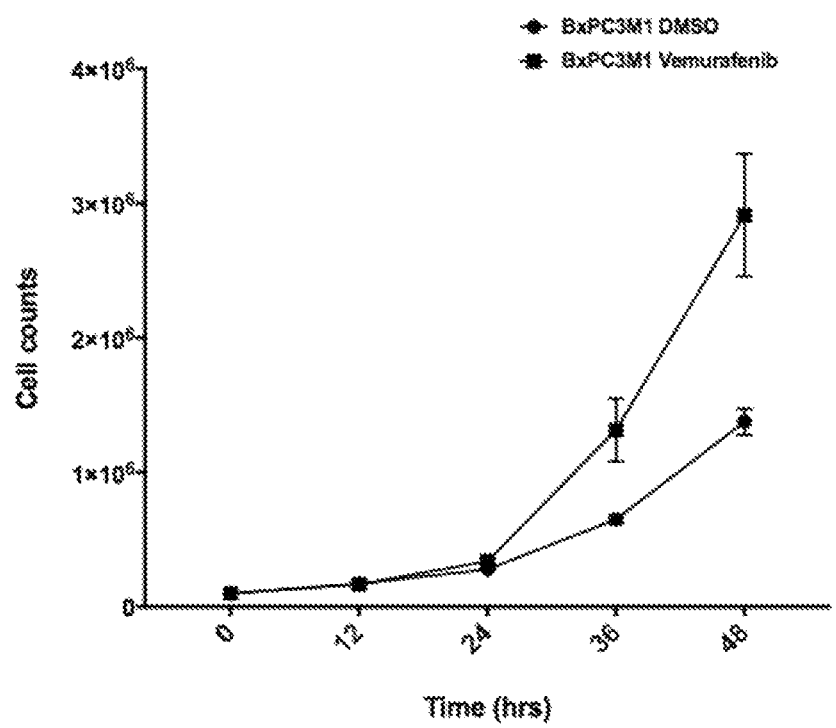
Figure 9C:
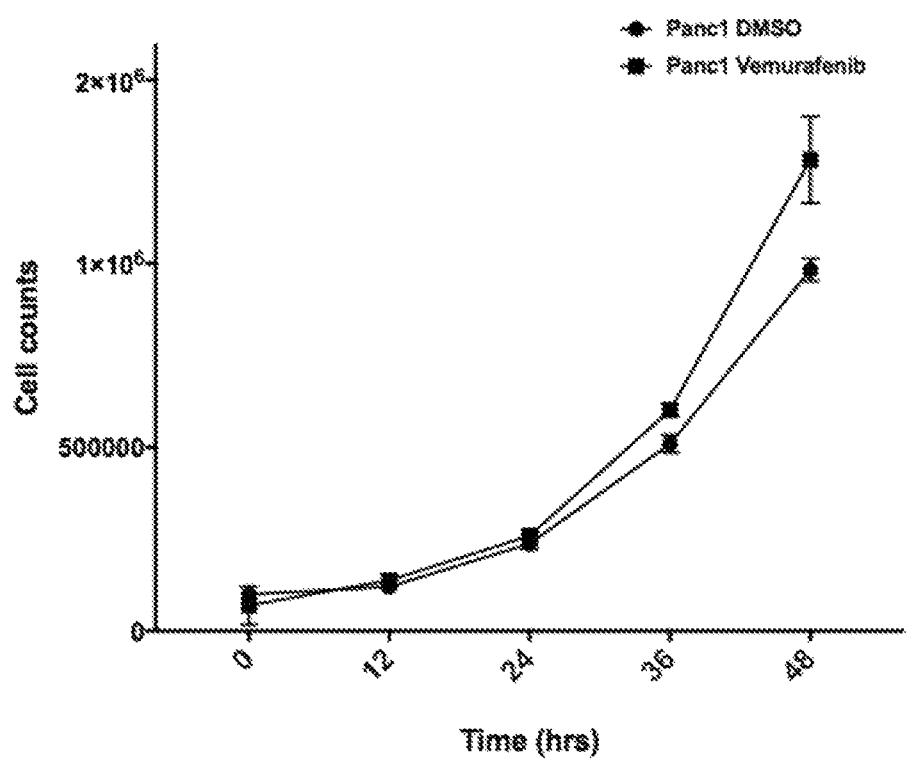
Figure 9D:
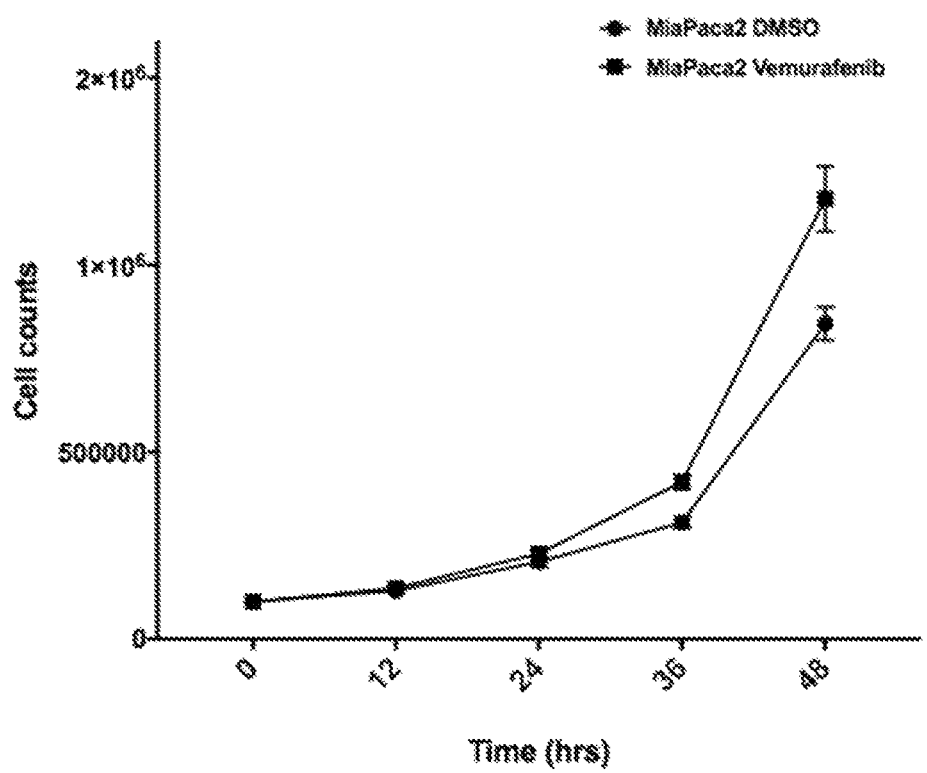
Figure 9E:
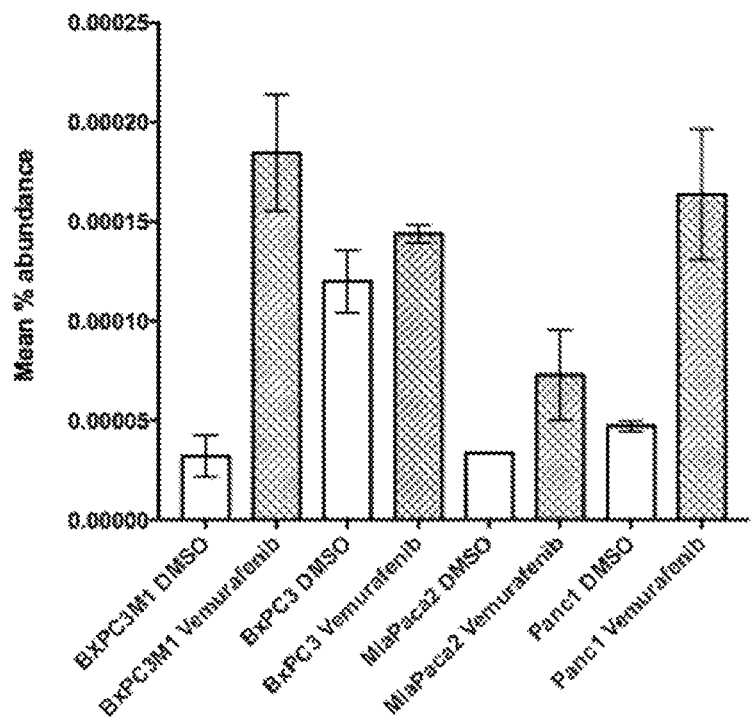
Figure 9F:
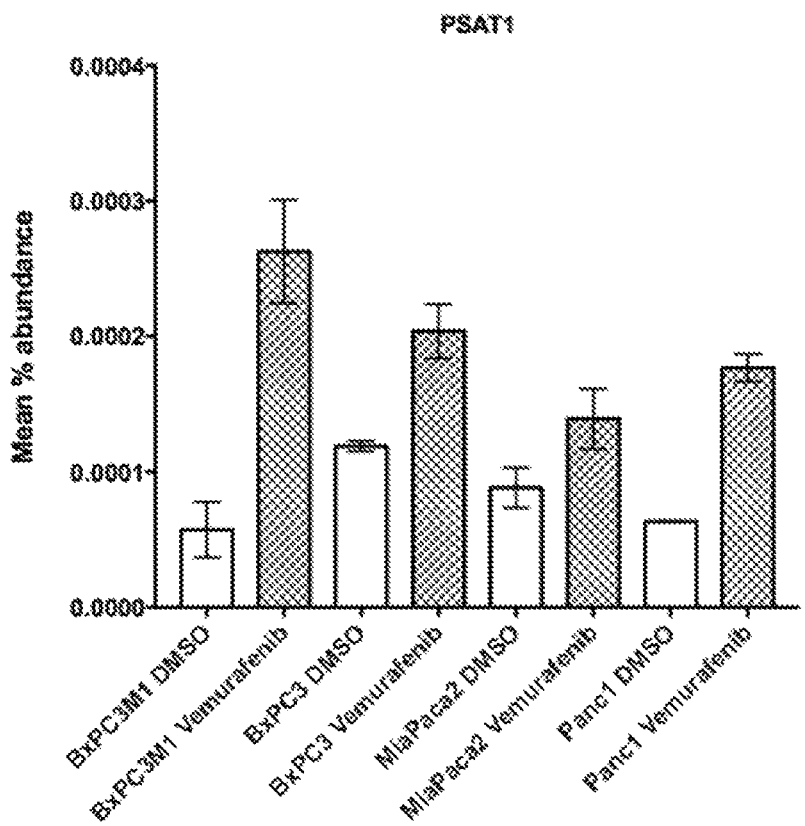
Figure 9G:
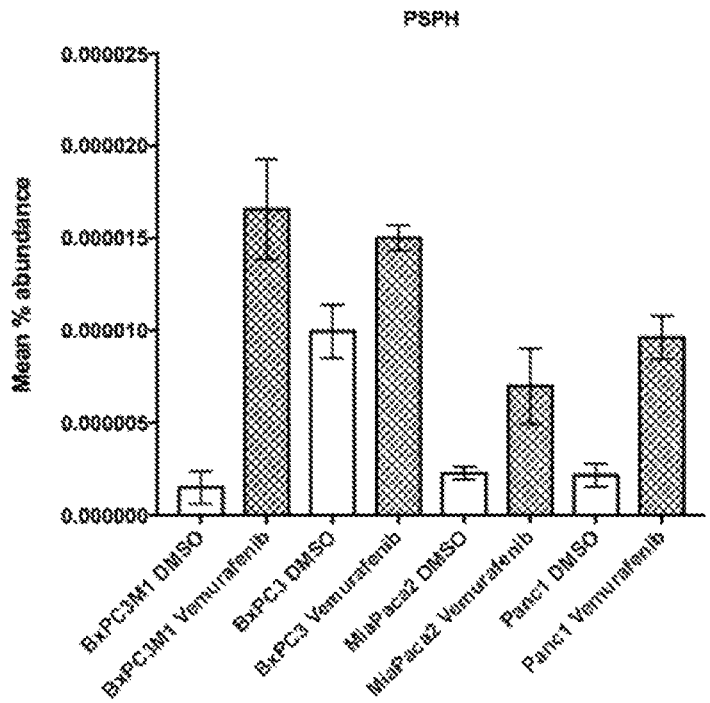
Figure 9H:
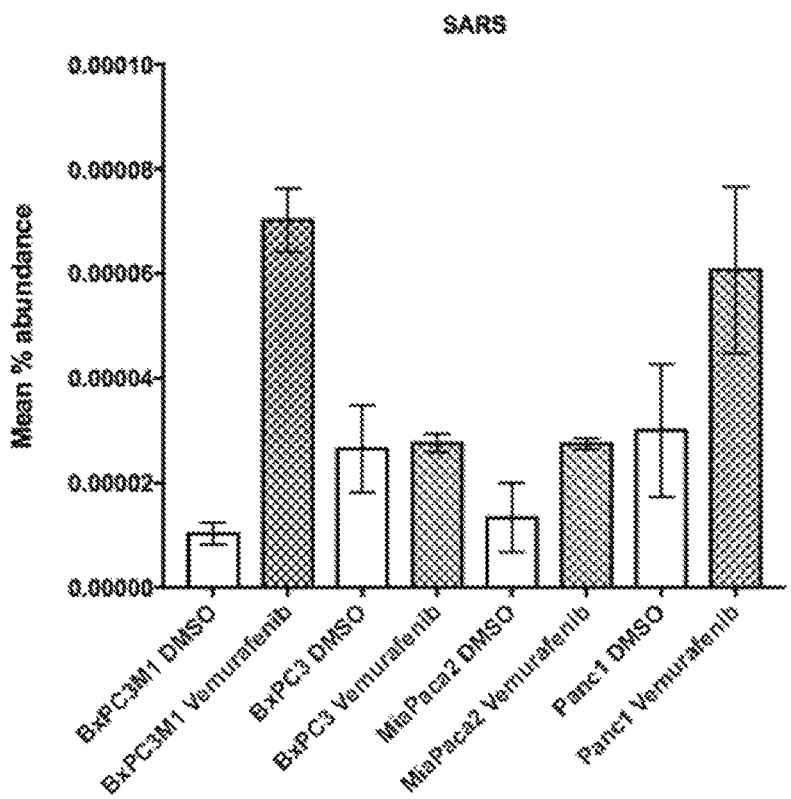
Figure 14B:
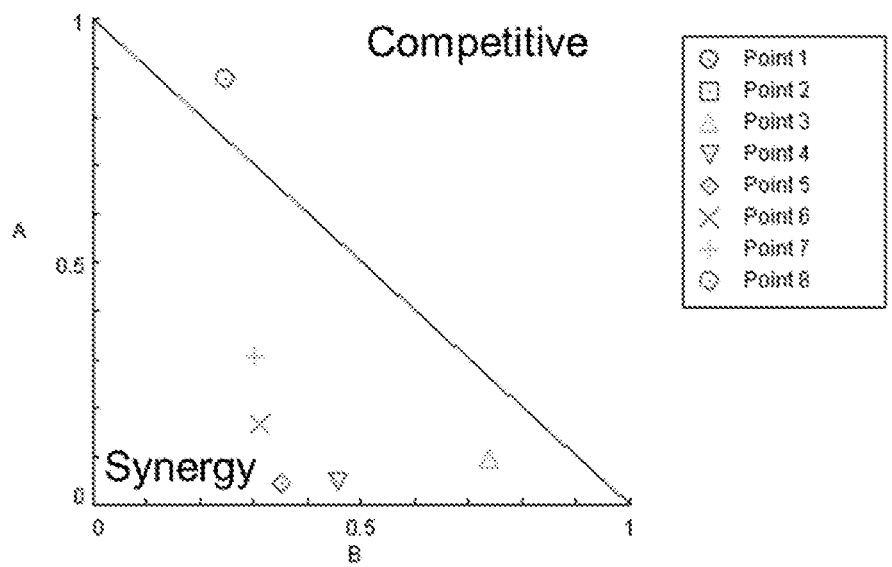

Vemurafenib Sensitizes Pancreatic and Non-Small Cell Lung Cancer Cells to Gemcitabine:

Gemcitabine is the first line therapy in pancreatic cancer. Thus, we tested 4 pancreatic cell lines (BxPC3, Panc1, MiaPaca2, and BxPC3M1) for gemcitabine sensitization via vemurafenib treatment. Using variable gemcitabine doses and a constant vemurafenib dose of 1 µM, colony formation assays revealed that BxPC3M1 cells were significantly sensitized to gemcitabine by vemurafenib (FIG. 8A). Importantly, combination index (CI) calculations showed synergy between gemcitabine and vemurafenib in BxPC3M1 cells at specific doses (FIG. 8B, Table 4, FIG. 14B). The highest (5000 nM) and lowest (5 nM and 10 nM) gemcitabine doses displayed competitiveness between gemcitabine and vemurafenib. However, gemcitabine doses of 25 nM-1000 nM displayed synergy between the two drugs. Additionally, gemcitabine has also been effective in the treatment of advanced non-small cell lung cancer (NSCLC) especially in elderly or unfit patients. We tested a stage 4 adenocarcinoma NSCLC cell line NCI-H2122. We observed that 1 µM vemurafenib sensitized NCI-H2122 cells to gemcitabine (FIG. 8C).

TABLE 4

CI values for gemcitabine/vemurafenib combination in BxPC3M1 cells (CI < 1 = synergy, CI = 1 = additive, CI > 1 = Antagonism/competitive).

| CI Data for Non-Constant Combo: gemcitabine + vemurafenib Gemcitabine Dose (nM) | Vemurafenib Dose (uM) | Fraction affected (Fa) Effect | Combination Index CI |
|---|---|---|---|
| point 1 | 5.0 | 1.0 | 0.065 | 3.25370 |
| point 2 | 10.0 | 1.0 | 0.16 | 1.96412 |
| point 3 | 25.0 | 1.0 | 0.5017 | 0.83638 |
| point 4 | 50.0 | 1.0 | 0.7383 | 0.50599 |
| point 5 | 100.0 | 1.0 | 0.8317 | 0.39812 |
| point 6 | 500.0 | 1.0 | 0.8633 | 0.48194 |
| point 7 | 1000.0 | 1.0 | 0.8717 | 0.60886 |
| point 8 | 5000.0 | 1.0 | 0.9117 | 1.12744 |

Figure 10A:
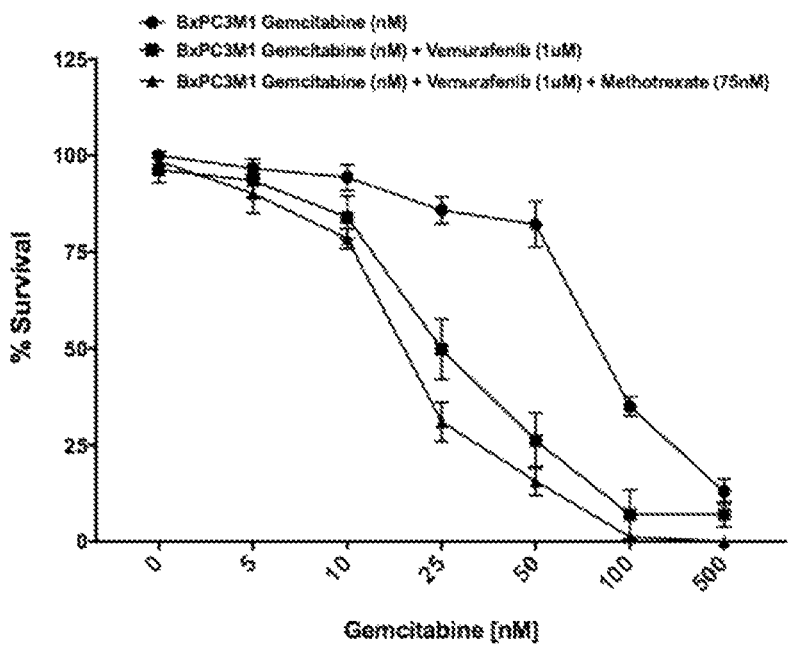
FIG. 10A, FIG. 10B, and FIG. 10C illustrate enhancing vemurafenib induced sensitization of BxPC3M1 and NCI-H2122 cells.
Figure 10B:
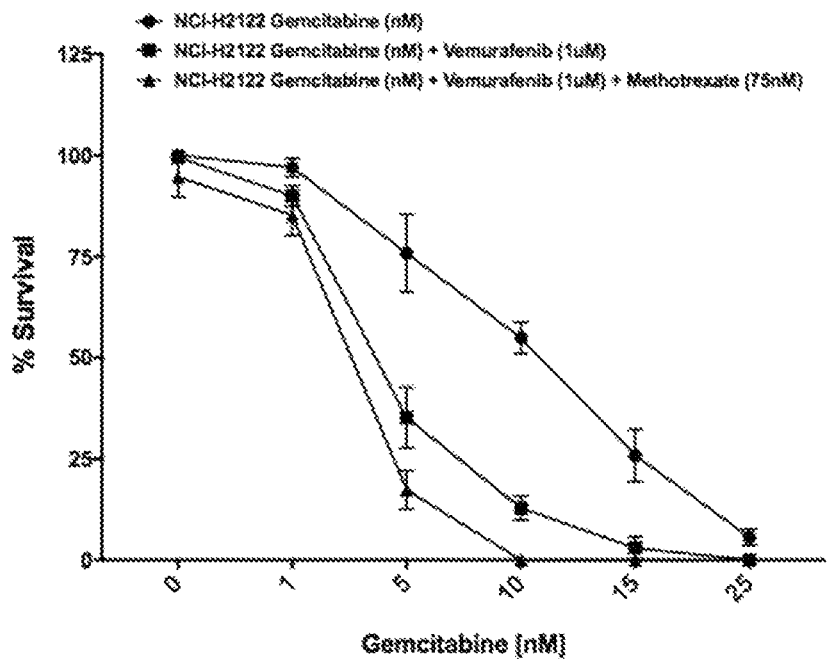
Figure 10C:
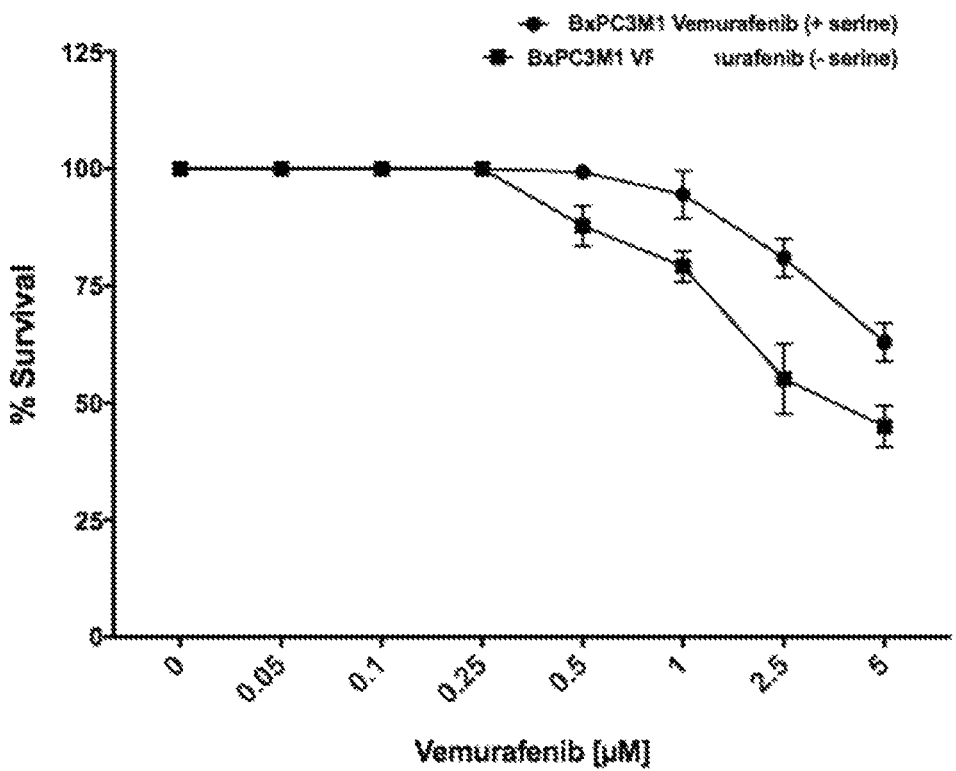

Vemurafenib Induces Serine Synthesis Proteins in Pancreatic Cancer Cells:

Next, we tested the effect of vemurafenib treatment on pancreatic cancer cell proliferation. All 4 of the cell lines (BxPC3M1, BxPC3, Panc1, and MiaPaca2) tested express WT BRAF. Based upon the 2010 *Nature* study, expectedly vemurafenib treatment (10 µM) resulted in increased proliferation of all 4 cell lines FIGS. 9A, 9B, 9C, and 9D). Since serine synthesis has been shown to correlate with increasing proliferation of tumor cells, we compared the proteomic profiles of the pancreatic cell lines via MS. As expected, PHGDH, PSAT1, PSPH, and SARS protein abundance increased in all 4 cell lines tested (FIGS. 9E, 9F, 9G, and 9H). Importantly, the BxPC3M1 cells expressed the highest increase in protein abundance of all 4 proteins compared to the other 3 cell lines tested. Additionally, methotrexate treatments in combination with gemcitabine+vemurafenib increased cell death of BxPC3M1 and NCI-H2122 cells compared to gemcitabine+vemurafenib treatments without methotrexate (FIGS. 10A and 10B). Next, we examined the effect of extracellular serine depletion on BxPC3M1 vemurafenib resistance. We used serine, glucose, and glycine depleted media during cell plating and drug treatments of BxPC3M1 cells in colony formation assays. Cells were re-fed with complete media following drug treatments and allowed to grow into colonies. Quantitation of colony formation assays revealed a significant increase in BxPC3M1 cell death following vemurafenib treatments under serine depleted conditions (FIG. 10C). At the 5 µM vemurafenib dose, BxPC3M1 cells showed >50% cell death with serine depleted media but not with complete media.

Figure 11A:
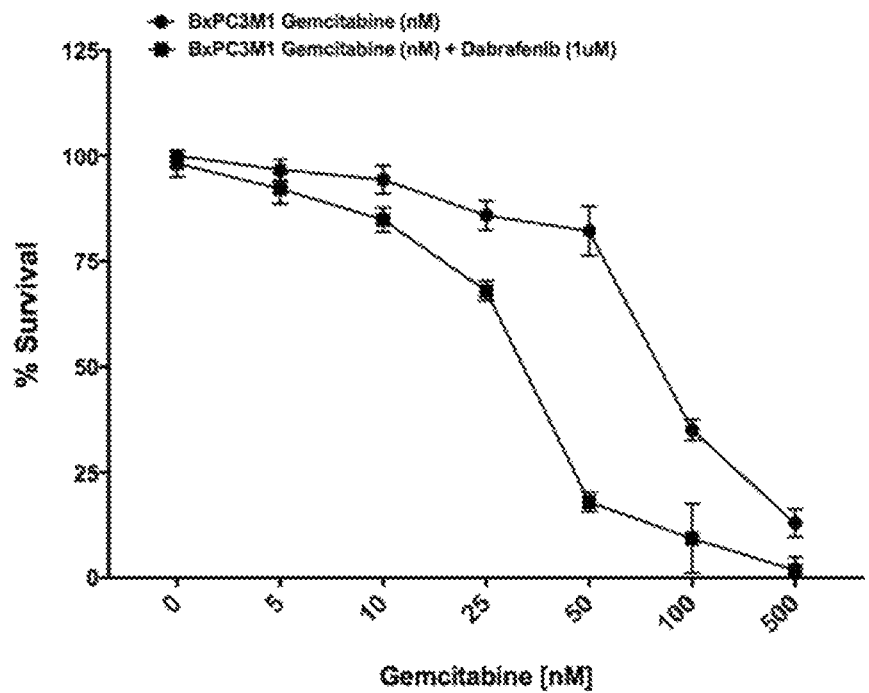
FIG. 11A, FIG. 11B, and FIG. 11C illustrate dabrafenib induced sensitization of BxPC3M1, NCI-H2122, and SK-MEL-28VR1 cells to gemcitabine.
Figure 11B:
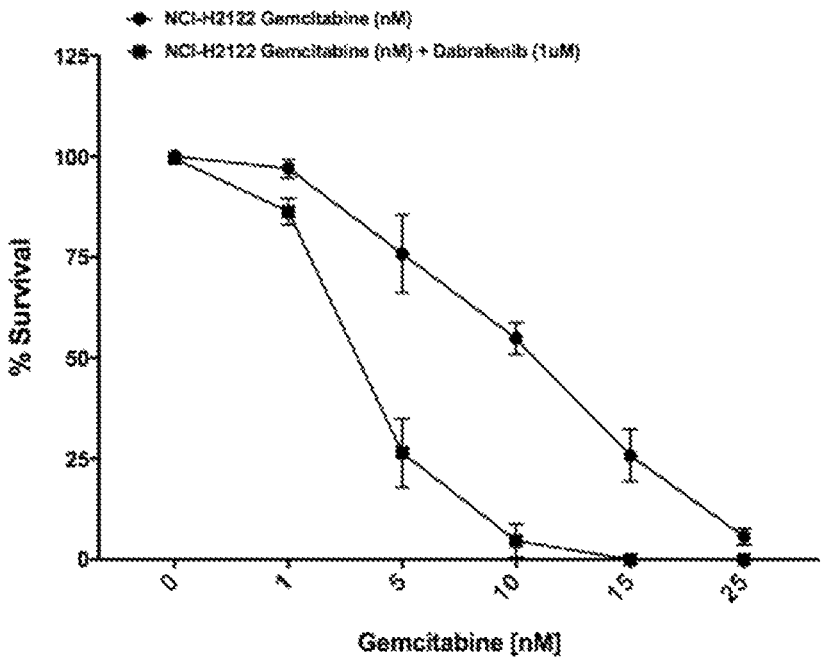
Figure 11C:
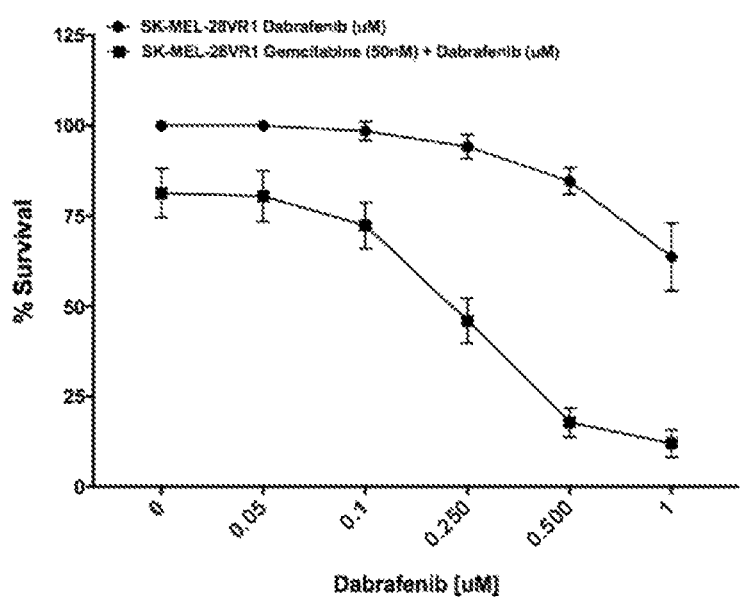

Dabrafenib, Another BRAF Inhibitor, Sensitizes Cancer Cells to Gemcitabine:

Similar to vemurafenib, dabrafenib is a BRAF V600E inhibitor that has efficacy against metastatic melanoma. We tested the effectiveness of dabrafenib to sensitize SK-MEL-28VR1, BxPC3M1, and NCI-H2122 cells. The first-line drug of each disease state was given in variable doses. Dabrafenib is considered as first line therapy in metastatic melanoma with BRAF V600E mutations while gemcitabine is the first line therapy in pancreatic cancer and NSCLC. For SK-MEL-28VR1 cells, gemcitabine dose was kept constant at 50 nm with variable doses of dabrafenib. In contrast, dabrafenib dose was kept constant at 1 µM with variable doses of gemcitabine in the pancreatic cancer and NSCLC cell lines. Interestingly, dabrafenib treatment sensitized BxPC3M1 and NCI-H2122 cells to gemcitabine (FIGS. 11A and 11B), and gemcitabine sensitized SK-MEL-28VR1 cells to dabrafenib (FIG. 11C).

Discussion: We isolated vemurafenib resistant SK-MEL-28 cells (SK-MEL-28VR1) to study mechanisms of BRAF V600E inhibitor resistance. Our proteomic data differentiated the protein signatures of SK-MEL-28VR1 cells from their parental SK-MEL-28 cells in response to vemurafenib. The serine biosynthesis pathway enzyme levels (PHGDH, PSAT1, and PSPH, as well as the serine tRNA-ligases SARS1/2) were observed to be elevated in response to vemurafenib treatments of SK-MEL-28VR1 cells. By contrast, all five of the proteins mentioned decreased in response to vemurafenib treatments of SK-MEL-28 parental cells. Subsequent western blotting confirmed the protein trends observed from MS assays. From these results, we postulate that serine synthesis is critical for vemurafenib resistance of SK-MEL-28VR1 cells. Serine synthesis has been shown to be critical for cancer cell proliferation. This shows that serine and not glycine was critical for nucleotide and amino acid synthesis during cancer cell proliferation. Indeed, SK-MEL-28VR1 cells had a higher proliferation rate (16 hour doubling time) compared to SK-MEL-28 cells (23.1 hour doubling time). Our proteomic observations of serine biosynthesis induction in response to vemurafenib in SK-MEL-28VR1 cells support published reports that positively correlate serine synthesis to increasing cancer cell survival (Mattaini et al., 2016; Possemato et al., 2011).

Colony formation assays following PHGDH ablation via siRNA confirmed the importance of PHGDH gene products to SK-MEL-28VR1 resistance to vemurafenib. This data along with colony formation assays following methotrexate treatments confirmed serine synthesis as a critical component of the resistance signature of SK-MEL-28VR1 cells. PHGDH catalyzes the first step of the serine biosynthesis pathway converting 3-phosphoglycerate to 3-phosphohydroxypuruvate. Moreover, PHGDH gene amplifications have been reported in breast cancer and melanoma. In fact, certain breast cancer cell types have shown to be dependent upon increased serine synthesis flux through higher PHGDH gene expression. Additionally, in NSCLC, PHGDH gene amplification and over-expression positively correlates with aggressive disease. Importantly, PHGDH gene is often amplified in metastatic melanoma and its knockdown negatively affects cell viability. The PHGDH ablation induced vemurafenib sensitization is reminiscent of the BRCA1 ablation and platinum based chemotherapy story in breast cancer.

Serine biosynthesis lies upstream and feeds into multiple pathways involved in nucleotide and amino acid metabolism. Specifically, the folate cycle contributes to nucleotide metabolism. We tested the antifolate drug methotrexate in combination with vemurafenib on SK-MEL-28 and SK-MEL-28VR1 cell viability. Methotrexate selectively sensitized SK-MEL-28VR1 cells to vemurafenib. Methotrexate is known to inhibit the folate cycle which sits downstream of serine biosynthesis in the alternative metabolic pathway known as SOG (Serine-One carbon cycle-Glycine cleavage) which is activated in cancer cells during proliferation. Moreover, serine depletion experiments demonstrated the need for baseline levels of extracellular serine for SK-MEL-28VR1 vemurafenib resistance. Recent work has identified the need for BRAF inhibitor resistant melanoma cells to switch to oxidative metabolism during induction of cell proliferation. In fact, resistant cells are reported to be overly dependent on glutamine rather than glucose for proliferation. Interestingly, glutamate, catalyzed from glutamine, is a precursor of the second step of the serine biosynthesis pathway. The enzyme PSPH catalyzes the conversion of glutamate to α-ketoglutarate during the conversion of 3-phosphohydroxypyruvate to phosphoserine. We postulate that serine synthesis is active in our SK-MEL-28VR1 cells potentially as a result of the described switch to oxidative metabolism during proliferation. Further studies are needed to examine the dependency of SK-MEL-28VR1 cells to glutamine.

Among other high confidence hits, FAM129B was identified as one of the most differentially expressed proteins between the two cell lines with respect to vemurafenib treatment. FAM129B is an adherens junction-associated protein also known as Niban-like protein 1. FAM129B is phosphorylated on four serine residues by the BRAF/MAPKK/ERK signaling cascade and FAM129B is known to be dispersed throughout the cytoplasm of melanoma cells only under conditions when the MAPK pathway is active. Inhibiting the MAPK cascade with the chemical inhibitor U0126 caused FAM129B to localize to the cell membrane. Smalley et al. showed that FAM129B overexpression increased the invasive potential of melanoma cells. FAM129B affects multiple signaling pathways in melanoma downstream of the MAPK cascade. In our assays, cytoplasmic FAM129B protein abundance increased in SK-MEL-28VR1 cells following vemurafenib treatment but decreased in SK-MEL-28 cells. Therefore, FAM129B protein trends in our MS assays suggested that vemurafenib induced MAPK pathway activation in SK-MEL-28VR1 cells but not in SK-MEL-28 cells. Further, MAPK activation suggested vemurafenib may induce cell proliferation in SK-MEL-28VR1 cells supporting the observation of serine synthesis induction. We are currently investigating FAM129B as a potential biomarker for vemurafenib resistance in metastatic melanoma cells.

Interestingly, the folate cycle is known to contribute to the replenishment of nucleotide pools during cell proliferation, and DNA damage induces the production of nucleotides. Moreover, the 3 serine synthesis enzyme levels have all been shown to increase under conditions of DNA damage and genomic instability. We tested several DNA damaging agents as sensitizers of SK-MEL-28VR1 cells to vemurafenib. Gemcitabine was identified as a sensitizer when SK-MEL-28VR1 cells were pre-treated with the drug before addition of vemurafenib. Combination index calculations revealed synergy between gemcitabine and vemurafenib in SK-MEL-28VR1 cells. Gemcitabine is a deoxycytidine analog, which has been the primary chemotherapy against multiple tumor types including pancreatic and lung cancers. Gemcitabine causes DNA double strand breaks (DSBs) as a result of replication fork collapse in the S-phase of the cell cycle in p53 mutated cells or induces apoptosis through PUMA and Bax mediated cell death programs in G1 in p53 WT cells. However, mutations commonly occurring in p53 and other genes of pancreatic and lung cancer tumor cells drive acquired resistance to gemcitabine resulting in low rates of disease free survival. The p53 mutated cancer cells become arrested in S-phase following treatment with gemcitabine at nM doses but do not die. Whereas, p53 WT cells die following G1 arrest at identical doses. Mutations in gatekeeper genes like p53, BRAF, and KRAS are common events in natural cancer cell progression; therefore, the innate ability of cancer cells to resist the DNA damaging effects of drugs as they progress towards metastasis is especially problematic. Nevertheless, gemcitabine remains the first line therapy against advanced pancreatic cancer (PCa).

The order of drug addition was critical to the success of our gemcitabine/vemurafenib combination in SK-MEL-28VR1 cells. Experiments with simultaneous drug treatments or vemurafenib or dabrafenib pre-treatments followed by gemcitabine treatments did not exhibit significant sensitization (data not shown). We postulate that SK-MEL-28VR1 cells are arrested in S-phase because of DNA double strand breaks caused by gemcitabine. As a result, when we treat the arrested cells with vemurafenib, the MAPK cascade is activated inducing serine biosynthesis and the folate cycle. We believe that these series of events ultimately lead to cell death in SK-MEL-28VR1 cells. Further experimentation is warranted to fully characterize SK-MEL-28VR1 cell death via the gemcitabine/vemurafenib combination. We postulate that DNA damage induces cell cycle arrest in SK-MEL28VR1 cells for DNA repair to commence activating the folate cycle and nucleotide synthesis. While cells are arrested, BRAF V600E inhibitor treatment activates the MAPK pathway inducing serine synthesis and nucleotide synthesis. Two conflicting pathways depleting the nucleotide pool of the cells cause cell death.

Next, we replicated our vemurafenib studies in BRAF WT cancer cell lines that are naturally not responsive to the drug. Since vemurafenib is known to increase proliferation of cells with BRAF WT backgrounds, we postulate serine biosynthesis might be critical for cell survival and proliferation under vemurafenib treatment conditions. We examined multiple cancer cell lines that are BRAF WT and are intrinsically resistant to vemurafenib. We tested pancreatic, NSCL, breast, and colon cancer cells. Indeed, MS studies identified the serine biosynthesis pathway as greatly induced in BRAF WT pancreatic cancer cells in response to vemurafenib treatments. BxPC3M1 cells had the highest increase in serine synthesis enzymes of the pancreatic cancer cell lines with drug treatment. Then we tested gemcitabine at variable doses and kept vemurafenib dose constant. One pancreatic (BxPC3M1) and one NSCL (NCI-H2122) cancer cell line were sensitized to gemcitabine/vemurafenib combination treatments. The order of drug addition played a significant role for sensitization. Gemcitabine pre-treatment demonstrated a synergistic effect for sensitization when combined with the BRAF inhibitors. Combination index calculations revealed synergy between gemcitabine and vemurafenib at gemcitabine doses of 25 nM-1000 nM. The two drugs had a competitive relationship at gemcitabine doses of 5 nM, 10 nM, and 5000 nM. This data showed that 5000 nM dose of gemcitabine alone caused cell death and adding in 1 µM vemurafenib reduces the toxicity of gemcitabine. However, lower doses of gemcitabine (25 nM-1000 nM) synergized with vemurafenib. At the lowest doses of gemcitabine (5 nM and 10 nM) the two drugs have a competitive relationship. These doses of gemcitabine appear too low to have any effect on our CI plots. We believe that cell cycle arrest is necessary for vemurafenib induced cell death in BxPC3M1 cells. Additionally, BxPC3M1 cell proliferation was induced by vemurafenib treatment. Serine depletion experiments demonstrated the need for baseline levels of extracellular serine for BxPC3M1 vemurafenib resistance. Importantly, gemcitabine sensitized SK-MEL-28VR1, BxPC3M1, and NCI-H2122 cells to a second BRAF V600E inhibitor dabrafenib. Collectively, our data showed that acquired resistance of SK-MEL-28VR1 cells and intrinsic resistance of BxPC3M1 and NCI-H2122 cells to vemurafenib or dabrafenib can be reversed via gemcitabine addition. Gemcitabine and vemurafenib showed synergy in SK-MEL-28VR1 and BxPC3M1 cells.

Since we did not observe sensitization with the gemcitabine/vemurafenib combination across all pancreatic cancer and NSCLC cell lines tested, we have started to examine the unifying characteristics among the responders, SK-MEL28VR1, BxPC3M1, and NCI-H2122 cells. We know from previous RNA sequencing data (data not shown) that BxPC3M1 cells have homozygous KRAS G12C mutations identical to the NCI-H2122 cell line. Additionally, KRAS G12V mutations have arisen in SK-MEL-28VR1 cells. Additionally, the NCI-H2122 cells and BxPC3M1 cells are WT for BRAF. However, an interesting observation we are exploring further is a qualitative feature common to SK-MEL-28VR1, BxPC3M1, and NCI-H2122 cells. All three cell lines have a detached phenotype (data not shown). This phenotype is consistent with the detached phenotype of mesenchymal cancer cells. There is precedence for epithelial to mesenchymal transition (EMT) being a path to vemurafenib resistance. We are currently working on fully characterizing SK-MEL-28VR1, BxPC3M1, and NCI-H2122 cells on the EMT scale as well as examining their metastatic potential through 3D gel invasion studies and genomic sequencing. We postulate that metastatic potential as well as mutational profile are critical determinants of cell sensitivity to the gemcitabine/vemurafenib combination illuminating the potential for personalized therapies. Moreover, we are further examining responses of additional resistant melanoma cell lines to methotrexate+vemurafenib or dabrafenib treatments.

Figure 12A:
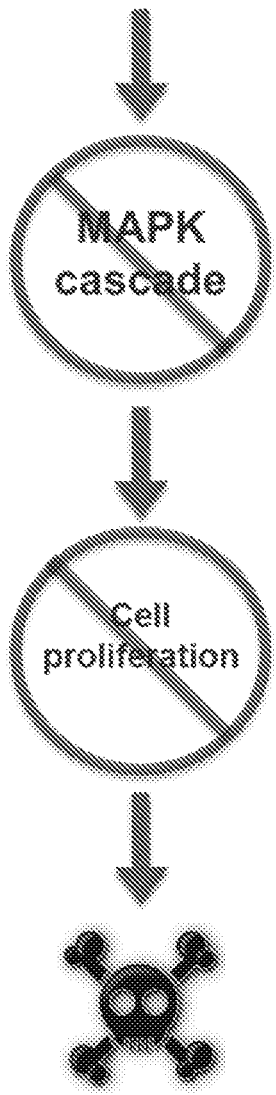
FIG. 12A and FIG. 12B illustrate schematics of cancer cell sensitization via sequential combination treatment with gemcitabine and a BRAF V600E inhibitor: The cascade in FIG. 12A represents SK-MEL-28 cellular response to BRAF V600E inhibitors (BRAFi) within the BRAF V600E mutation. The left side of the cascade in FIG. 12B represents acquired BRAFi resistant SKMEL-28VR1 cellular response to BRAFi within the mutation profile. Acquired resistance causes a paradoxical induction of the MAPK cascade without gemcitabine pre-treatment. Gemcitabine pre-treatment followed by BRAFi leads to paradoxical induction of the MAPK cascade and induction of serine synthesis while cells are arrested. Induction of serine synthesis leads to an induction of the folate cycle for nucleotide synthesis. These series of events lead to cell death due to conflicting activation of cellular signaling pathway causing cell cycle arrest signal from gemcitabine-induced DNA damage and activation of MAPK signaling pathway by BRAF inhibitors. The right side of the cascade in FIG. 12B shows sensitization of BRAF WT pancreatic cancer BxPC3M1 and non-small cell lung cancer NCI-H2122 cells to BRAF inhibitors by gemcitabine pretreatment. In these BRAF WT cell lines, gemcitabine induces cell cycle arrest. Addition of BRAF inhibitors to the arrested cells induces the MAPK cascade leading to increased serine synthesis and folate synthesis. These series of events lead to cell death due to conflicting activation of cellular signaling pathway causing cell cycle arrest from gemcitabine-induced DNA damage and activation of MAPK signaling pathway by BRAF inhibitors. The actual mechanism of cell death is yet unknown.
Figure 12B:
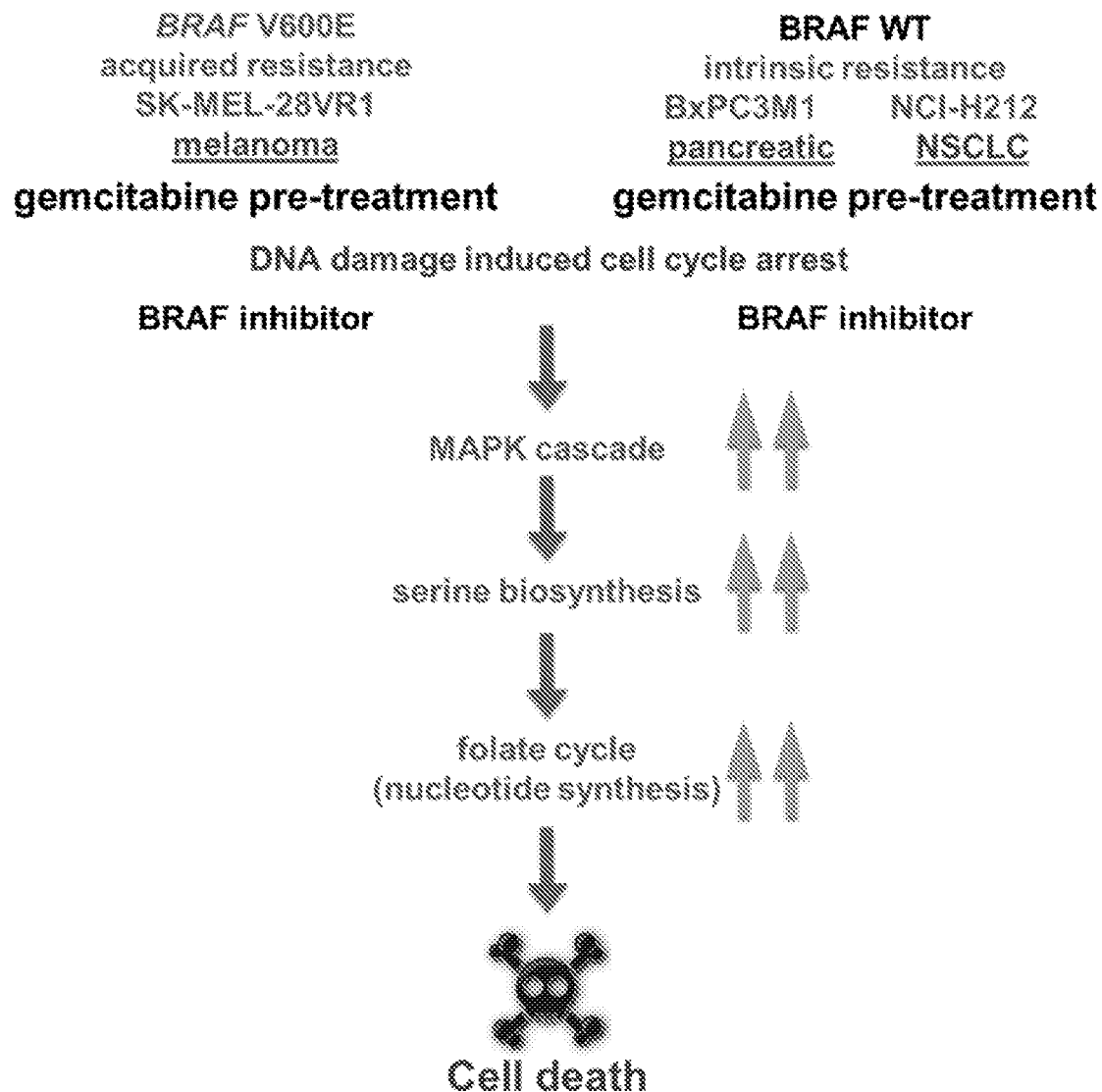

This study has identified serine biosynthesis as a novel, critical determinant of BRAF inhibitor resistance in cancer cells. Additionally, we have demonstrated methotrexate as a sensitizer of melanoma cells to BRAF V600E inhibitors. Future experiments will examine additional inhibitors of the SOG pathway for their efficacies as sensitizers of cells to BRAF inhibitors. Importantly, we have demonstrated gemcitabine pre-treatment as a sensitizer of cancer cells to vemurafenib or dabrafenib, which are BRAF inhibitors. Ultimately, our studies demonstrate the successful use of quantitative proteomic profiling to identify novel protein and pathway targets that can be disrupted to reverse resistance of BRAF V600E and BRAF WT cancer cells to the BRAF inhibitors, vemurafenib or dabrafenib. Without being bound to any particular theory, FIGS. 12A and 12B illustrate the data and pathways described herein. These combinations can be used to treat, for example, pancreatic cancer and melanoma as well as other types of cancers as described herein.

Materials and Methods:

Cell Culture and Chemicals:

Panc1, BxPC3, MiaPaca2, and NCI-H2122 cells were purchased from American Type Culture Collection (ATCC). SK-MEL-28 and 501MEL cells were a generous gift from Dr. Alfonso Bellacosa at Fox Chase Cancer Center (FCCC). Cell line SK-MEL-28VR1 was identified through progressive vemurafenib selection. Briefly, 100,000 SK-MEL-28 cells were exposed to 10 µM vemurafenib for 48 hours, then 20 µM of vemurafenib for 48 hours, then 30 µM of vemurafenib for 48 hours. Surviving cells were pooled and identified as the SK-MEL-28VR1 cell line. Cell line BxPC3M1 was identified through passive selection of BxPC3 cells. Single BxPC3 cells were plated and allowed to grow in sub-clones. Sub-clones with detached phenotypes qualitatively different from the highly adherent BxPC3 parental cells were identified and isolated as BxPC3M cell lines. One such cell line is BxPC3M1. All cell lines were cultured in DMEM/10% FBS (GenDepot) or RPMI1640/10% FBS supplemented (GenDepot) with 2 mM glutamine (Life Technologies; 25030081) and were maintained at 37° C. in 5% $CO_2$. RPMI1640 without glucose, glycine, or serine (Teknova)/10% Dialyzed FBS (Life Technologies; 26400036) were used for serine deprivation studies. Vemurafenib, dabrafenib, encorafenib, methotrexate, camptothecin, and gemcitabine were obtained from Selleckchem. PHGDH siRNA was obtained from Ambion (AM16708), and lipofectamine RNAiMax was obtained from Invitrogen (100014472).

Cell Viability Assays:

For colony formation assays, 400 cells per well were seeded into 24-well plates on day 0. Cells were treated with DMSO or gemcitabine at various doses on day 1 for 24 hours. Gemcitabine was washed out on day 2, vemurafenib, dabrafenib, and methotrexate was added. On day 4, drugs added on day 2 was washed out. Cells were allowed to grow for a subsequent 7 days before being fixed (10% methanol+10% acetic acid) and stained with crystal violet (0.4% in 20% ethanol) for quantitation as previously described.

Mass Spectrometry:

Samples were dried down and re-dissolved in 2.5% ACN/0.1% formic acid for liquid chromatography-tandem mass spectrometry (LC-MS/MS) analysis carried out on a Q-Exactive HF (Thermo Fisher Scientific) coupled with a U3000 RSLCnano HPLC device (Thermo Fisher Scientific). 5 µL of sample were loaded onto a $C_{18}$ trap column (PepMap100; 300-µm i.d.×5 mm, 5-µm particle size, 100 Å; Thermo Fisher Scientific) at a flow rate of 10 µL min$^{-1}$. Peptide separation was carried out on a $C_{18}$ column (ACQUITY UPLC M-Class Peptide CSH C18; 130 Å 1.7 µm 75 µm×250 mm, Waters) at a flow rate of 0.26 µL min$^{-1}$ and the following gradient: 0 to 3 min, 2% B isocratic; 3 to 76 min, 2% to 30% B; 76 to 90 min, 30% to 45% B; 90 to 98 min, 45% to 98% B. Mobile phase A was 0.1% formic acid, and mobile phase B was 0.1% formic acid in 80:20 acetonitrile: water. The runs were analyzed using Progenesis-QI for Proteomics (Nonlinear dynamics). The chromatograms were aligned and the MS/MS data was extracted for peptide identification using Mascot (Matrix Science, London, UK; version 2.5.1). Mascot was set up to search the cRAP database, the custom database including the QMC peptide sequence and SwissProt database (selected for *Homo sapiens*) assuming the digestion enzyme trypsin. Mascot was searched with a fragment ion mass tolerance of 0.06 Da and a parent ion tolerance of 15 PPM. Deamidated of asparagine and glutamine, oxidation of methionine, acetyl of lysine, propionyl of lysine and carbamidomethylation of cysteine were specified in Mascot as variable modifications. The peptides identified using a FDR<1% were extracted and imported back into Progenesis for assignment of the peaks. Only proteins with at least 2 unique peptides and a Mascot score of 20 were used for further analysis. The peptide and protein quantification used a synthetic control peptide for normalization across the samples. All MS runs were performed at the Donald Danforth Plant Science Center for Proteomics and Mass Spectrometry and at the Proteomics and Metabolomics facility at University of Nebraska, Lincoln.

Data Plotting and Statistics:

All proteomic trend plots were constructed using the Evol Science suite (ES). Volcano plotting serves to visually separate data points in two axes by both their expression ratio and their statistical significance. This enables a simple method of determining the most significant, differentially expressed proteins within a given comparison. For each protein, replicate values are gathered from each experiment to be compared to create two distributions of values. Student's T-Test of identical mean is used between the two independent samples of values to compare the distributions and generate a p-value of statistical significance. The –log 10 of the p-value is then taken to provide the Y coordinate, in graphical view. The X coordinate, Ratio, is given by the log 10 of the average of replicate ratio values for a given experiment. Combination Index calculations, Fa-CI plots, and isobolograms were constructed using the Compusyn software program using the Chou-Tulalay method. All plots representing colony formation assays were constructed using the Prism7 software (Graphpad.com). Two-way Anova tests were used to calculate p values.

Western Blotting:

Cells were harvested, washed in PBS and lysed in NP40 lysis buffer (1% NP40/PBS/10% glycerol) with protease and phosphatase inhibitors. Protein concentrations were determined with Total-Protein-Assay-kit (ITSI Biosciences; K-0014-20) and then SDS sample buffer was added to the lysates. 50 ug of boiled lysates was separated by SDS-PAGE and then transferred onto Immobilon P membranes (Millipore; IPVH00010). PHGDH antibodies used for immunoblotting were obtained from Abcam (ab211365). α-Tubulin antibodies used for immunoblotting were obtained from Abcam (ab7291). α-Tubulin was used as a loading control since its expression did not vary in any cell lines or drug treatments.

Figure 15:
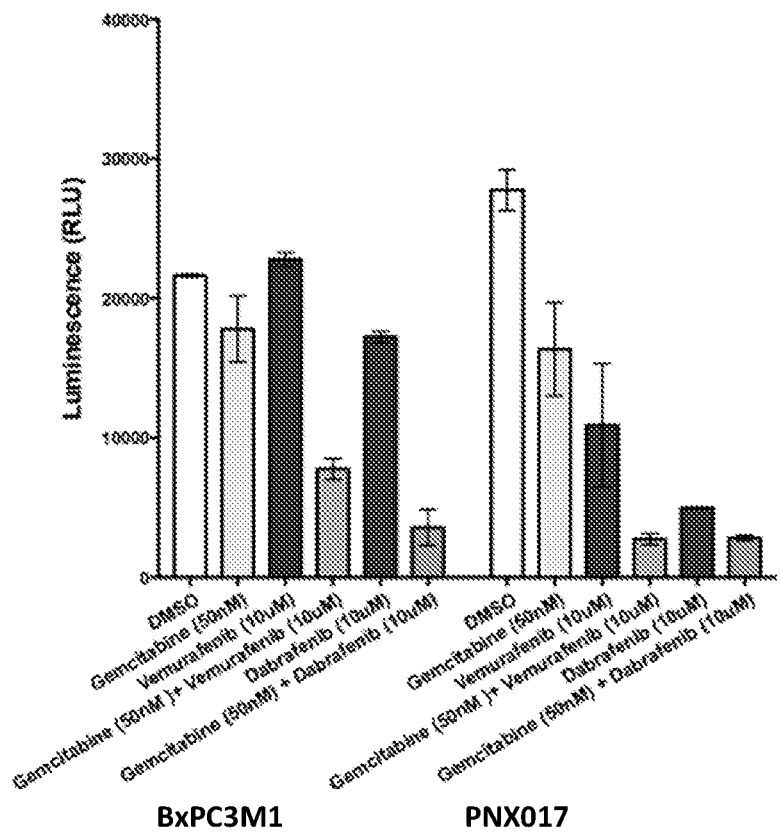
FIG. 15 illustrates gemcitabine sensitized pancreatic cancer patient-derived and ATCC established cell lines to vemurafenib or dabrafenib in 3D-spheroidal growth assays: 20,000 cells plated (Corning 4515 spheroid plates) on day 0, Gemcitabine added on day 2 (all spheroids at least 500 µm in diameter), gemcitabine washed out and BRAF inhibit was added on day 3, CTG3D cell viability assays on day 5 (n=2).
Figure 16A:
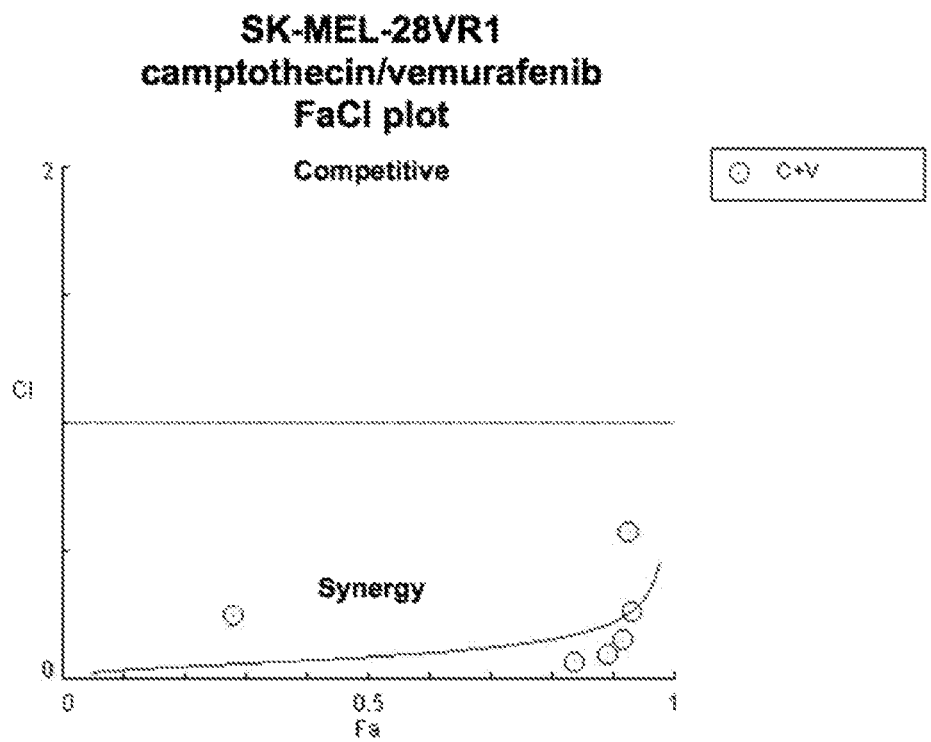
FIG. 16A illustrates the synergistic results from the combination of camptothecin and vemurafenib in SK-MEL-28VR1 metastatic melanoma cells.
Figure 16B:
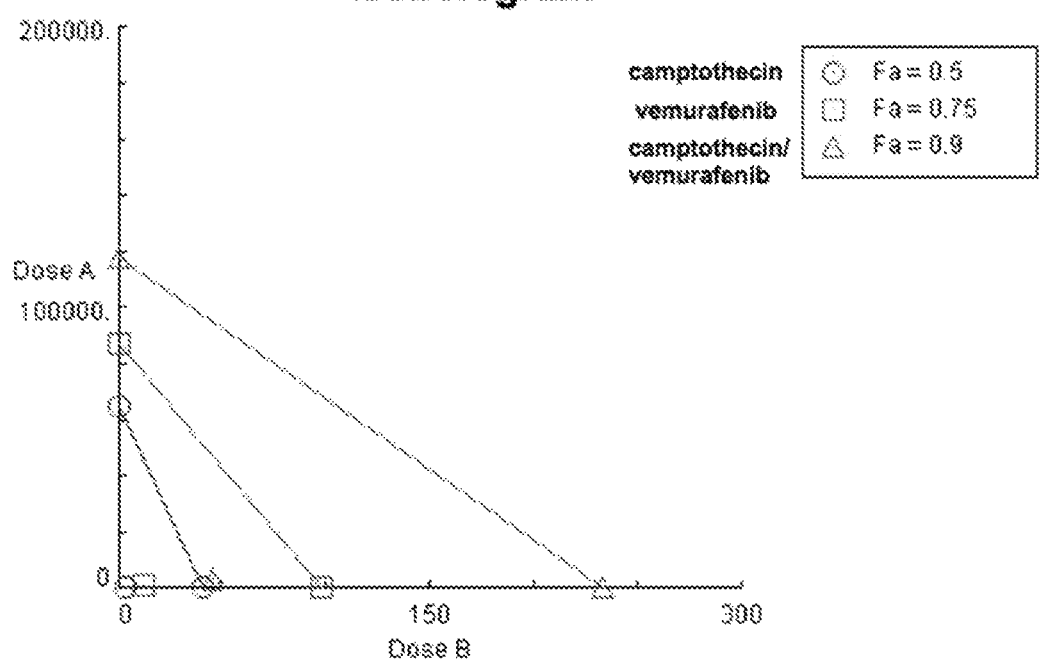
FIG. 16B illustrates the synergistic results from the combination of camptothecin and vemurafenib in SK-MEL-28VR1 metastatic melanoma cells.
Figure 16C:
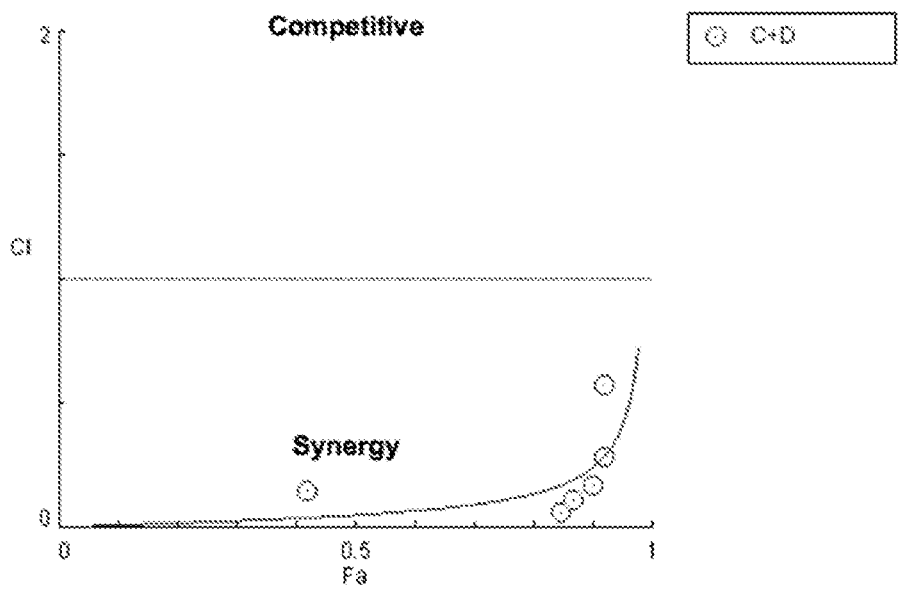
FIG. 16C illustrates the synergistic results from the combination of camptothecin and dabrafenib in SK-MEL-28VR1 metastatic melanoma cells.
Figure 16D:
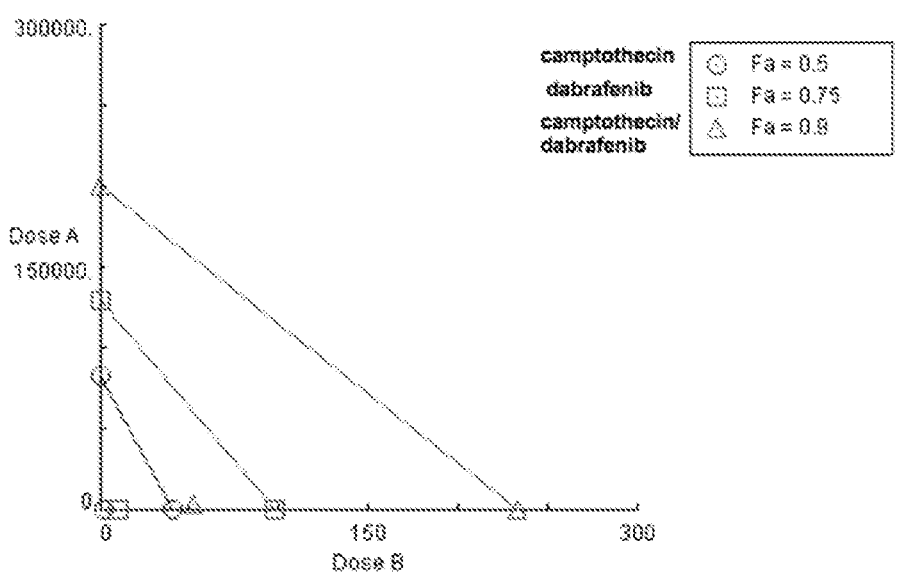
FIG. 16D illustrates the synergistic results from the combination of camptothecin and dabrafenib in SK-MEL-28VR1 metastatic melanoma cells.

Example 3: Gemcitabine Sensitizes Pancreatic Cancer Patient-Derived Cells and ATCC Established Cell Lines to Vemurafenib or Dabrafenib 20,000 cells were plated to grow in a 3D-spheroidal growth assays (Corning 4515 spheroid plates). Two days later when all spheroids were at least 500 µm in diameter, gemcitabine was added. Gemcitabine was washed out the following day and the BRAF inhibitor was added on day 3 (3 days post-plating). CTG3D cell viability assays were performed 5-days post plating (i.e, on day 5, n=2). As the data in FIG. 15 illustrates, the pre-treatment of the cells with a DNA damaging agent, such as gemcitabine, renders the pancreatic cancer cells sensitive to BRAF inhibitors and not only inhibits their growth, but leads to cell death. This was a surprising and unexpected effect that these cells could be killed with this combination.

Example 4: Camptothecin Exhibits Synergy with BRAF Inhibitors

Constant ratio combination index (CI) calculations showed significant synergy between camptothecin and dabrafenib or vemurafenib in SK-MEL-28VR1 metastatic melanoma cells (FIG. 16). Camptothecin is a topoisomerase 1 inhibitor and a DNA damaging agent. Colony formation assays were set up to accommodate Chou Talalay constant ratio CI calculations. The starting dose of single camptothecin treatment was 150 nM, vemurafenib was 100 µM, and dabrafenib was 100 µM. The dose was progressively reduced in a constant ratio by 1/2, 1/4, 1/8, 1/16, and 1/32 in consecutive wells in series triplicates. For the combination treatments, the ratio of captothecin to either BRAF inhibitor was 1 to 66.7 with 150 nM as the starting dose of captothecin and 10 µM as the starting dose of the BRAF inhibitor. 400 cells were plated per well of 24-well plates on day 0. Camptothecin was added on day 1 and washed out on day 2. Either BRAF inhibitor vemurafenib (FIGS. 16A and 16B) or dabrafenib (FIGS. 16C and 16D) was added following camptothecin wash on day 2. BRAF inhibitor was washed out on day 4 and colonies were allowed to form for 7 days before being fixed (10% methanol+10% acetic acid) and stained with crystal violet (0.4% in 20% ethanol) for quantitation as previously described. FIG. 16A is a constant ratio FaCI plot showing synergy between camptothecin and vemurafenib. FIG. 16B is a constant ratio isobologram displaying synergy between camptothecin and vemurafenib. FIG. 16C is a constant ratio FaCI plot showing synergy between camptothecin and dabrafenib. FIG. 16D is a constant ratio isobologram displaying synergy between camptothecin and dabrafenib. In totality, these results clearly shows the therapeutic potential of both the camptothecin+vemurafenib and the camptothecin+dabrafenib combination treatments against metastatic melanoma. The synergy of a combination of a quinoline alkaloid, such as camptothecin, and a BRAF inhibitor, such as those described herein, was surprising and unexpected.

Example 5: Methotrexate Exhibits Synergy with Encorafenib

Figure 17A:
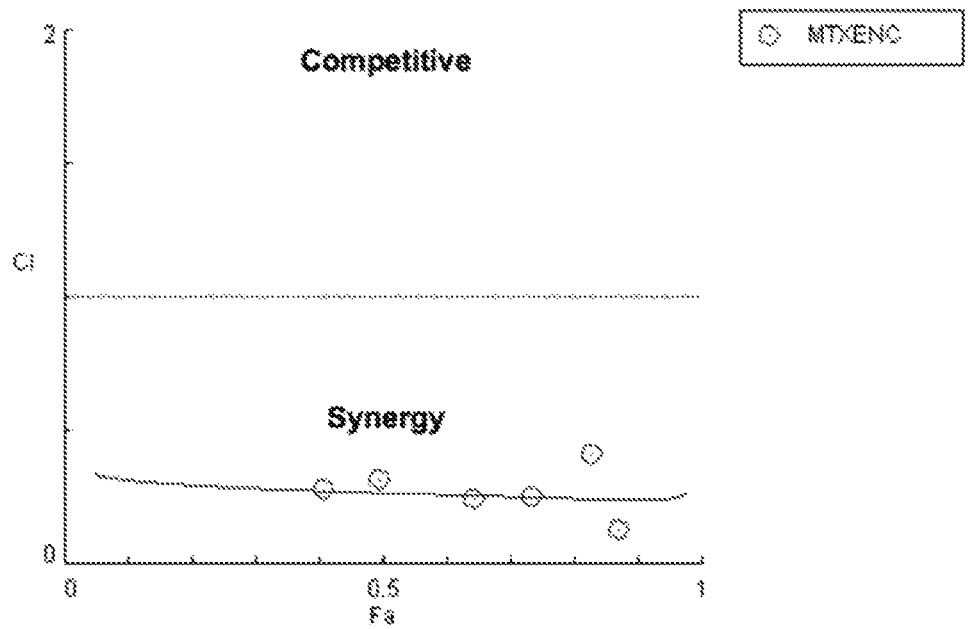
FIG. 17A illustrates the synergistic results from the combination of methotrexate and encorafenib in SK-MEL-28VR1 metastatic melanoma cells.
Figure 17B:
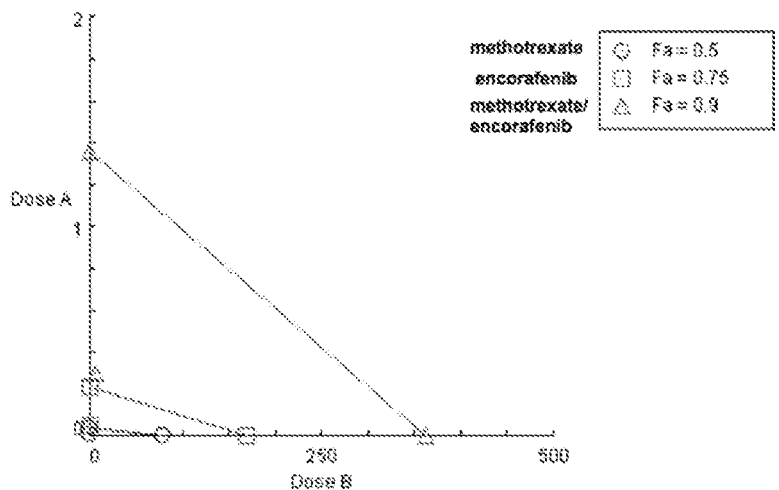
FIG. 17B illustrates the synergistic results from the combination of methotrexate and encorafenib in SK-MEL-28VR1 metastatic melanoma cells.

Constant ratio combination index (CI) calculations obtained from 3D spheroidal growth assays showed significant synergy between methotrexate and encorafenib in SK-MEL-28VR1 metastatic melanoma cells (FIG. 17). Methotrexate is an antifolate and a DNA damaging agent. Encorafenib is a BRAF inhibitor known to induce senescence and autophagy in BRAF V600E mutant melanoma cells. As with other BRAF inhibitors, encorafenib paradoxically activates the MAPK pathway in BRAF WT backgrounds. Spheroidal growth assays were set up to accommodate Chou Talalay constant ratio CI calculations. The starting dose of single methotrexate treatment was 200 nM and encorafenib was 100 µM. The dose was progressively reduced in a constant ratio by 1/2, 1/4, 1/8, 1/16, and 1/32 in consecutive wells in series triplicates. For the combination treatments, the ratio of methotrexate to encorafenib was 1 to 25 with 200 nM as the starting dose of methotrexate and 5 µM as the starting dose of encorafenib. 5,000 cells were plated per well of 96-well spheroid plates (Corning 4515). Once spheroidal growth reached at least 500 µm in diameter, methotrexate and encorafenib was added. Cells were incubated for 96 hours. Subsequently, CTG3D assays were performed to assess spheroidal growth. FIG. 17A is a constant ratio FaCI plot showing synergy between methotrexate and encorafenib. FIG. 17B is a constant ratio isobologram displaying synergy between methotrexate and encorafenib. In totality, FIG. 17 clearly shows the therapeutic potential of methotrexate+encorafenib combination treatments against metastatic melanoma. The synergy of a combination of methotrexate and a BRAF inhibitor, such as those described herein, was surprising and unexpected.

Figure 18A:
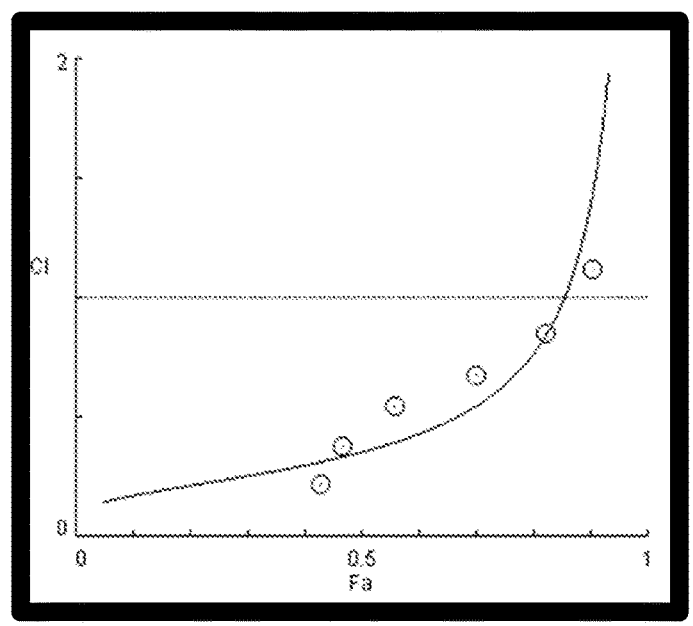
FIG. 18A, FIG. 18B, and FIG. 18C illustrate the synergistic results from the combination of gemcitabine, paclitaxel, and BRAF inhibitors encorafenib or dabrafenib.
Figure 18B:
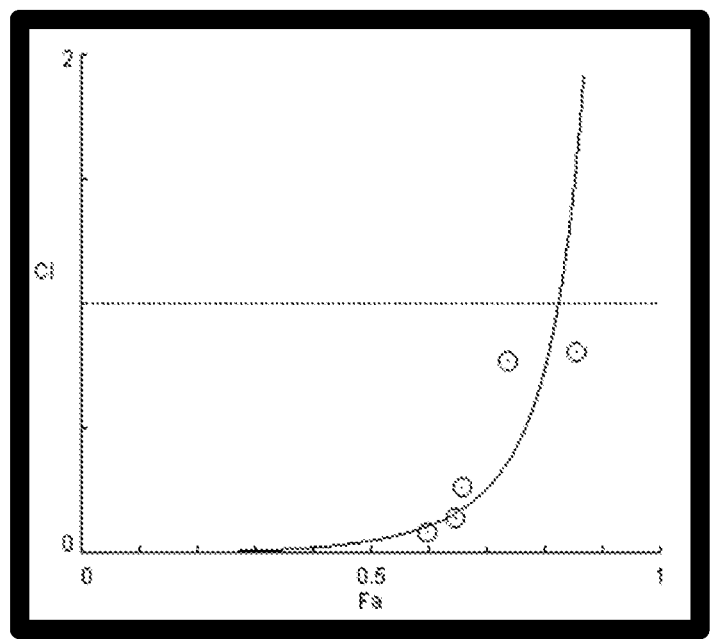
Figure 18C:
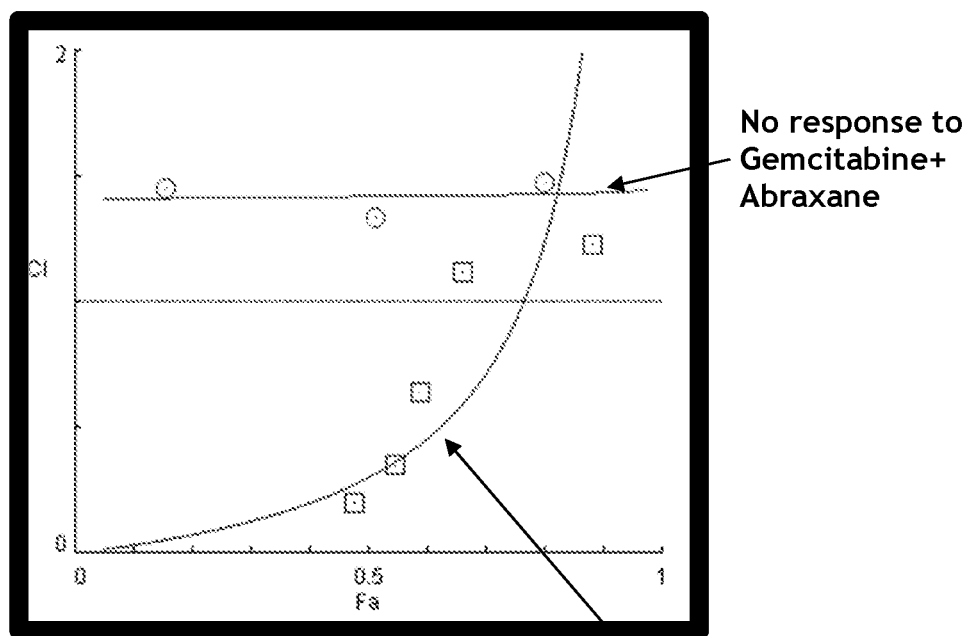

Example 6: Combination of BRAF Inhibitors, DNA Damaging Agents, and Taxanes can be Used to Treat Cancers that were Previously Non-Responsive to Treatments Constant ratio combination index (CI) calculations showed significant synergy between Gemcitabine, paclitaxel/Abraxane, and BRAF inhibitors (dabrafenib or encorafenib) in human pancreatic cancer cell lines (BxPCM1; FIG. 18A), mouse KPC pancreatic cancer model cell lines (KPC FC 1242; FIG. 18B), or patient derived pancreatic cancer cell lines (PNX001; FIG. 18C). Paclitaxel, sold as Taxol, is a chemotherapeutic used to treat multiple cancers including pancreatic, skin, lung, breast, cervical, and ovarian cancers. Abraxane is the trade name for paclitaxel bound to albumin particles (nab-paclitaxel). The gemcitabine+Abraxane combination is currently the first-line therapeutic given to >60% of unresectable pancreatic cancer patients in the US. Colony formation assays were set up to accommodate Chou Talalay constant ratio CI calculations.

For BxPC3M1 (FIG. 18A), the starting dose of single gemcitabine treatment was 150 nM, paclitaxel was 40 nM, and encorafenib was 100 µM. The dose was progressively reduced in a constant ratio by 1/2, 1/4, 1/8, 1/16, and 1/32 in consecutive wells in series triplicates. For the combination treatments, the ratio of gemcitabine to encorafenib was 1 to 200 with 25 nM as the starting dose of gemcitabine and 5 µM as the starting dose of encorafenib. The ratio of paclitaxel to encorafenib was 1 to 250, with 20 nM as the starting dose of paclitaxel and 5 µM as the starting dose of encorafenib.

For KPC FC 1242 (FIG. 18B), the starting dose of single gemcitabine treatment was 50 nM, paclitaxel was 100 nM, and dabrafenib was 100 µM. The dose was progressively reduced in a constant ratio by 1/2, 1/4, 1/8, 1/16, and 1/32 in consecutive wells in series triplicates. For the combination treatments, the ratio of gemcitabine to dabrafenib was 1 to 400 with 25 nM as the starting dose of gemcitabine and 10 µM as the starting dose of dabrafenib. The ratio of paclitaxel to dabrafenib was 1 to 500, with 20 nM as the starting dose of paclitaxel and 10 µM as the starting dose of dabrafenib.

For PNX001 (FIG. 18C), the starting dose of single gemcitabine treatment was 10 nM, Abraxane was 20 nM, and dabrafenib was 100 µM. The dose was progressively reduced in a constant ratio by 1/2, 1/4, 1/8, 1/16, and 1/32 in consecutive wells in series triplicates. For the combination treatments, the ratio of gemcitabine to dabrafenib was 1 to 1000 with 10 nM as the starting dose of gemcitabine and 10 µM as the starting dose of dabrafenib. The ratio of Abraxane to dabrafenib was 1 to 4000, with 2.5 nM as the starting dose of Abraxane and 10 µM as the starting dose of dabrafenib. The gemcitabine and Abraxane doses were repeated to obtain the dual treatment curve (FIG. 18C). 400 cells were plated per well of 24-well plates on day 0. Gemcitabine and paclitaxel/Abraxane was added on day 1 and washed out on day 2.

Either the BRAF inhibitor encorafenib (FIG. 18A) or dabrafenib (FIGS. 18B and 18C) was added following gemcitabine and paclitaxel/Abraxane wash-out on day 2. The BRAF inhibitor was washed out on day 4 and colonies were allowed to form for 7 days before being fixed (10% methanol+10% acetic acid) and stained with crystal violet (0.4% in 20% ethanol) for quantitation as previously described. FIG. 18A is a constant ratio FaCI plot showing synergy between gemcitabine, paclitaxel, and encorafenib in a human pancreatic cancer cell line (BxPC3M1). FIG. 18B is a constant ratio FaCI plot showing synergy between gemcitabine, paclitaxel, and dabrafenib in a mouse KPC pancreatic cancer cell line (KPC FC 1242). FIG. 18C is a constant ratio FaCI plot showing synergy between gemcitabine, Abraxane, and dabrafenib in a human patient-derived pancreatic cancer cell line (PNX001). Importantly, FIG. 18C exhibits a patient-derived cell line that does not respond to the gemcitabine+Abraxane treatments but does respond to the gemcitabine+Abraxane+dabrafenib combination treatments. In totality, these results clearly show the therapeutic potential of the gemcitabine+paclitaxel/Abraxane+BRAF inhibitor combination treatments against pancreatic cancer. The synergy of a combination of a nucleoside analog and DNA damaging agent, such as gemcitabine, a taxane, such as paclitaxel/Abraxane, and a BRAF inhibitor, such as those described herein, was surprising and unexpected.

Figure 19A:
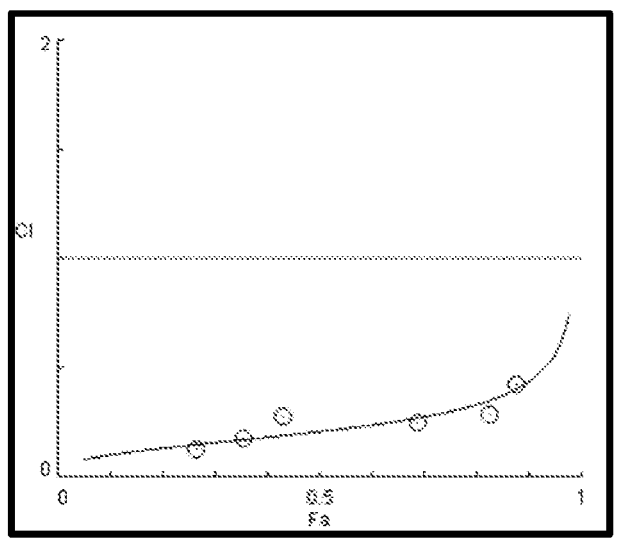
FIG. 19A illustrates the synergistic results from the combination of gemcitabine, and BRAF inhibitor GDC0879 in SK-MEL-28VR1 metastatic melanoma cells.
Figure 19B:
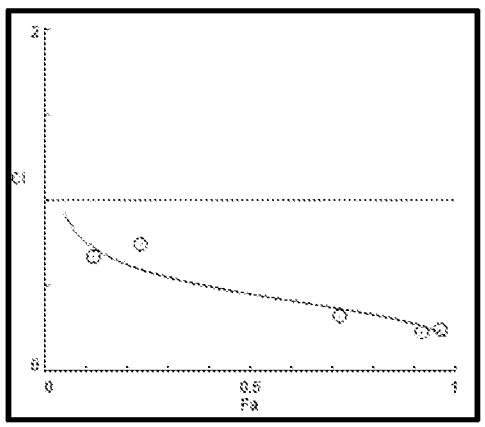
FIG. 19B illustrates the synergistic results from the combination of gemcitabine, and BRAF inhibitor AD80 in SK-MEL-28VR1 metastatic melanoma cells.
Figure 20A:
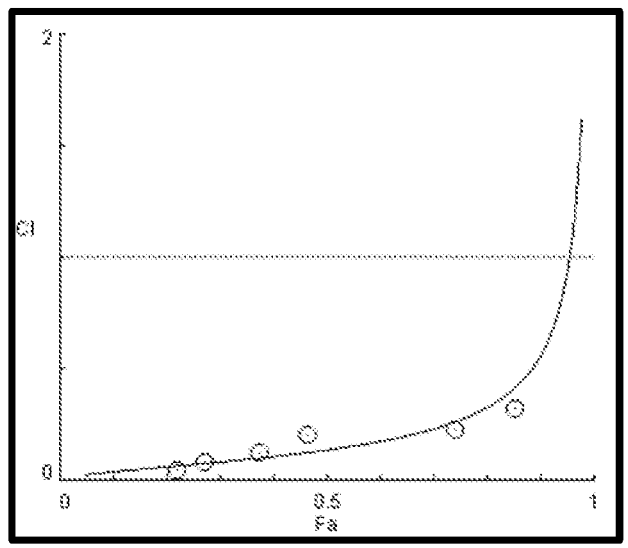
FIG. 20A illustrates the synergistic results from the combination of gemcitabine, and BRAF inhibitor GDC0879 in 501mel metastatic melanoma cells.
Figure 20B:
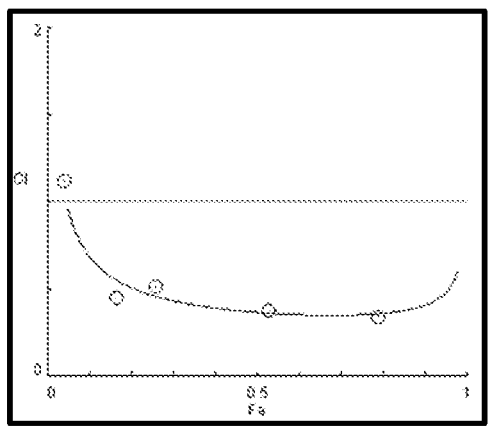
FIG. 20B illustrates the synergistic results from the combination of gemcitabine, and BRAF inhibitor AD80 in 501mel metastatic melanoma cells.
Figure 21A:
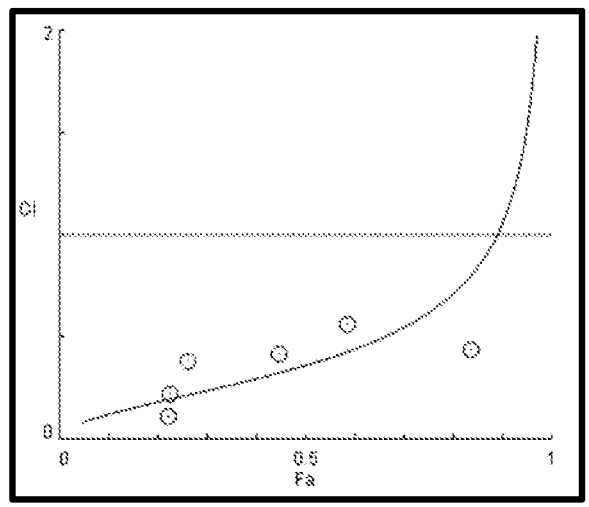
FIG. 21A illustrates the synergistic results from the combination of gemcitabine, and BRAF inhibitor GDC0879 in Panc1 pancreatic cancer cells.
Figure 21B:
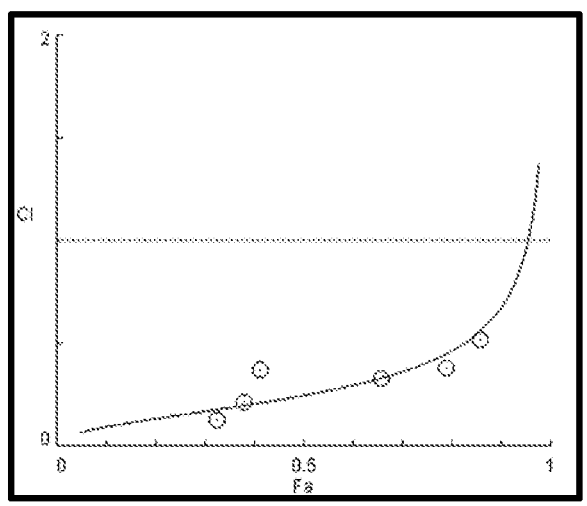
FIG. 21B illustrates the synergistic results from the combination of gemcitabine, and BRAF inhibitor AD80 in Panc1 pancreatic cancer cells.
Figure 22A:
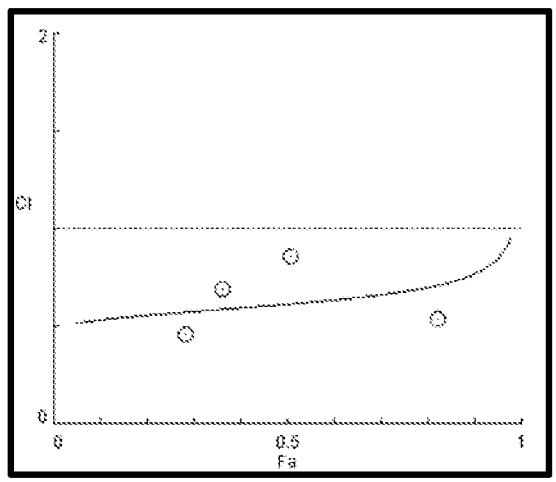
FIG. 22A illustrates the synergistic results from the combination of gemcitabine, and BRAF inhibitor GDC0879 in BxPC3M1 pancreatic cancer cells.
Figure 22B:
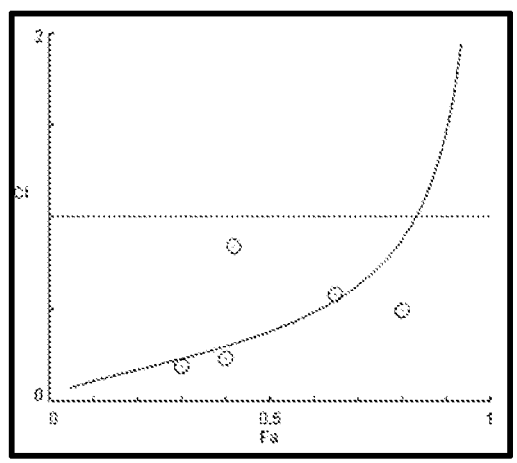
FIG. 22B illustrates the synergistic results from the combination of gemcitabine, and BRAF inhibitor AD80 in BxPC3M1 pancreatic cancer cells.

Example 7: Combination of BRAF Inhibitors and DNA Damaging Agents can be Used to Treat Cancers that were Previously Non-Responsive to Treatments Constant ratio combination index (CI) calculations showed significant synergy between Gemcitabine and BRAF inhibitors GDC0879 or AD80 in metastatic melanoma cell lines (SK-MEL-28VR1; FIGS. 19A and 19B, 501mel; FIGS. 20A and 20B) and pancreatic cancer cell lines (Panc1; FIGS. 21A and 21B, BxPC3M1; FIGS. 22A and 22B).

For SK-MEL-28VR1 (FIG. 19A), the starting dose of single gemcitabine treatment was 150 nM and GDC0879 was 100 µM. The dose was progressively reduced in a constant ratio by 1/2, 1/4, 1/8, 1/16, and 1/32 in consecutive wells in series triplicates. For the combination treatments, the ratio of gemcitabine to GDC0879 was 1 to 200 with 25 nM as the starting dose of gemcitabine and 5 µM as the starting dose of GDC0879.

For SK-MEL-28VR1 (FIG. 19B), the starting dose of single gemcitabine treatment was 150 nM and AD80 was 100 µM. The dose was progressively reduced in a constant ratio by 1/2, 1/4, 1/8, 1/16, and 1/32 in consecutive wells in series triplicates. For the combination treatments, the ratio of gemcitabine to AD80 was 1 to 200 with 25 nM as the starting dose of gemcitabine and 5 µM as the starting dose of AD80.

For 501mel (FIG. 20A), the starting dose of single gemcitabine treatment was 150 nM and GDC0879 was 100 µM. The dose was progressively reduced in a constant ratio by 1/2, 1/4, 1/8, 1/16, and 1/32 in consecutive wells in series triplicates. For the combination treatments, the ratio of gemcitabine to GDC0879 was 1 to 200 with 25 nM as the starting dose of gemcitabine and 5 µM as the starting dose of GDC0879.

For 501mel (FIG. 20B), the starting dose of single gemcitabine treatment was 150 nM and AD80 was 100 µM. The dose was progressively reduced in a constant ratio by 1/2, 1/4, 1/8, 1/16, and 1/32 in consecutive wells in series triplicates. For the combination treatments, the ratio of gemcitabine to AD80 was 1 to 200 with 25 nM as the starting dose of gemcitabine and 5 µM as the starting dose of AD80.

For Panc1 (FIG. 21A), the starting dose of single gemcitabine treatment was 150 nM and GDC0879 was 100 µM. The dose was progressively reduced in a constant ratio by 1/2, 1/4, 1/8, 1/16, and 1/32 in consecutive wells in series triplicates. For the combination treatments, the ratio of gemcitabine to GDC0879 was 1 to 200 with 25 nM as the starting dose of gemcitabine and 5 µM as the starting dose of GDC0879.

For Panc1 (FIG. 21B), the starting dose of single gemcitabine treatment was 150 nM and AD80 was 100 µM. The dose was progressively reduced in a constant ratio by 1/2, 1/4, 1/8, 1/16, and 1/32 in consecutive wells in series triplicates. For the combination treatments, the ratio of gemcitabine to AD80 was 1 to 200 with 25 nM as the starting dose of gemcitabine and 5 µM as the starting dose of AD80.

For BxPC3M1 (FIG. 21A), the starting dose of single gemcitabine treatment was 150 nM and GDC0879 was 100 µM. The dose was progressively reduced in a constant ratio by 1/2, 1/4, 1/8, 1/16, and 1/32 in consecutive wells in series triplicates. For the combination treatments, the ratio of gemcitabine to GDC0879 was 1 to 200 with 25 nM as the starting dose of gemcitabine and 5 µM as the starting dose of GDC0879.

For BxPC3M1 (FIG. 21B), the starting dose of single gemcitabine treatment was 150 nM and AD80 was 100 µM. The dose was progressively reduced in a constant ratio by 1/2, 1/4, 1/8, 1/16, and 1/32 in consecutive wells in series triplicates. For the combination treatments, the ratio of gemcitabine to AD80 was 1 to 200 with 25 nM as the starting dose of gemcitabine and 5 µM as the starting dose of AD80.

Either the BRAF inhibitor GDC0879 (FIGS. 19A, 20A, 21A, and 22A) or AD80 (FIGS. 19B, 20B, 21B, and 22B) was added following gemcitabine wash-out on day 2. The BRAF inhibitor was washed out on day 4 and colonies were allowed to form for 7 days before being fixed (10% methanol+10% acetic acid) and stained with crystal violet (0.4% in 20% ethanol) for quantitation as previously described. FIG. 19A is a constant ratio FaCI plot showing synergy between gemcitabine and GDC0879 in a human metastatic melanoma cell line (SK-MEL-28VR1). FIG. 19B is a constant ratio FaCI plot showing synergy between gemcitabine and AD80 in a human metastatic melanoma cell line (SK-MEL-28VR1). FIG. 20A is a constant ratio FaCI plot showing synergy between gemcitabine and GDC0879 in a human metastatic melanoma cell line (501mel). FIG. 20B is a constant ratio FaCI plot showing synergy between gemcitabine and AD80 in a human metastatic melanoma cell line (501mel). FIG. 21A is a constant ratio FaCI plot showing synergy between gemcitabine and GDC0879 in a human pancreatic cancer cell line (Panc1). FIG. 21B is a constant ratio FaCI plot showing synergy between gemcitabine and AD80 in a human pancreatic cancer cell line (Panc1). FIG. 22A is a constant ratio FaCI plot showing synergy between gemcitabine and GDC0879 in a human pancreatic cancer cell line (BxPC3M1). FIG. 22B is a constant ratio FaCI plot showing synergy between gemcitabine and AD80 in a human pancreatic cancer cell line (BxPC3M1). In totality, these results clearly show the therapeutic potential of the gemcitabine+BRAF inhibitor combination treatments against metastatic melanoma and pancreatic cancer. The synergy in being able to inhibit the growth non-responsive tumor cell lines of a combination of a nucleoside analog and DNA damaging agent, such as gemcitabine, and a BRAF inhibitor, such as those described herein, was surprising and unexpected.

Figure 23A:
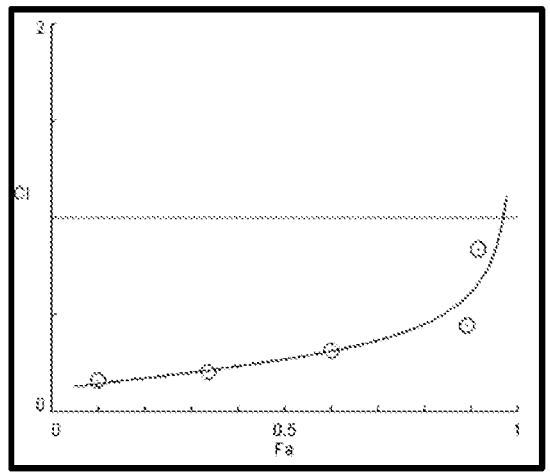
FIG. 23A illustrates the synergistic results from the combination of gemcitabine, and CRAF inhibitor ZM336372 in SK-MEL-28VR1 metastatic melanoma cells.
Figure 23B:
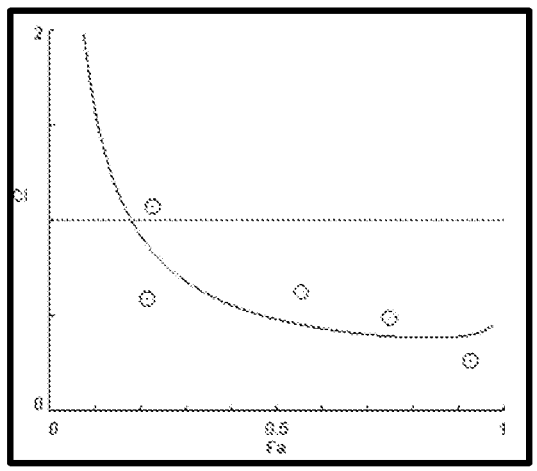
FIG. 23B illustrates the synergistic results from the combination of gemcitabine, and CRAF inhibitor NVPBHG712 in SK-MEL-28VR1 metastatic melanoma cells.
Figure 24A:
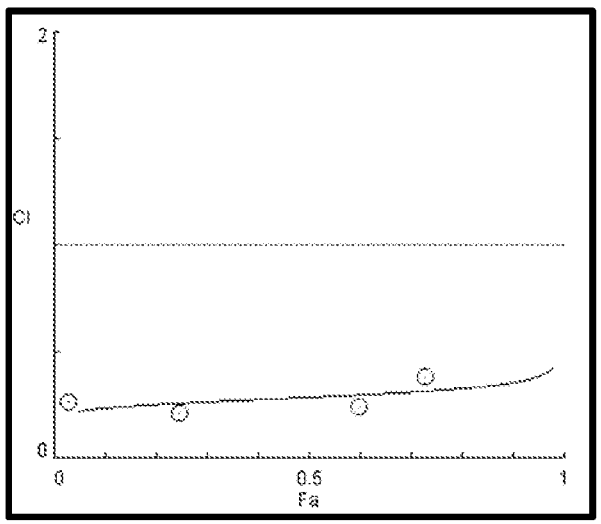
FIG. 24A illustrates the synergistic results from the combination of gemcitabine, and CRAF inhibitor ZM336372 in 501mel metastatic melanoma cells.
Figure 24B:
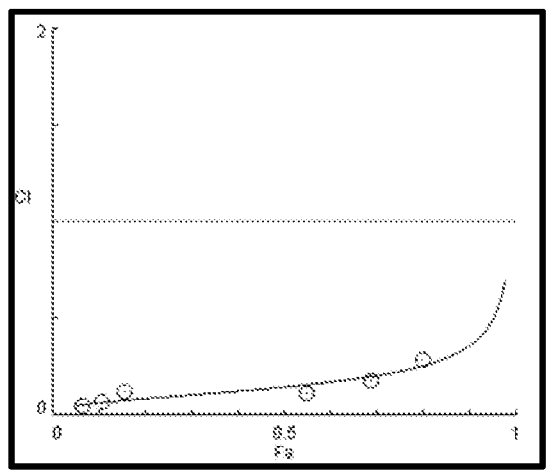
FIG. 24B illustrates the synergistic results from the combination of gemcitabine, and CRAF inhibitor NVPBHG712 in 501mel metastatic melanoma cells.
Figure 25A:
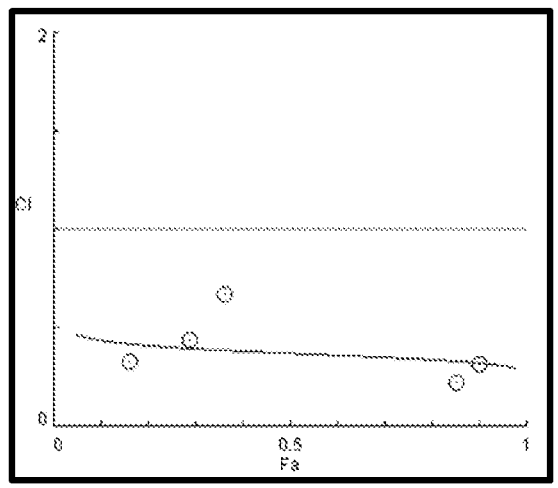
FIG. 25A illustrates the synergistic results from the combination of gemcitabine, and CRAF inhibitor ZM336372 in Panc1 pancreatic cancer cells.
Figure 25B:
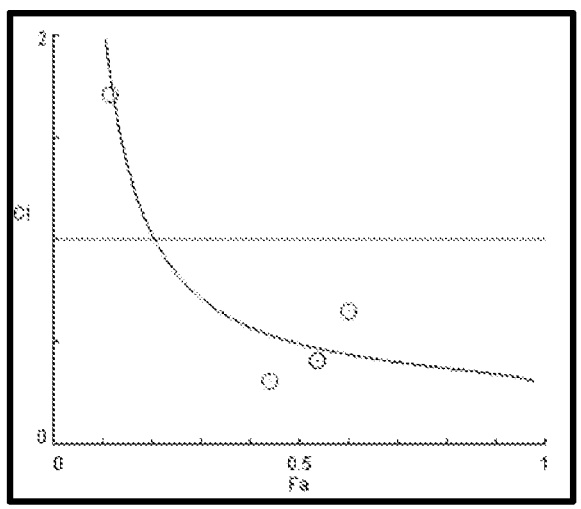
FIG. 25B illustrates the synergistic results from the combination of gemcitabine, and CRAF inhibitor NVPBHG712 in Panc1 pancreatic cancer cells.
Figure 26A:
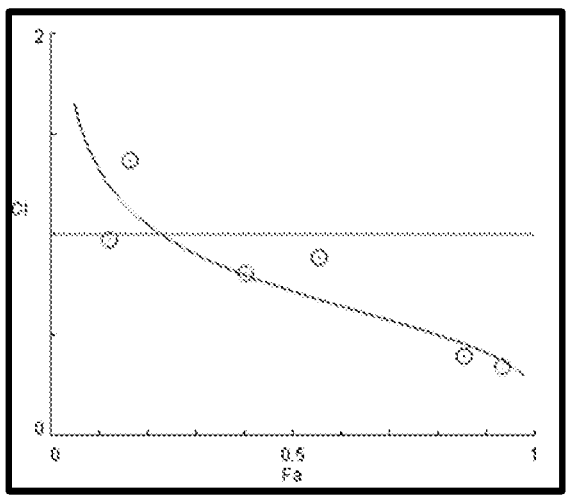
FIG. 26A illustrates the synergistic results from the combination of gemcitabine, and CRAF inhibitor ZM336372 in BxPC3M1 pancreatic cancer cells.
Figure 26B:
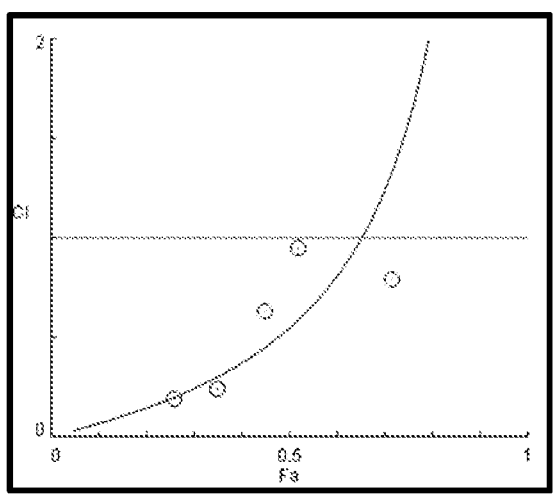
FIG. 26B illustrates the synergistic results from the combination of gemcitabine, and CRAF inhibitor NVPBHG712 in BxPC3M1 pancreatic cancer cells.

Example 8: Combination of CRAF Inhibitors and DNA Damaging Agents can be Used to Treat Cancers that were Previously Non-Responsive to Treatments The following example demonstrates that CRAF inhibitors can also be used to treat cancers that were previously non-responsive to treatments. Constant ratio combination index (CI) calculations showed significant synergy between Gemcitabine and CRAF inhibitors ZM336372 and NVPBHG712 in metastatic melanoma cell lines (SK-MEL-28VR1; FIGS. 23A and 23B, and 501mel; FIGS. 24A, and 24B) and pancreatic cancer cell lines (Panc1; FIGS. 25A and 25B, BxPC3M1; FIGS. 26A and 26B).

For SK-MEL-28VR1 (FIG. 23A), the starting dose of single gemcitabine treatment was 150 nM and ZM336372 was 100 µM. The dose was progressively reduced in a constant ratio by 1/2, 1/4, 1/8, 1/16, and 1/32 in consecutive wells in series triplicates. For the combination treatments, the ratio of gemcitabine to ZM336372 was 1 to 200 with 25 nM as the starting dose of gemcitabine and 5 µM as the starting dose of ZM336372.

For SK-MEL-28VR1 (FIG. 23B), the starting dose of single gemcitabine treatment was 150 nM and NVPBHG712 was 100 µM. The dose was progressively reduced in a constant ratio by 1/2, 1/4, 1/8, 1/16, and 1/32 in consecutive wells in series triplicates. For the combination treatments, the ratio of gemcitabine to NVPBHG712 was 1 to 200 with 25 nM as the starting dose of gemcitabine and 5 µM as the starting dose of NVPBHG712.

For 501mel (FIG. 24A), the starting dose of single gemcitabine treatment was 150 nM and ZM336372 was 100 µM. The dose was progressively reduced in a constant ratio by 1/2, 1/4, 1/8, 1/16, and 1/32 in consecutive wells in series triplicates. For the combination treatments, the ratio of gemcitabine to ZM336372 was 1 to 200 with 25 nM as the starting dose of gemcitabine and 5 µM as the starting dose of ZM336372.

For 501mel (FIG. 24B), the starting dose of single gemcitabine treatment was 150 nM and NVPBHG712 was 100 µM. The dose was progressively reduced in a constant ratio by 1/2, 1/4, 1/8, 1/16, and 1/32 in consecutive wells in series triplicates. For the combination treatments, the ratio of gemcitabine to NVPBHG712 was 1 to 200 with 25 nM as the starting dose of gemcitabine and 5 µM as the starting dose of NVPBHG712.

For Panc1 (FIG. 25A), the starting dose of single gemcitabine treatment was 150 nM and ZM336372 was 100 µM. The dose was progressively reduced in a constant ratio by 1/2, 1/4, 1/8, 1/16, and 1/32 in consecutive wells in series triplicates. For the combination treatments, the ratio of gemcitabine to ZM336372 was 1 to 200 with 25 nM as the starting dose of gemcitabine and 5 µM as the starting dose of ZM336372.

For Panc1 (FIG. 25B), the starting dose of single gemcitabine treatment was 150 nM and NVPBHG712 was 100 µM. The dose was progressively reduced in a constant ratio by 1/2, 1/4, 1/8, 1/16, and 1/32 in consecutive wells in series triplicates. For the combination treatments, the ratio of gemcitabine to NVPBHG712 was 1 to 200 with 25 nM as the starting dose of gemcitabine and 5 µM as the starting dose of NVPBHG712.

For BxPC3M1 (FIG. 26A), the starting dose of single gemcitabine treatment was 150 nM and ZM336372 was 100 µM. The dose was progressively reduced in a constant ratio by 1/2, 1/4, 1/8, 1/16, and 1/32 in consecutive wells in series triplicates. For the combination treatments, the ratio of gemcitabine to ZM336372 was 1 to 200 with 25 nM as the starting dose of gemcitabine and 5 µM as the starting dose of ZM336372.

For BxPC3M1 (FIG. 26B), the starting dose of single gemcitabine treatment was 150 nM and NVPBHG712 was 100 µM. The dose was progressively reduced in a constant ratio by 1/2, 1/4, 1/8, 1/16, and 1/32 in consecutive wells in series triplicates. For the combination treatments, the ratio of gemcitabine to NVPBHG712 was 1 to 200 with 25 nM as the starting dose of gemcitabine and 5 µM as the starting dose of NVPBHG712.

Either the CRAF inhibitor ZM336372 (FIGS. 23A, 24A, 25A, and 26A) or NVPBHG712 (FIGS. 23B, 24B, 25B, and 26B) was added following gemcitabine wash-out on day 2. The CRAF inhibitor was washed out on day 4 and colonies were allowed to form for 7 days before being fixed (10% methanol+10% acetic acid) and stained with crystal violet (0.4% in 20% ethanol) for quantitation as previously described. FIG. 23A is a constant ratio FaCI plot showing synergy between gemcitabine and ZM336372 in a human metastatic melanoma cell line (SK-MEL-28VR1). FIG. 23B is a constant ratio FaCI plot showing synergy between gemcitabine and NVPBHG712 in a human metastatic melanoma cell line (SK-MEL-28VR1). FIG. 24A is a constant ratio FaCI plot showing synergy between gemcitabine and ZM336372 in a human metastatic melanoma cell line (501mel). FIG. 24B is a constant ratio FaCI plot showing synergy between gemcitabine and NVPBHG712 in a human metastatic melanoma cell line (501mel). FIG. 25A is a constant ratio FaCI plot showing synergy between gemcitabine and ZM336372 in a human pancreatic cancer cell line (Panc1). FIG. 25B is a constant ratio FaCI plot showing synergy between gemcitabine and NVPBHG712 in a human pancreatic cancer cell line (Panc1). FIG. 26A is a constant ratio FaCI plot showing synergy between gemcitabine and ZM336372 in a human pancreatic cancer cell line (BxPC3M1). FIG. 26B is a constant ratio FaCI plot showing synergy between gemcitabine and NVPBHG712 in a human pancreatic cancer cell line (BxPC3M1). In totality, these results clearly show the therapeutic potential of the gemcitabine+CRAF inhibitor combination treatments against metastatic melanoma and pancreatic cancer. The synergy of a combination of a nucleoside analog and DNA damaging agent, such as gemcitabine, and a CRAF inhibitor, such as those described herein, was surprising and unexpected.

Figure 27A:
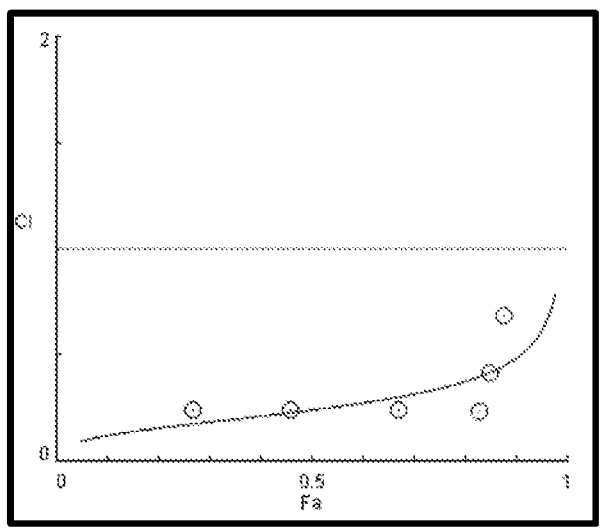
FIG. 27A illustrates the synergistic results from the combination of gemcitabine, and pan-RAF inhibitor RAF265 in SK-MEL-28VR1 metastatic melanoma cells.
Figure 27B:
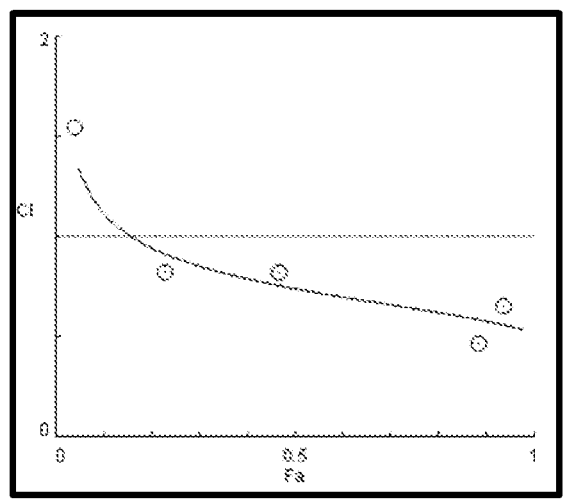
FIG. 27B illustrates the synergistic results from the combination of gemcitabine, and pan-RAF inhibitor TAK632 in SK-MEL-28VR1 metastatic melanoma cells.
Figure 28A:
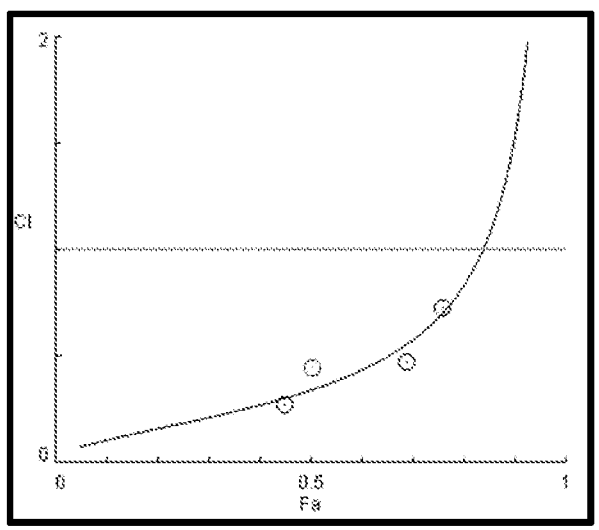
FIG. 28A illustrates the synergistic results from the combination of gemcitabine, and pan-RAF inhibitor RAF265 in 501mel metastatic melanoma cells.
Figure 28B:
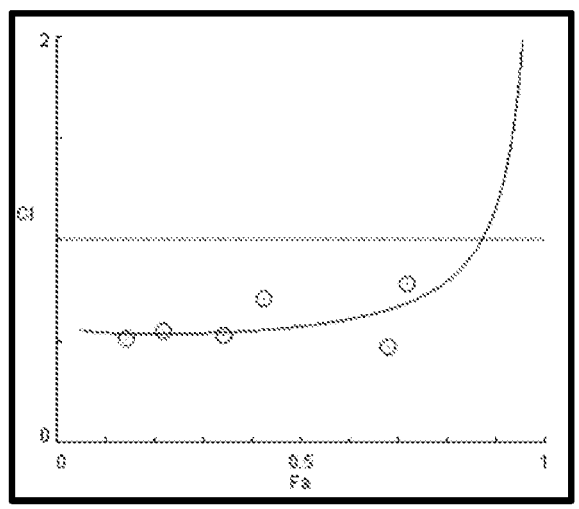
FIG. 28B illustrates the synergistic results from the combination of gemcitabine, and pan-RAF inhibitor TAK632 in 501mel metastatic melanoma cells.
Figure 29A:
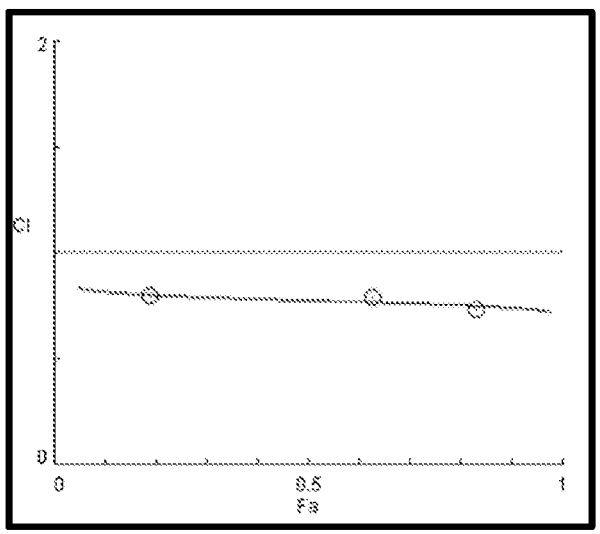
FIG. 29A illustrates the synergistic results from the combination of gemcitabine, and pan-RAF inhibitor RAF265 in Panc1 pancreatic cancer cells.
Figure 29B:
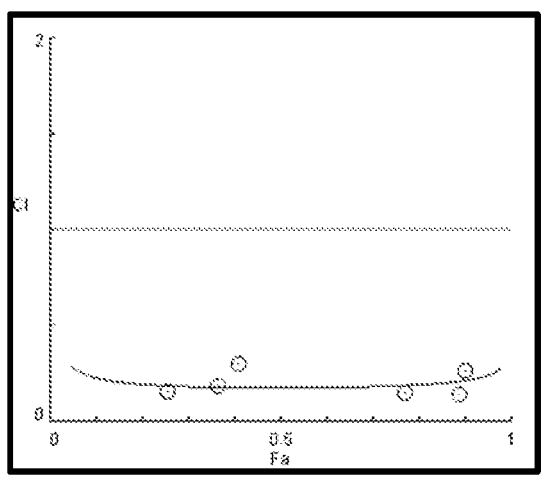
FIG. 29B illustrates the synergistic results from the combination of gemcitabine, and pan-RAF inhibitor TAK632 in Panc1 pancreatic cancer cells.
Figure 30A:
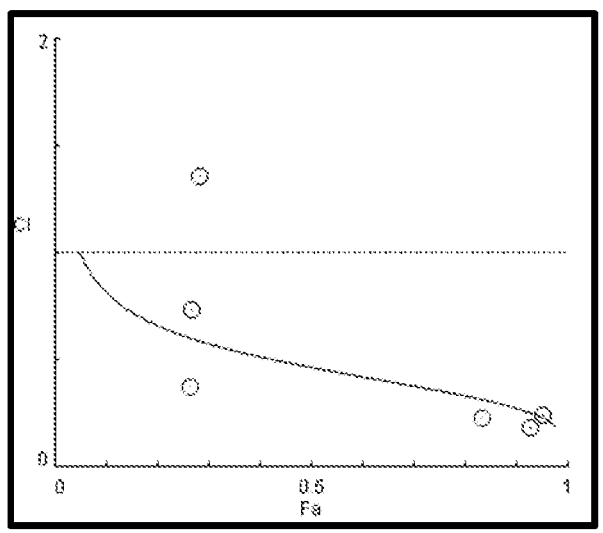
FIG. 30A illustrates the synergistic results from the combination of gemcitabine, and pan-RAF inhibitor RAF265 in BxPC3M1 pancreatic cancer cells.
Figure 30B:
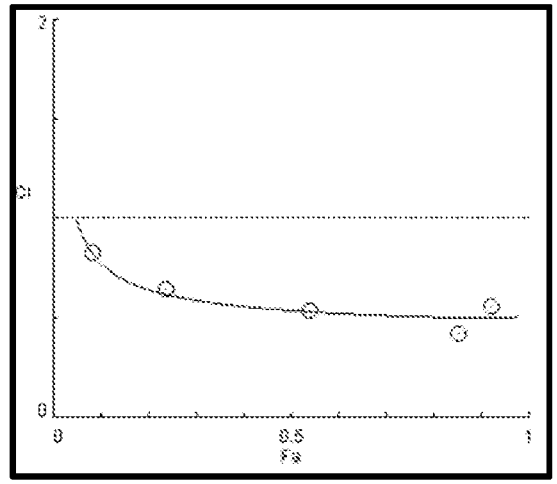
FIG. 30B illustrates the synergistic results from the combination of gemcitabine, and pan-RAF inhibitor TAK632 in BxPC3M1 pancreatic cancer cells.

Example 9: Combination of Pan-RAF Inhibitors and DNA Damaging Agents can be Used to Treat Cancers that were Previously Non-Responsive to Treatments The following example demonstrates that pan-RAF inhibitors can also be used to treat cancers that were previously non-responsive to treatments. Constant ratio combination index (CI) calculations showed significant synergy between Gemcitabine and pan-RAF inhibitors RAF265 and TAK632 in metastatic melanoma cell lines (SK-MEL- 28VR1; FIGS. 27A and 27B, and 501mel; FIGS. 28A, and 28B) and pancreatic cancer cell lines (Panc1; FIGS. 29A and 29B, BxPC3M1; FIGS. 30A and 30B).

For SK-MEL-28VR1 (FIG. 27A), the starting dose of single gemcitabine treatment was 150 nM and RAF265 was 100 µM. The dose was progressively reduced in a constant ratio by 1/2, 1/4, 1/8, 1/16, and 1/32 in consecutive wells in series triplicates. For the combination treatments, the ratio of gemcitabine to RAF265 was 1 to 200 with 25 nM as the starting dose of gemcitabine and 5 µM as the starting dose of RAF265.

For SK-MEL-28VR1 (FIG. 27B), the starting dose of single gemcitabine treatment was 150 nM and TAK632 was 100 µM. The dose was progressively reduced in a constant ratio by 1/2, 1/4, 1/8, 1/16, and 1/32 in consecutive wells in series triplicates. For the combination treatments, the ratio of gemcitabine to TAK632 was 1 to 200 with 25 nM as the starting dose of gemcitabine and 5 µM as the starting dose of TAK632.

For 501mel (FIG. 28A), the starting dose of single gemcitabine treatment was 150 nM and RAF265 was 100 µM. The dose was progressively reduced in a constant ratio by 1/2, 1/4, 1/8, 1/16, and 1/32 in consecutive wells in series triplicates. For the combination treatments, the ratio of gemcitabine to RAF265 was 1 to 200 with 25 nM as the starting dose of gemcitabine and 5 µM as the starting dose of RAF265.

For 501mel (FIG. 28B), the starting dose of single gemcitabine treatment was 150 nM and TAK632 was 100 µM. The dose was progressively reduced in a constant ratio by 1/2, 1/4, 1/8, 1/16, and 1/32 in consecutive wells in series triplicates. For the combination treatments, the ratio of gemcitabine to TAK632 was 1 to 200 with 25 nM as the starting dose of gemcitabine and 5 µM as the starting dose of TAK632.

For Panc1 (FIG. 29A), the starting dose of single gemcitabine treatment was 150 nM and RAF265 was 100 µM. The dose was progressively reduced in a constant ratio by 1/2, 1/4, 1/8, 1/16, and 1/32 in consecutive wells in series triplicates. For the combination treatments, the ratio of gemcitabine to RAF265 was 1 to 200 with 25 nM as the starting dose of gemcitabine and 5 µM as the starting dose of RAF265.

For Panc1 (FIG. 29B), the starting dose of single gemcitabine treatment was 150 nM and TAK632 was 100 µM. The dose was progressively reduced in a constant ratio by 1/2, 1/4, 1/8, 1/16, and 1/32 in consecutive wells in series triplicates. For the combination treatments, the ratio of gemcitabine to TAK632 was 1 to 200 with 25 nM as the starting dose of gemcitabine and 5 µM as the starting dose of TAK632.

For BxPC3M1 (FIG. 30A), the starting dose of single gemcitabine treatment was 150 nM and RAF265 was 100 µM. The dose was progressively reduced in a constant ratio by 1/2, 1/4, 1/8, 1/16, and 1/32 in consecutive wells in series triplicates. For the combination treatments, the ratio of gemcitabine to RAF265 was 1 to 200 with 25 nM as the starting dose of gemcitabine and 5 µM as the starting dose of RAF265.

For BxPC3M1 (FIG. 30B), the starting dose of single gemcitabine treatment was 150 nM and TAK632 was 100 µM. The dose was progressively reduced in a constant ratio by 1/2, 1/4, 1/8, 1/16, and 1/32 in consecutive wells in series triplicates. For the combination treatments, the ratio of gemcitabine to TAK632 was 1 to 200 with 25 nM as the starting dose of gemcitabine and 5 µM as the starting dose of TAK632.

Either the pan-RAF inhibitor RAF265 (FIGS. 27A, 28A, 29A, and 30A) or TAK632 (FIGS. 27B, 28B, 29B, and 30B) was added following gemcitabine wash-out on day 2. The pan-RAF inhibitor was washed out on day 4 and colonies were allowed to form for 7 days before being fixed (10% methanol+10% acetic acid) and stained with crystal violet (0.4% in 20% ethanol) for quantitation as previously described. FIG. 27A is a constant ratio FaCI plot showing synergy between gemcitabine and RAF265 in a human metastatic melanoma cell line (SK-MEL-28VR1). FIG. 27B is a constant ratio FaCI plot showing synergy between gemcitabine and TAK632 in a human metastatic melanoma cell line (SK-MEL-28VR1). FIG. 28A is a constant ratio FaCI plot showing synergy between gemcitabine and RAF265 in a human metastatic melanoma cell line (501mel). FIG. 28B is a constant ratio FaCI plot showing synergy between gemcitabine and TAK632 in a human metastatic melanoma cell line (501mel). FIG. 29A is a constant ratio FaCI plot showing synergy between gemcitabine and RAF265 in a human pancreatic cancer cell line (Panc1). FIG. 29B is a constant ratio FaCI plot showing synergy between gemcitabine and TAK632 in a human pancreatic cancer cell line (Panel). FIG. 30A is a constant ratio FaCI plot showing synergy between gemcitabine and RAF265 in a human pancreatic cancer cell line (BxPC3M1). FIG. 30B is a constant ratio FaCI plot showing synergy between gemcitabine and TAK632 in a human pancreatic cancer cell line (BxPC3M1). In totality, these results clearly show the therapeutic potential of the gemcitabine+pan-RAF inhibitor combination treatments against metastatic melanoma and pancreatic cancer. The synergy of a combination of a nucleoside analog and DNA damaging agent, such as gemcitabine, and a pan-RAF inhibitor, such as those described herein, was surprising and unexpected.

Figure 31A:
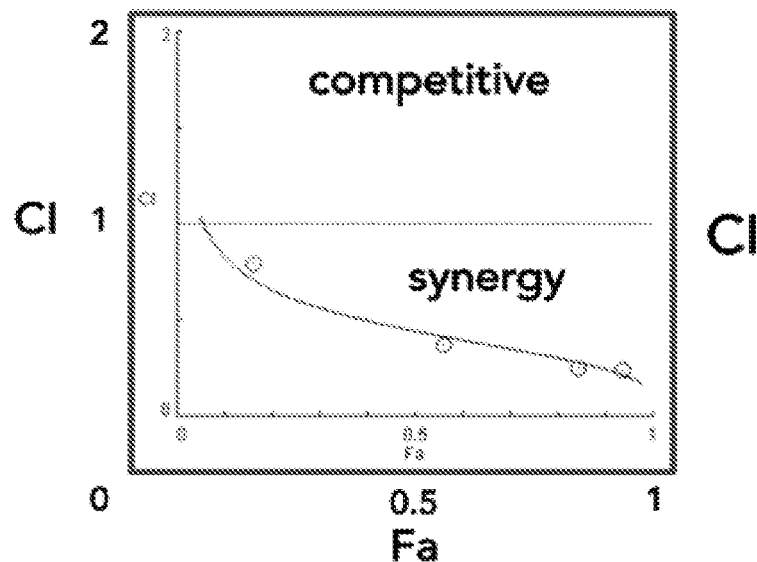
FIG. 31A illustrates the synergistic results from the combination of gemcitabine and BRAF $2^{nd}$ generation inhibitor XP102 in SK-MEL-28VR1 metastatic melanoma cells.
Figure 31B:
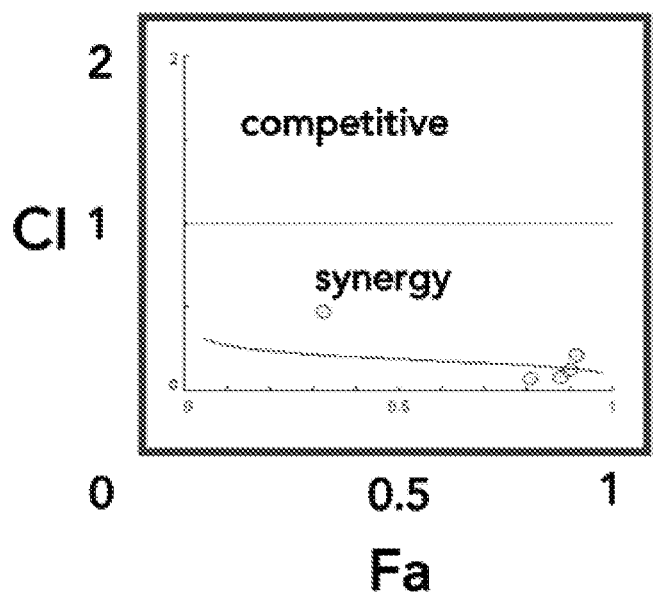
FIG. 31B illustrates the synergistic results from the combination of methotrexate and BRAF $2^{nd}$ generation inhibitor XP102 in SK-MEL-28VR1 metastatic melanoma cells.
Figure 32A:
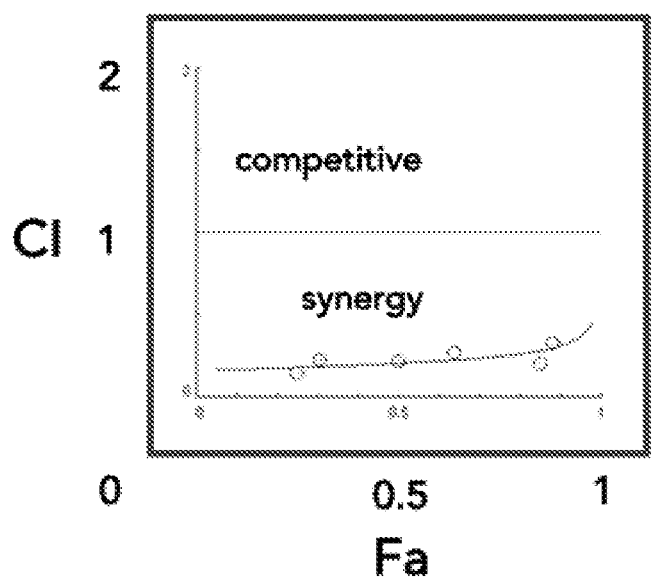
FIG. 32A illustrates the synergistic results from the combination of gemcitabine and BRAF $2^{nd}$ generation inhibitor XP102 in Panc1 pancreatic cancer cells.
Figure 32B:
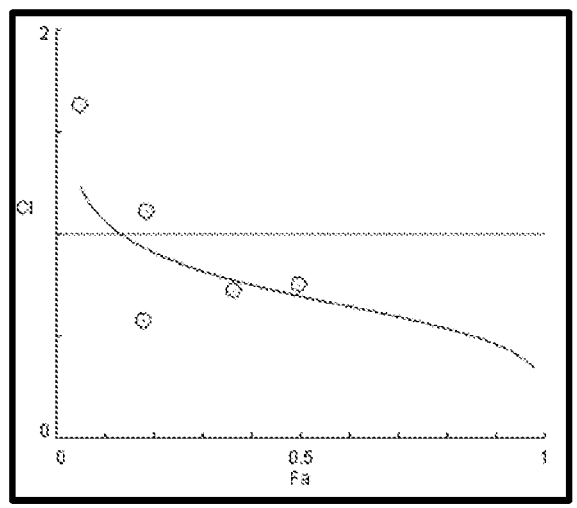
FIG. 32B illustrates the synergistic results from the combination of methotrexate and BRAF $2^{nd}$ generation inhibitor XP102 in Panc1 pancreatic cancer cells.
Figure 33A:
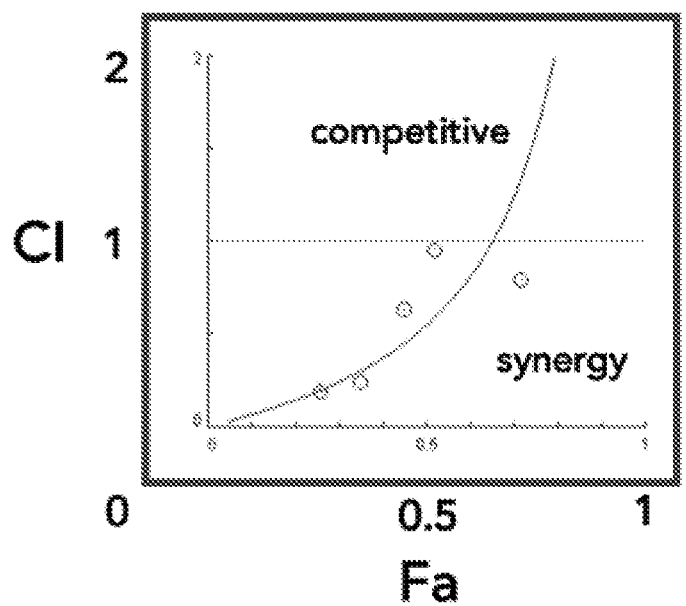
FIG. 33A illustrates the synergistic results from the combination of gemcitabine and BRAF $2^{nd}$ generation inhibitor XP102 in BxPC3M1 pancreatic cancer cells.
Figure 33B:
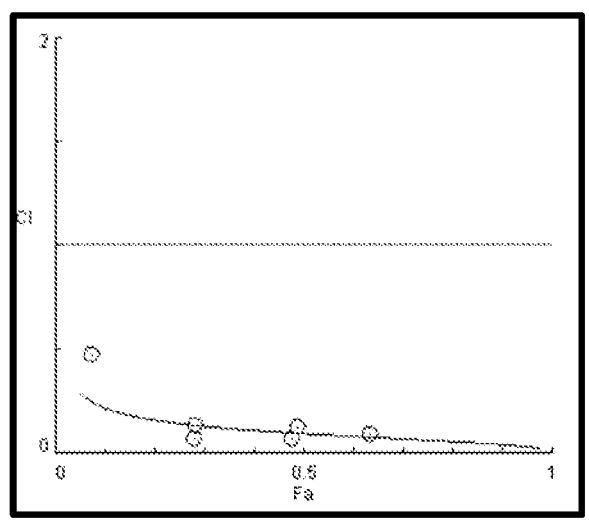
FIG. 33B illustrates the synergistic results from the combination of methotrexate and BRAF $2^{nd}$ generation inhibitor XP102 in BxPC3M1 pancreatic cancer cells.
Figure 34A:
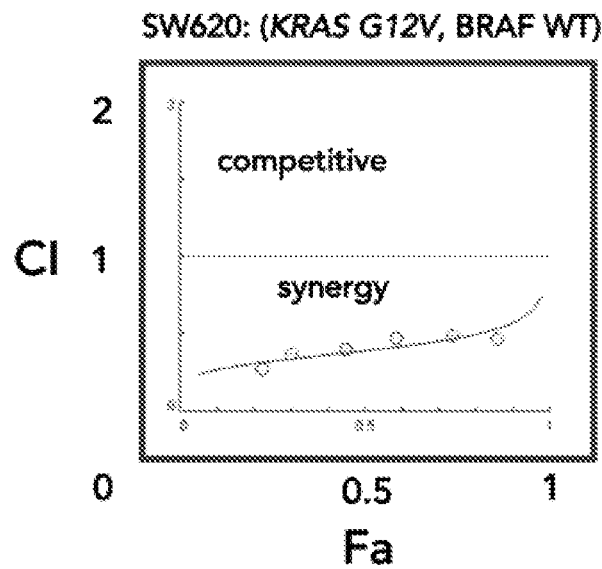
FIG. 34A illustrates the synergistic results from the combination of gemcitabine and BRAF $2^{nd}$ generation inhibitor XP102 in SW620 colon cancer cells.
Figure 34B:
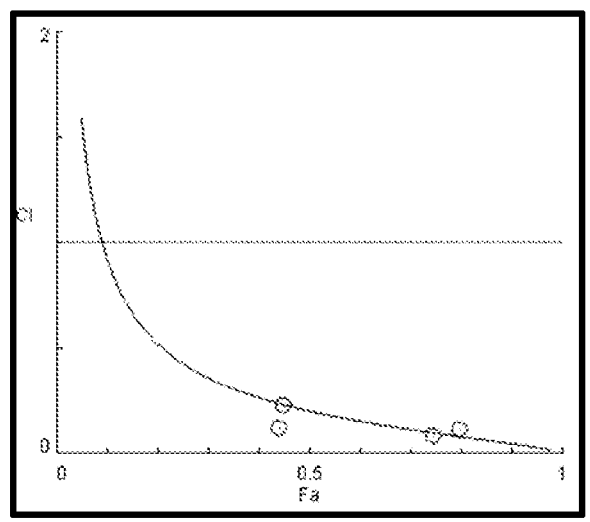
FIG. 34B illustrates the synergistic results from the combination of methotrexate and BRAF $2^{nd}$ generation inhibitor XP102 in SW620 colon cancer cells.
Figure 35A:
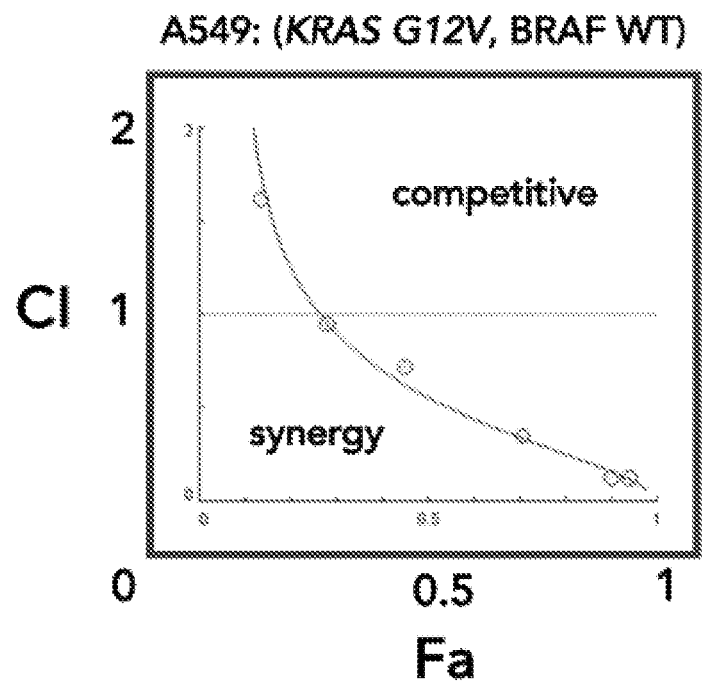
FIG. 35A illustrates the synergistic results from the combination of gemcitabine and BRAF $2^{nd}$ generation inhibitor XP102 in A549 lung cancer cells.
Figure 35B:
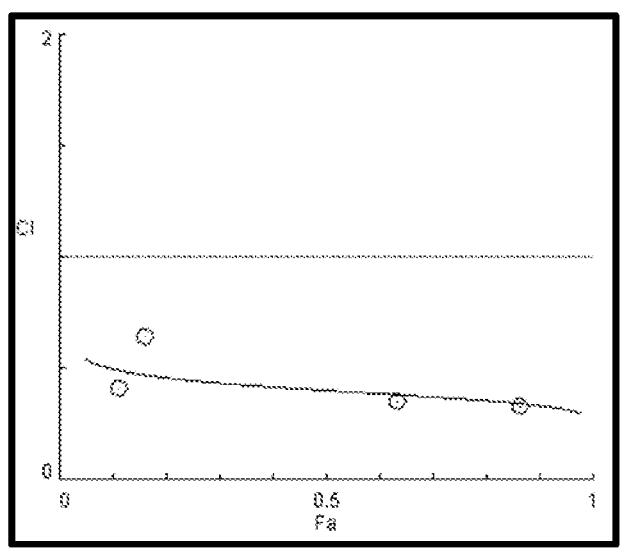
FIG. 35B illustrates the synergistic results from the combination of methotrexate and BRAF $2^{nd}$ generation inhibitor XP102 in A549 lung cancer cells.

Example 10: Combination of a Selective BRAF Inhibitor that Binds to the DFG-Out (Inactive) Conformation of the BRAF Kinase (2" Generation BRAF Inhibitor), and DNA Damaging Agents can be Used to Treat Cancers that were Previously Non-Responsive to Treatments Constant ratio combination index (CI) calculations showed significant synergy between Gemcitabine or methotrexate and BRAF inhibitor XP102 (previously known as BI882370) in a metastatic melanoma cell line (SK-MEL-28VR1; FIGS. 31A and 31B), pancreatic cancer cell lines (Panc1; FIGS. 32A and 32B, BxPC3M1; FIGS. 33A and 33B), a colon cancer cell line (SW620; FIGS. 34A and 34B), and a lung cancer cell line (A549; FIGS. 35A and 35B).

For SK-MEL-28VR1 (FIG. 31A), the starting dose of single gemcitabine treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of gemcitabine to XP102 was 1 to 200 with 25 nM as the starting dose of gemcitabine and 5 µM as the starting dose of XP102.

For SK-MEL-28VR1 (FIG. 31B), the starting dose of single methotrexate treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of methotrexate to XP102 was 1 to 200 with 25 nM as the starting dose of methotrexate and 5 µM as the starting dose of XP102.

For Panc1 (FIG. 32A), the starting dose of single gemcitabine treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of gemcitabine to XP102 was 1 to 200 with 25 nM as the starting dose of gemcitabine and 5 µM as the starting dose of XP102.

For Panc1 (FIG. 32B), the starting dose of single methotrexate treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of methotrexate to XP102 was 1 to 200 with 25 nM as the starting dose of methotrexate and 5 µM as the starting dose of XP102.

For BxPC3M1 (FIG. 33A), the starting dose of single gemcitabine treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of gemcitabine to XP102 was 1 to 200 with 25 nM as the starting dose of gemcitabine and 5 µM as the starting dose of XP102.

For BxPC3M1 (FIG. 33B), the starting dose of single methotrexate treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of methotrexate to XP102 was 1 to 200 with 25 nM as the starting dose of methotrexate and 5 µM as the starting dose of XP102.

For SW620 (FIG. 34A), the starting dose of single gemcitabine treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of gemcitabine to XP102 was 1 to 200 with 25 nM as the starting dose of gemcitabine and 5 µM as the starting dose of XP102.

For SW620 (FIG. 34B), the starting dose of single methotrexate treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of methotrexate to XP102 was 1 to 200 with 25 nM as the starting dose of methotrexate and 5 µM as the starting dose of XP102.

For A549 (FIG. 35A), the starting dose of single gemcitabine treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of gemcitabine to XP102 was 1 to 200 with 25 nM as the starting dose of gemcitabine and 5 µM as the starting dose of XP102.

For A549 (FIG. 35B), the starting dose of single methotrexate treatment was 150 nM and XP102 was 100 µM. The dose was progressively reduced in a constant ratio by 1/2, 1/4, 1/8, 1/16, and 1/32 in consecutive wells in series triplicates. For the combination treatments, the ratio of methotrexate to XP102 was 1 to 200 with 25 nM as the starting dose of methotrexate and 5 µM as the starting dose of XP102.

XP102 was added following gemcitabine (FIGS. 31A, 32A, 33A, 34A, and 35A) or methotrexate (FIGS. 31B, 32B, 33B, 34B, and 35B) wash-out on day 2. XP102 was washed out on day 4 and colonies were allowed to form for 7 days before being fixed (10% methanol+10% acetic acid) and stained with crystal violet (0.4% in 20% ethanol) for quantitation as previously described. FIG. 31A is a constant ratio FaCI plot showing synergy between gemcitabine and XP102 in a human metastatic melanoma cell line (SK-MEL-28VR1). FIG. 31B is a constant ratio FaCI plot showing synergy between methotrexate and XP102 in a human metastatic melanoma cell line (SK-MEL-28VR1). FIG. 32A is a constant ratio FaCI plot showing synergy between gemcitabine and XP102 in a human pancreatic cancer cell line (Panc1). FIG. 32B is a constant ratio FaCI plot showing synergy between methotrexate and XP102 in a human pancreatic cancer cell line (Panc1). FIG. 33A is a constant ratio FaCI plot showing synergy between gemcitabine and XP102 in a human pancreatic cancer cell line (BxPC3M1). FIG. 33B is a constant ratio FaCI plot showing synergy between methotrexate and XP102 in a human pancreatic cancer cell line (BxPC3M1). FIG. 34A is a constant ratio FaCI plot showing synergy between gemcitabine and XP102 in a human colon cancer cell line (SW620). FIG. 34B is a constant ratio FaCI plot showing synergy between methotrexate and XP102 in a human colon cancer cell line (SW620). FIG. 35A is a constant ratio FaCI plot showing synergy between gemcitabine and XP102 in a human lung cancer cell line (A549). FIG. 35B is a constant ratio FaCI plot showing synergy between methotrexate and XP102 in a human lung cancer cell line (A549). In totality, these results clearly show the therapeutic potential of the gemcitabine or methotrexate+XP102 combination treatments against metastatic melanoma, pancreatic cancer, colon cancer, and lung cancer. The synergy in treating cancer, such as cell lines derived from non-responsive tumors, of a combination of a DNA damaging agent, such as gemcitabine or methotrexate, and a selective $2^{nd}$ generation BRAF inhibitor, such as those described herein, was surprising and unexpected.

Figure 36:
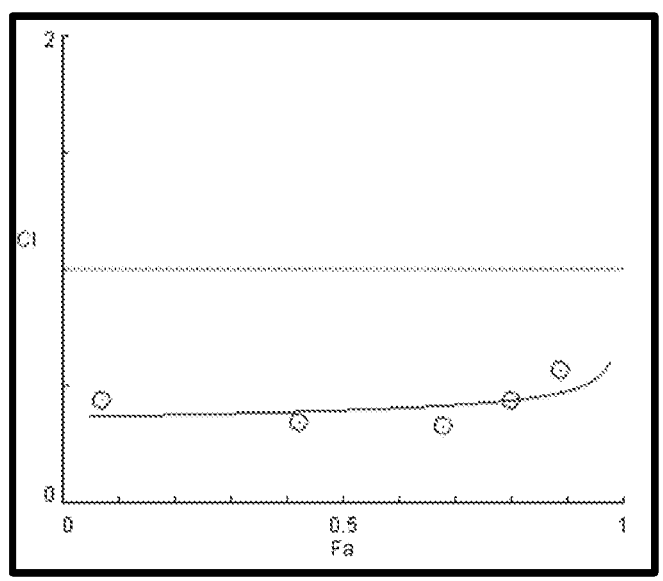
FIG. 36 illustrates the synergistic results from the combination of gemcitabine and MEK inhibitor E6201 in SK-MEL-28VR1 metastatic melanoma cells.

Example 11: Combination of a MEK Inhibitor and DNA Damaging Agents can be Used to Treat Cancers that were Previously Non-Responsive to Treatments Constant ratio combination index (CI) calculations showed significant synergy between Gemcitabine and MEK inhibitor E6201 in a metastatic melanoma cell line (SK-MEL-28VR1; FIG. 36).

For SK-MEL-28VR1 (FIG. 36), the starting dose of single gemcitabine treatment was 150 nM and E6201 was 100 µM. The dose was progressively reduced in a constant ratio by 1/2, 1/4, 1/8, 1/16, and 1/32 in consecutive wells in series triplicates. For the combination treatments, the ratio of gemcitabine to E6201 was 1 to 200 with 25 nM as the starting dose of gemcitabine and 5 µM as the starting dose of E6201.

E6201 was added following gemcitabine (FIG. 36) wash-out on day 2. E6201 was washed out on day 4 and colonies were allowed to form for 7 days before being fixed (10% methanol+10% acetic acid) and stained with crystal violet (0.4% in 20% ethanol) for quantitation as previously described. FIG. 36 is a constant ratio FaCI plot showing synergy between gemcitabine and E6201 in a human metastatic melanoma cell line (SK-MEL-28VR1). This result clearly shows the therapeutic potential of the gemcitabine+E6201 combination treatments against metastatic melanoma. The synergy of a combination of a DNA damaging agent, such as gemcitabine, and a MEK inhibitor, such as E6201, was surprising and unexpected.

In conclusion, the combinations of the inhibitors provided herein, such as the different types of BRAF, CRAF, pan-RAF, MEK inhibitors and BRAF inhibitors that are specific for the the DFG-out (inactive) conformation of the BRAF kinase, such as, vemurafenib, dabrafenib, sorafenib, encorafenib, RAF265, AD80, GDC0879, AZ628, ZM336372, NVPBHG712, LY3009120, TAK632, MLN2480, or XP102, in combination with DNA damaging agents, such as, but not limited to, gemcitabine, methotrexate, or camptothecin, and the like, were found to sensitize resistant cancer cell lines to these inhibitors that were previously thought to be insensitive to these classes of compounds. The combination can also be enhanced with the addition of other types of inhibitors, such as taxanes, MEK inhibitors, or EGFR inhibitors. The results also demonstrate that the combinations are not specific to any one BRAF, CRAF, or pan-RAF inhibitor and can be used across a spectrum of BRAF, CRAF, or pan-RAF inhibitors as described and exemplified herein. These results were surprising and unexpected and allow new treatments for cancers that had few options for treatment.

While the embodiments described herein have been described with reference to examples, those skilled in the art recognize that various modifications may be made without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

What is claimed is:

1. A method of treating a wild-type BRAF tumor in a subject comprising administering to the subject a DNA damaging agent and a pan-RAF inhibitor, wherein the tumor is a pancreatic tumor, melanoma tumor, or colon cancer tumor, wherein the pan-RAF inhibitor is 1-methyl-5-[[2-[5-(trifluoromethyl)-1H-imidazol-2-yl]-4-pyridinyl]oxy]-N-[4-(trifluoromethyl)phenyl]-2-benzimidazolamine (RAF265), 3-(2-cyanopropan-2-yl)-N-[4-methyl-3[(3-methyl-4-oxo-quinazolin-6-yl)amino]phenyl]benzamide (AZ628), 1-(3,3-dimethylbutyl)-3-[2-fluoro-4-methyl-5-[7-methyl-2-(methylamino)pyrido[2,3-d]pyrimidin-6-yl]phenyl]urea (LY3009120), N-[7-Cyano-6-[4-fluoro-3-[[2-[3-(trifluoromethyl)phenyl]acetyl]amino]phenoxy]-1,3-benzothiazol-2-1]cyclopropanecarboxamide (TAK632), 2-[(1R)-1-[(6-Amino-5-chloropyrimidine-4-carbonyl)amino]ethyl]-N-[5-chloro-4-(trifluoromethyl)pyridin-2-yl]-1,3-thiazole-4-carboxamide (MLN2480), N-[3-[5-[(1-Ethylpiperidin-4-yl)-methylamino]-3-pyrimidin-5-ylpyrrolo[3,2-b]pyridin-1-yl]-2,4-difluorophenyl]propane-1-sulphonamide (XP102), or a pharmaceutically acceptable salt thereof, and wherein the DNA damaging agent is gemcitabine, 5-fluorouracil, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, [(5S,6S)-6-Acetyloxy-11-methoxy-2,7,7-trimethyl-13-oxo-8-oxa-2-azapentacyclo[12.8.0.03,12.04,9.016,21]docosa-1(22),3,9,11,14,16,18,20-octaen-5-yl] acetate (S-23906), (19S)-10,19-diethyl-7,19-dihydroxy-17-oxa-3,13-diazapentacyclo[11.8.0.02,11.04,9.015,20]henicosa-1(21),2,4(9),5,7,10,15(20)-heptaene-14,18-dione(SN-38), topotecan, camptothecin, rebeccamiycin, or any pharmaceutically acceptable salt thereof.

2. The method of claim 1, wherein the DNA damaging agent is gemcitabine, methotrexate, camptothecin, and/or pyrimethamine, or a pharmaceutically acceptable salt thereof.

3. The method of claim 1, wherein the inhibitor, or a pharmaceutically acceptable salt thereof, and the DNA damaging agent is administered sequentially, simultaneously, or in an overlapping manner.

4. The method of claim 1, wherein the DNA damaging agent is administered to the subject prior to the inhibitor being administered to the subject.

5. The method of claim 1, wherein the subject is pretreated with the DNA damaging agent before the inhibitor is administered to the subject.

6. The method of claim 1, wherein the inhibitor, or a pharmaceutically acceptable salt thereof, and the DNA damaging agent is administered orally.

7. The method of claim 1, wherein the inhibitor, or a pharmaceutically acceptable salt thereof, and the DNA damaging agent is administered intravenously.

8. The method of claim 1, wherein the inhibitor, or a pharmaceutically acceptable salt thereof, is administered orally and the DNA damaging agent is administered intravenously.

9. The method of claim 1, wherein the inhibitor is RAF265, or a pharmaceutically acceptable salt thereof.

10. The method of claim 1, wherein the tumor is a pancreatic tumor.

11. The method of claim 1, wherein the tumor is a melanoma tumor.

12. The method of claim 1, wherein the tumor is a metastatic tumor.

13. The method of claim 1, wherein the tumor is characterized as wild-type RAS.

14. The method of claim 1, wherein the tumor is characterized as wild-type BRAF and mutant RAS.

15. A method of treating a wild-type BRAF melanoma tumor in a subject comprising administering to the subject a DNA damaging agent and a pan-RAF inhibitor, wherein the pan-RAF inhibitor is RAF265, wherein the DNA damaging agent is gemcitabine, 5-fluorouracil, cytarabine, methotrexate, pyrimethamine, bleomycin, oxaliplatin, cisplatin, carboplatin, etoposide, doxorubicin, vinorelbin, mitoxantrone, podophyllotoxin, aphidicolin, fotemustine, carmustine, [(5S, 6S)-6-Acetyloxy-11-methoxy-2,7,7-trimethyl-13-oxo-8-oxa-2-azapentacyclo[12.8.0.03,12.04,9.016,21]docosa-1(22),3,9,11,14,16,18,20-octaen-5-yl] acetate (S-23906), (19S)-10,19-diethyl-7,19-dihydroxy-17-oxa-3,13-diazapentacyclo[11.8.0.02,11.04,9.015,20]henicosa-1(21),2,4(9),5,7,10,15(20)-heptaene-14,18-dione(SN-38), topotecan, camptothecin, rebeccamycin, or any pharmaceutically acceptable salt thereof.

16. The method of claim 1, wherein the tumor is a colon cancer tumor.

* * * * *